(12) United States Patent
Oka et al.

(10) Patent No.: US 9,113,536 B2
(45) Date of Patent: Aug. 18, 2015

(54) ELECTROLUMINESCENT DEVICE

(75) Inventors: Hidetaka Oka, Takarazuka (JP);
Ramachandra V. Joshi, Thane (IN);
Junichi Tanabe, Amagasaki (JP);
Sanjoy Lahiri, Mumbai (IN); Dhaval Vashi, Mumbai (IN); Preetam Ghogale, Mumbai (IN)

(73) Assignee: BASF SE, Ludwigshafen (DE)

( * ) Notice: Subject to any disclaimer, the term of this patent is extended or adjusted under 35 U.S.C. 154(b) by 1843 days.

(21) Appl. No.: 11/919,105

(22) PCT Filed: Apr. 19, 2006

(86) PCT No.: PCT/EP2006/061670
§ 371 (c)(1),
(2), (4) Date: Oct. 23, 2007

(87) PCT Pub. No.: WO2006/114377
PCT Pub. Date: Nov. 2, 2006

(65) Prior Publication Data
US 2009/0066231 A1 Mar. 12, 2009

(30) Foreign Application Priority Data

Apr. 28, 2005 (EP) .................................. 05103497
Aug. 30, 2005 (EP) .................................. 05107906

(51) Int. Cl.
C09K 11/06 (2006.01)
H05B 33/14 (2006.01)
H01L 51/54 (2006.01)
C07D 249/08 (2006.01)

(52) U.S. Cl.
CPC .............. *H05B 33/14* (2013.01); *C07D 249/08* (2013.01); *C09K 11/06* (2013.01); *C09K 2211/1059* (2013.01); *C09K 2211/1062* (2013.01)

(58) Field of Classification Search
CPC combination set(s) only.
See application file for complete search history.

(56) References Cited

U.S. PATENT DOCUMENTS

| 3,592,656 A | 7/1971 | Brooks | |
| 4,769,292 A * | 9/1988 | Tang et al. | 428/690 |
| 6,803,380 B1 | 10/2004 | Pascal et al. | |
| 6,916,554 B2 * | 7/2005 | Ma et al. | 428/690 |
| 2002/0180347 A1 * | 12/2002 | Adachi et al. | 313/503 |

FOREIGN PATENT DOCUMENTS

| CH | 542 212 | 11/1973 |
| DE | 1132927 | 7/1962 |
| DE | 129908 | 2/1978 |
| JP | 52-035300 | 3/1977 |
| JP | 56-164464 | 12/1981 |

(Continued)

OTHER PUBLICATIONS

Kato et al., JP (2005)-044790, machine assisted translation.*

(Continued)

*Primary Examiner* — J. L. Yang
(74) *Attorney, Agent, or Firm* — Shruti Costales

(57) ABSTRACT

The present invention relates to electroluminescent devices that comprise organic layers that contain triazole compounds of the formula (I), or formula (II). The compounds are suitable components of, for example, blue-emitting, durable, organo-electroluminescent layers. The electroluminescent devices may be employed for full color display panels in, for example, mobile phones, televisions and personal computer screens.

10 Claims, 1 Drawing Sheet

(56) References Cited

FOREIGN PATENT DOCUMENTS

| | | |
|---|---|---|
| JP | 2000-100570 | 4/2000 |
| JP | 2003-5356 | 1/2003 |
| JP | 2003-109765 | 4/2003 |
| JP | 2003-513961 | 4/2003 |
| JP | 2004-146368 | 5/2004 |
| JP | 2004-253298 | 9/2004 |

OTHER PUBLICATIONS

Kohama et al., JP(2000)-100570, machine assisted translation.*
Takahashi et al., JP(2003)-005356, machine assisted translation.*
Derwent abstract No. 1973-77758U[51] of CH 542 212.
Patent abstracts of Japan 2000-100570.
Patent abstracts of Japan 2003-005356.
Patent abstracts of Japan 2004-146368.
English language machine-generated translation for JP2004-253298 (108 pages); 2004.
English language machine-generated translation for DE1132927 (5 pages); 1962.
English language machine-generated translation for JP2003-109765 (33 pages); 2003.
English language abstract for JPS52-035300 (1 page); 1977.
Feist, M. et al., "Substituted 2,5-Diaryl-2H-Tetrazoles: A combined investigation of their thermal behaviour by simultaneous thermal analysis, mass spectrometry and high-performance liquid chromatography", Journal of Thermal Analysis, 1987, vol. 32, No. 6, pp. 1957-1967.
Wolchowe, H., "Triazoles from dibenzamide or di-p-toluamide and hydrazine salts", Monatshefte fuer Chemie, 1916, vol. 37, pp. 473-487.

* cited by examiner

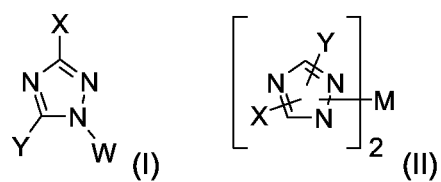

ELECTROLUMINESCENT DEVICE

The present invention relates to electroluminescent devices that comprise organic layers that contain triazole compounds. The compounds are suitable components of, for example, blue-emitting, durable, organo-electroluminescent layers. The electroluminescent devices may be employed for full color display panels in, for example, mobile phones, televisions and personal computer screens.

CH542212 discloses the following two compounds

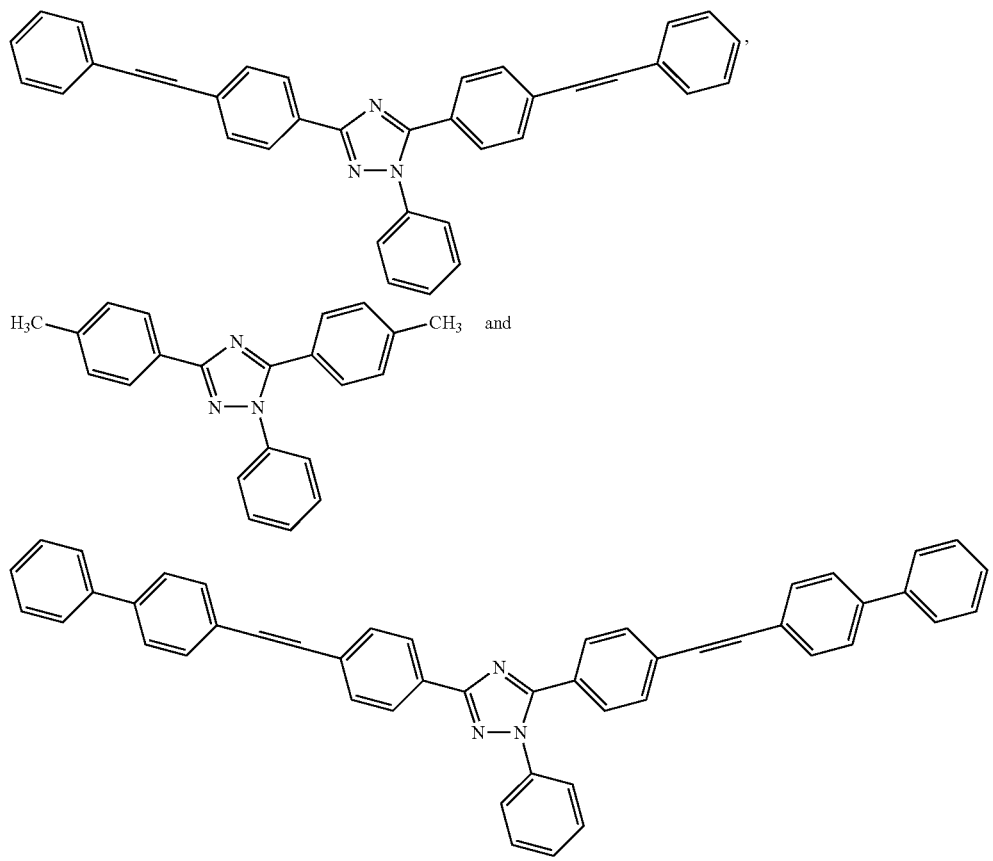

and their use as fluorescent whitening agent.

JP2000-100570 discloses metal complexes of 1,2,4-triazoles as emitting material for OLEDs. The 1,2,4-triazoles are characterized by having a 2-hydroxyphenyl group on the 1-site. The triazoles of the present invention do not contain such a group.

The two compounds below are described in JP2003-005356 and are used as one of the components of a chemically amplified photoresist.

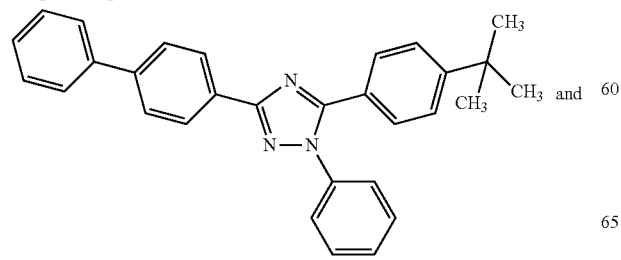

JP2004-146368 describes dimeric type 5-membered heteroaromatics as emitting layer for OLED, especially as a host material for phosphorescent guest materials. 1,2,4-triazole is mentioned as an example of a 5-membered heteroaromatic. The following compounds are explicitly mentioned:

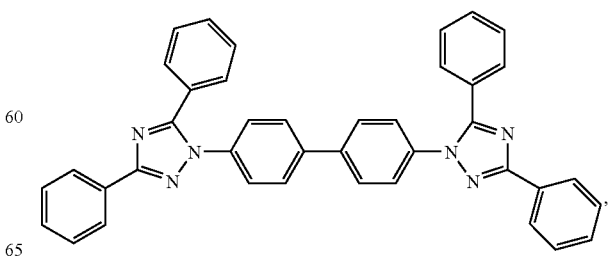

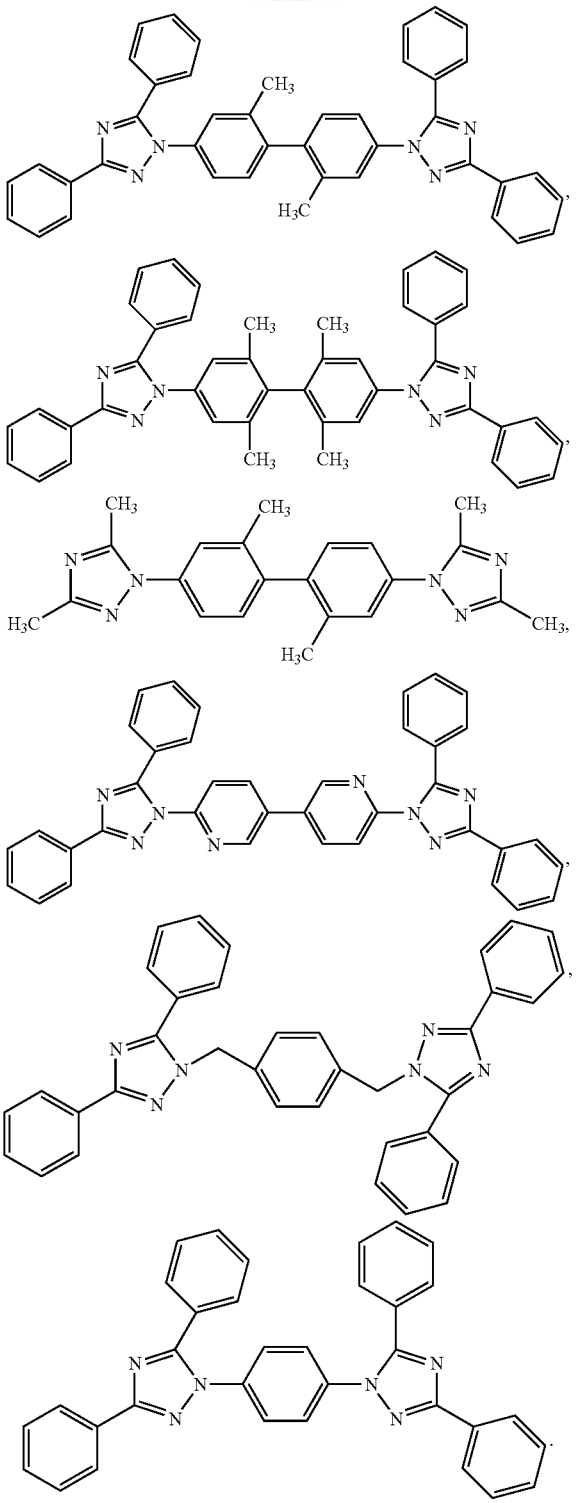

JP2004-253298 discloses a uniform white light-emitting organic electroluminescent element comprising at least one of the materials (A1-1)-(F1-5). Dimeric 5-membered heteroaromatics are part of (A1-1)-(F1-5). The explicitly disclosed 1,2,4-triazoles structures are the same as in JP2004-146368.

Surprisingly, it was found that luminescent devices, which are high durability besides high in the efficiency of electrical energy utilisation and high in luminance, can be obtained if specific triazole compounds are used, especially as light emitting substances.

Accordingly, the present invention relates to compounds of the formula

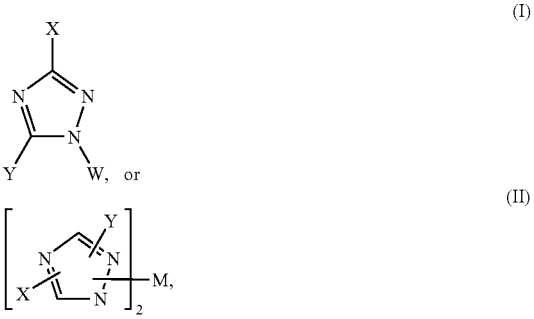

wherein

X, Y and W are independently of each other $C_1$-$C_{24}$alkyl; $C_1$-$C_{24}$alkyl, which is substituted by E and/or interrupted by D; $C_2$-$C_{18}$alkenyl, $C_2$-$C_{18}$alkenyl, which is substituted by E, $C_3$-$C_8$cycloalkyl, $C_3$-$C_8$cycloalkyl, which is substituted by G, aryl, aryl, which is substituted by G, heteroaryl, or heteroaryl, which is substituted by G, M is single (direct) bond, —CO—, —COO—; —S—; —SO—; —SO$_2$—; —O—; $C_1$-$C_{12}$alkylene, $C_2$-$C_{12}$alkenylene, or $C_2$-$C_{12}$alkinylene, which are optionally interrupted by one or more —O—, or —S—; arylene, or heteroarylene, which is optionally substituted by G, especially naphthylene, biphenylene or styrylene, which are optionally substituted by $C_1$-$C_{12}$alkyl, halogen, —OR$^{201}$, —SR$^{202}$ and/or —NR$^{203}$R$^{204}$, R$^{201}$ is hydrogen, $C_1$-$C_{24}$alkyl, $C_1$-$C_{24}$alkyl, which is substituted by E and/or interrupted by D; $C_2$-$C_{12}$alkenyl, $C_3$-$C_6$alkenoyl, $C_3$-$C_8$cycloalkyl, or benzoyl, each of which may optionally be substituted by one or more groups $C_1$-$C_6$alkyl, halogen, —OH and/or $C_1$-$C_4$alkoxy; $C_6$-$C_{14}$aryl, especially phenyl, naphthyl, phenanthryl, or anthranyl, each of which may optionally be substituted by halogen, —OH, $C_1$-$C_{12}$alkyl, $C_1$-$C_{12}$alkoxy, phenoxy, $C_1$-$C_{12}$alkylsulfanyl, phenylsulfanyl, —N($C_1$-$C_{12}$alkyl)$_2$ and/or diphenylamino;

R$^{202}$ is $C_1$-$C_{24}$alkyl, $C_1$-$C_{24}$alkyl, which is substituted by E and/or interrupted by D; $C_2$-$C_{12}$alkenyl, $C_1$-$C_8$alkanoyl, $C_2$-$C_{12}$alkenyl, $C_3$-$C_6$alkenoyl; $C_3$-$C_8$cycloalkyl, or benzoyl, each of which may optionally be substituted by one or more groups $C_1$-$C_6$alkyl, halogen, —OH, $C_1$-$C_4$alkoxy or $C_1$-$C_4$alkylsulfanyl; $C_6$-$C_{14}$aryl, especially phenyl, naphthyl, phenanthryl, or anthranyl, each of which may optionally be substituted by halogen, $C_1$-$C_{12}$alkyl, $C_1$-$C_{12}$alkoxy, phenyl-$C_1$-$C_3$alkyloxy, phenoxy, $C_1$-$C_{12}$alkylsulfanyl, phenylsulfanyl, —N($C_1$-$C_{12}$alkyl)$_2$, diphenylamino, —(CO)O($C_1$-$C_8$alkyl), —(CO)—$C_1$-$C_8$alkyl, or (CO)N($C_1$-$C_8$alkyl)$_2$;

R$^{203}$ and R$^{204}$ are independently of each other hydrogen, $C_1$-$C_{24}$alkyl, $C_1$-$C_{24}$alkyl, which is substituted by E and/or interrupted by D; $C_2$-$C_5$alkenyl, $C_3$-$C_8$cycloalkyl, or benzoyl, each of which may optionally be substituted by one or more groups $C_1$-$C_6$alkyl, halogen, —OH, or $C_1$-$C_4$alkoxy; phenyl-$C_1$-$C_3$alkyl, $C_1$-$C_8$alkanoyl, $C_3$-$C_{12}$alkenoyl, $C_6$-$C_{14}$aryl, especially phenyl naphthyl, phenanthryl or anthranyl, each of which is optionally substituted by $C_1$-$C_{12}$alkyl, benzoyl or $C_1$-$C_{12}$alkoxy; or R$^{203}$ and R$^{204}$ together are $C_2$-$C_8$alkylene, or branched $C_2$-$C_8$alkylene optionally interrupted by —O—, —S—, or —NR$^{205}$— and/or optionally substituted by hydroxyl, $C_1$-$C_4$alkoxy, $C_2$-$C_4$alkanoyloxy, or benzoyloxy, wherein the ring formed by $R^{203}$ and $R^{204}$ can optionally be condensed one or two times by phenyl which can be substituted one to three times with $C_1$-$C_8$-alkyl, $C_1$-$C_8$-alkoxy, halogen and cyano;

$R^{205}$ is hydrogen, $C_1$-$C_{24}$alkyl, $C_1$-$C_{24}$alkyl, which is substituted by E and/or interrupted by D; $C_2$-$C_5$alkenyl, $C_3$-$C_8$cycloalkyl, phenyl-$C_1$-$C_3$alkyl, $C_1$-$C_8$alkanoyl, $C_3$-$C_{12}$alkenoyl, $C_6$-$C_{14}$aryl, especially benzoyl; phenyl, naphthyl, phenanthryl or anthranyl, each of which is optionally substituted by $C_1$-$C_{12}$alkyl, benzoyl, or $C_1$-$C_{12}$alkoxy;

D is —CO—, —COO—, —OCOO—, —S—, —SO—, —SO$_2$—, —O—, —NR$^5$—, —SiR$^{61}$R$^{62}$—, —POR$^5$—, —CR$^{63}$=CR$^{64}$—, or —C≡C—;

E is halogen, $C_6$-$C_{14}$aryl, especially phenyl, naphthyl, phenanthryl, or anthranyl, which may be substituted by —OR$^{201}$, —SR$^{202}$ and/or —NR$^{203}$R$^{204}$; —OR$^{5'}$, —SR$^{5'}$, —NR$^5$R$^6$, —COR$^8$, —COOR$^7$, —CONR$^5$R$^6$, —CN, halogen, or $C_1$-$C_{18}$alkyl, G is E, or $C_1$-$C_{18}$alkyl, wherein R$^5$ and R$^6$ are independently of each other H, $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl or $C_1$-$C_{18}$alkyl which is interrupted by —O—; or R$^5$ and R$^6$ together form a five or six membered ring, in particular

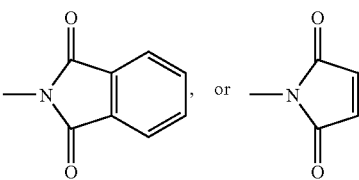

R$^{5'}$ is R$^5$, except hydrogen,

R$^7$ is H, $C_6$-$C_{18}$aryl, $C_7$-$C_{12}$alkylaryl, which are optionally substituted by $C_1$-$C_{18}$alkyl, or $C_1$-$C_{18}$alkoxy; $C_1$-$C_{18}$alkyl; or $C_1$-$C_{18}$alkyl which is interrupted by —O—;

R$^8$ is $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl, $C_7$-$C_{12}$alkylaryl, or $C_1$-$C_{18}$alkyl which is interrupted by —O—;

R$^{61}$ and R$^{62}$ are independently of each other $C_6$-$C_{18}$aryl; $C_6$-$C_{18}$aryl which is substituted by $C_1$-$C_{18}$alkyl, $C_1$-$C_{18}$alkoxy; or $C_1$-$C_{18}$alkyl which is interrupted by —O—, and R$^{63}$ and R$^{64}$ are independently of each other H, $C_6$-$C_{18}$aryl; $C_6$-$C_{18}$aryl which is substituted by $C_1$-$C_{18}$alkyl, $C_1$-$C_{18}$alkoxy; or $C_1$-$C_{18}$alkyl which is interrupted by —O—;

with the proviso that the following compounds are excluded:

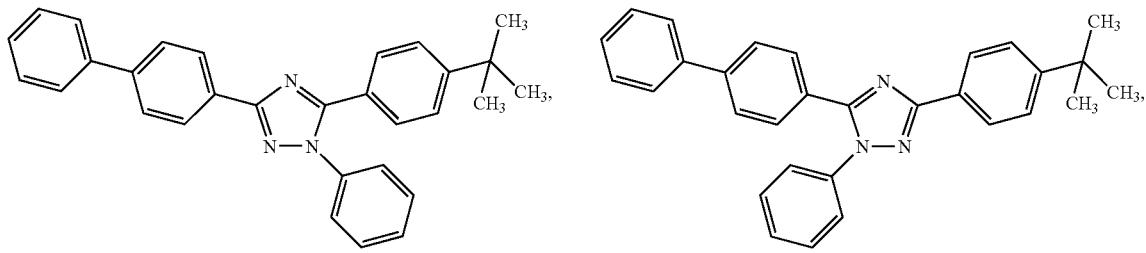

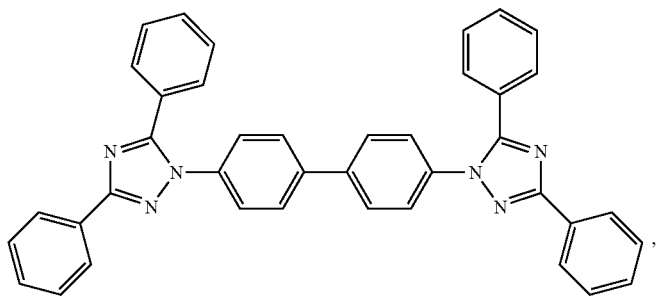

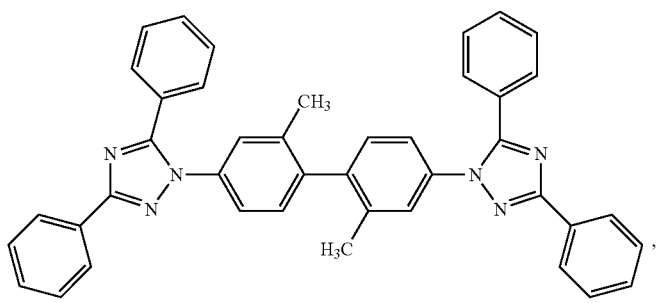

-continued
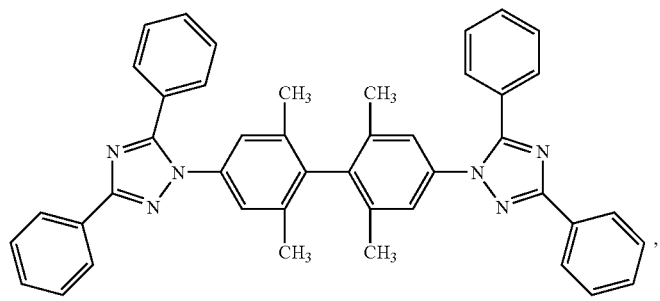
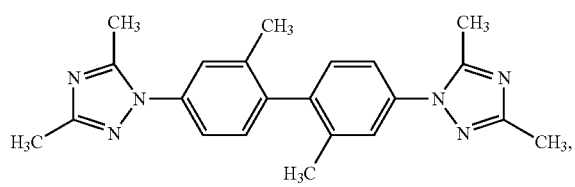
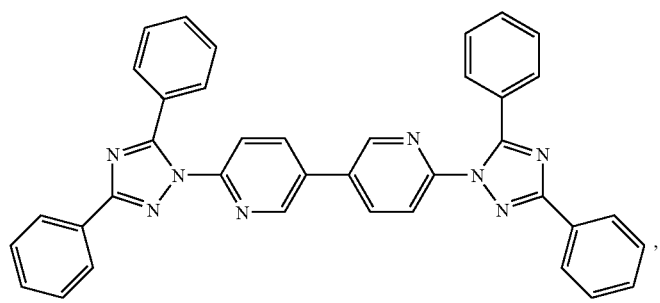
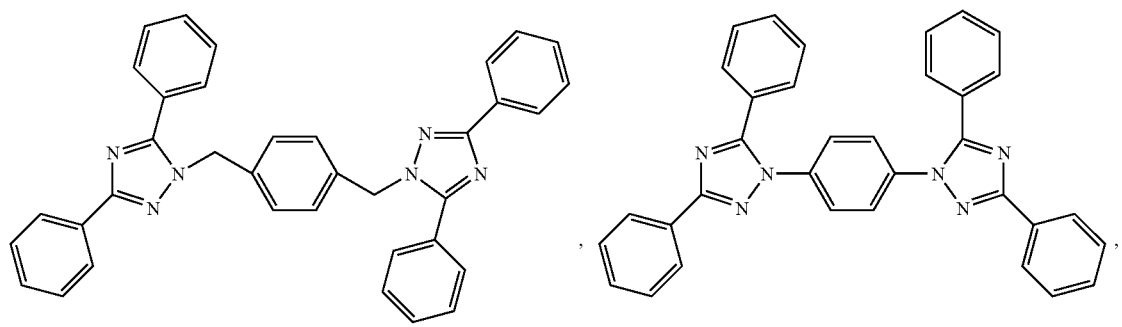
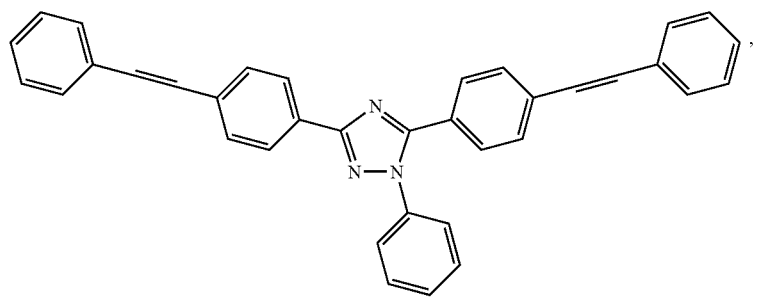
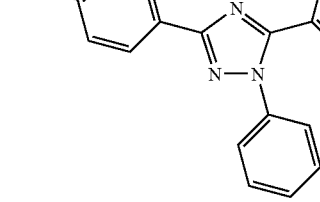 and

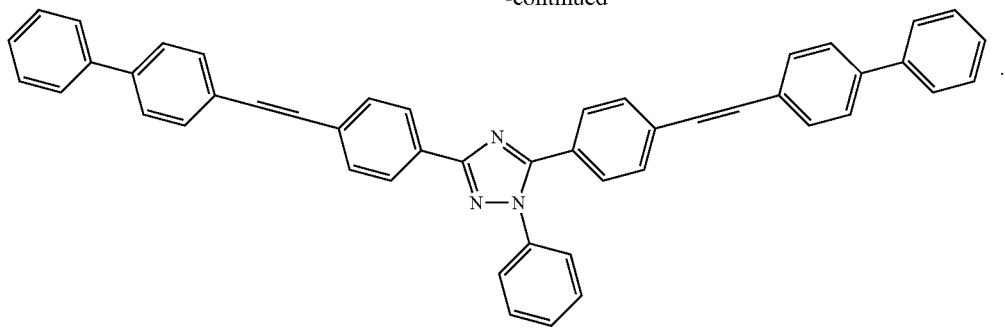

Preferably, the compound or compounds of the present invention emit light below about 520 nm, in particular between about 380 nm and about 520 nm.

The compound or compounds of the present invention have especially a NTSC coordinate of between about (0.12, 0.05) and about (0.16, 0.10), very especially a NTSC coordinate of about (0.14, 0.08).

The compound or compounds of the present invention have a melting point above about 150° C., preferably above about 200° C. and most preferred above about 250° C.

To obtain organic layers of this invention with the proper $T_g$, or glass transition temperature, it is advantageous that the present organic compounds have a glass transition temperature greater than about 100° C., for example greater than about 110° C., for example greater than about 120° C., for instance greater than about 130° C.

In one embodiment of the present invention compounds of formula I, or II are preferred, wherein at least one of the groups X, Y, and W is a $C_7$-$C_{30}$aryl group, especially a polycyclic $C_8$-$C_{30}$aryl group. Compounds of formula I, or II are even more preferred, wherein at least two of the groups X, Y, and W are a $C_7$-$C_{30}$aryl group, especially a polycyclic $C_8$-$C_{30}$aryl group. Examples of a polycyclic $C_8$-$C_{30}$aryl group are given below.

In a further embodiment of the present invention compounds of formula II are preferred, wherein M is a single bond, —CO—, —COO—, —S—, —SO—, —SO$_2$—, —O—,

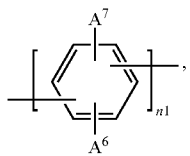

especially

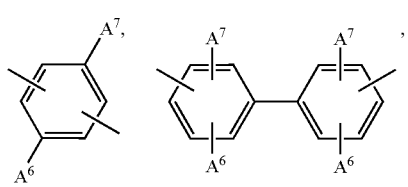

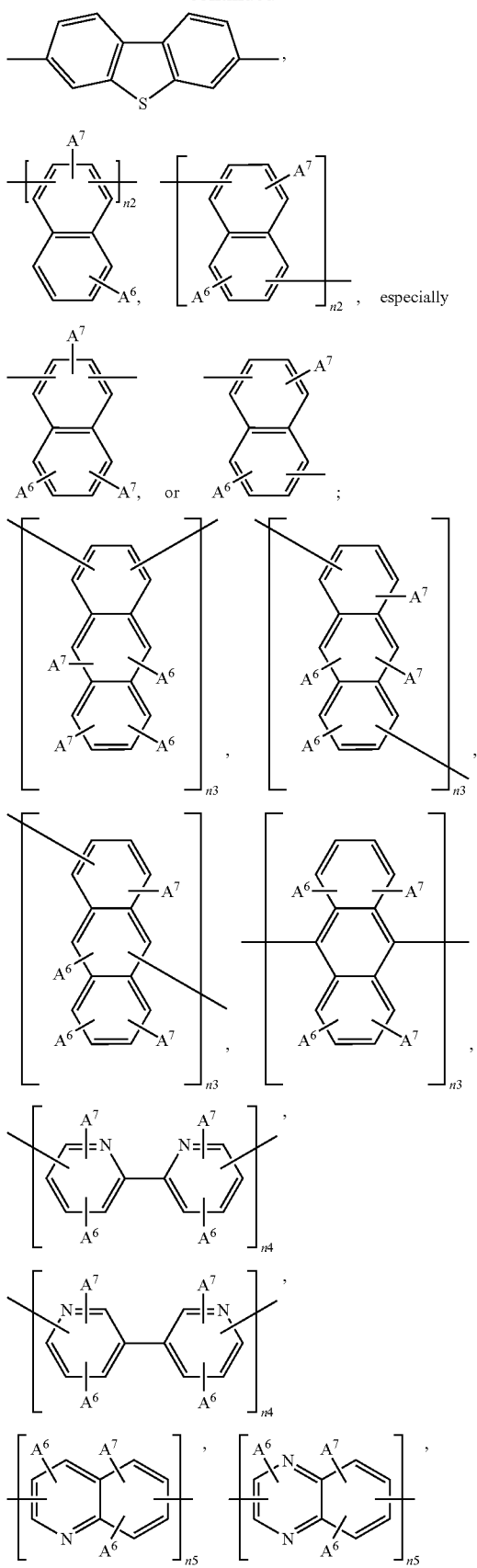
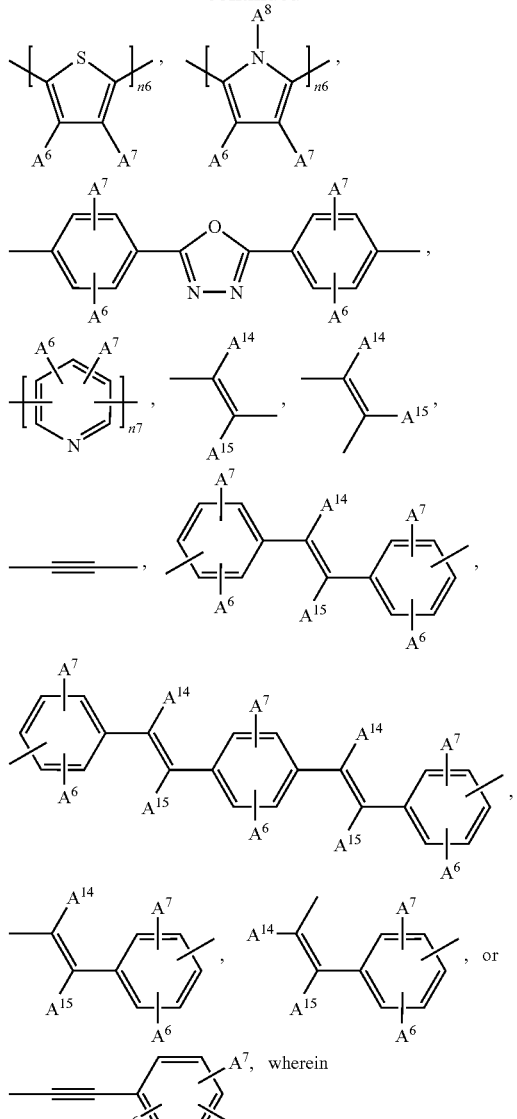

n1, n2, n3, n4, n5, n6 and n7 are integers of 1 to 10, in particular 1 to 3, $A^6$ and $A^7$ are independently of each other H, $C_1$-$C_{18}$alkyl, $C_1$-$C_{18}$alkyl which is substituted by E' and/or interrupted by D', $C_6$-$C_{24}$aryl, $C_6$-$C_{24}$aryl which is substituted by G', $C_2$-$C_{20}$heteroaryl, $C_2$-$C_{20}$heteroaryl which is substituted by G', $C_2$-$C_{18}$alkenyl, $C_2$-$C_{18}$alkynyl, $C_1$-$C_{18}$alkoxy, $C_1$-$C_{18}$alkoxy which is substituted by E' and/or interrupted by D', $C_7$-$C_{25}$aralkyl, or —CO-$A^{28}$, $A^8$ is $C_1$-$C_{18}$alkyl, $C_1$-$C_{18}$alkyl which is substituted by E' and/or interrupted by D', $C_6$-$C_{24}$ aryl, or $C_7$-$C_{25}$aralkyl, $A^9$ and $A^{10}$ are independently of each other $C_1$-$C_{18}$alkyl, $C_1$-$C_{18}$alkyl which is substituted by E' and/or interrupted by D', $C_6$-$C_{24}$aryl, $C_6$-$C_{24}$aryl which is substituted by G', $C_2$-$C_{20}$heteroaryl, $C_2$-$C_{20}$heteroaryl which is substituted by G', $C_2$-$C_{18}$alkenyl, $C_2$-$C_{18}$alkynyl, $C_1$-$C_{18}$alkoxy, $C_1$-$C_{18}$alkoxy which is substituted by E' and/or interrupted by D', or $C_7$-$C_{25}$aralkyl, or $A^9$ and $A^{10}$ form a ring, especially a five- or six-membered ring, which can optionally be substituted by one or more $C_1$-$C_{18}$ alkyl groups;

$A^{14}$ and $A^{15}$ are independently of each other H, $C_1$-$C_{18}$alkyl, $C_1$-$C_{18}$alkyl which is substituted by E' and/or interrupted by D', $C_6$-$C_{24}$aryl, $C_6$-$C_{24}$aryl which is substituted by G', $C_2$-$C_{20}$heteroaryl, or $C_2$-$C_{20}$heteroaryl which is substituted by G', D' is —CO—; —COO—; —S—; —SO—; —SO$_2$—; —O—; —NA$^{25}$-; —SiA$^{30}$A$^{31}$-; —POA$^{32}$-; —CA$^{23}$=CA$^{24}$-; or —C≡C—; and E' is —OA$^{29}$; —SA$^{29}$; —NA$^{25}$A$^{26}$; —COA$^{28}$; —COOA$^{27}$; —CONA$^{25}$A$^{26}$; —CN; —OCOOA$^{27}$; or halogen; G' is E', or $C_1$-$C_{18}$alkyl; wherein $A^{23}$, $A^{24}$, $A^{25}$ and $A^{26}$ are independently of each other H; $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl, or $C_1$-$C_{18}$alkyl which is interrupted by —O—; or $A^{25}$ and $A^{26}$ together form a five or six membered ring, in particular

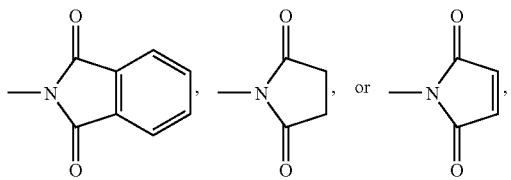

$A^{27}$ and $A^{28}$ are independently of each other H; $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl, or $C_1$-$C_{18}$alkyl which is interrupted by —O—, $A^{29}$ is H; $C_6$-$C_{18}$aryl; $C_6$-$C_{18}$aryl, which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—, $A^{30}$ and $A^{31}$ are independently of each other $C_1$-$C_{18}$alkyl, $C_6$-$C_{18}$aryl, or $C_6$-$C_{18}$aryl, which is substituted by $C_1$-$C_{18}$alkyl, and $A^{32}$ is $C_1$-$C_{18}$alkyl, $C_6$-$C_{18}$aryl, or $C_6$-$C_{18}$aryl, which is substituted by $C_1$-$C_{18}$alkyl.

Preferably, $A^6$ and $A^7$ are independently of each other H, $C_1$-$C_{18}$alkyl, such as methyl, ethyl, n-propyl, iso-propyl, n-butyl, isobutyl, sec-butyl, t-butyl, 2-methylbutyl, n-pentyl, isopentyl, n-hexyl, 2-ethylhexyl, or n-heptyl, $C_1$-$C_{18}$alkyl which is substituted by E' and/or interrupted by D', such as —CH$_2$OCH$_3$, —CH$_2$OCH$_2$CH$_3$, —CH$_2$OCH$_2$CH$_2$OCH$_3$, or —CH$_2$OCH$_2$CH$_2$OCH$_2$CH$_3$, $C_6$-$C_{24}$aryl, such as phenyl, naphthyl, or biphenyl, $C_6$-$C_{24}$aryl which is substituted by G', such as —C$_6$H$_4$OCH$_3$, —C$_6$H$_4$OCH$_2$CH$_3$, —C$_6$H$_3$(OCH$_3$)$_2$, —C$_6$H$_3$(OCH$_2$CH$_3$)$_2$, —C$_6$H$_4$CH$_3$, —C$_6$H$_3$(CH$_3$)$_2$, —C$_6$H$_2$(CH$_3$)$_3$, or —C$_6$H$_4$tBu.

$A^8$ is preferably H, $C_1$-$C_{18}$alkyl, such as methyl, ethyl, n-propyl, iso-propyl, n-butyl, isobutyl, sec-butyl, t-butyl, 2-methylbutyl, n-pentyl, isopentyl, n-hexyl, 2-ethylhexyl, n-heptyl, or $C_6$-$C_{24}$aryl, such as phenyl, naphthyl, or biphenyl.

Preferably, $A^9$ and $A^{10}$ are independently of each other H, $C_1$-$C_{18}$alkyl, such as n-butyl, sec-butyl, hexyl, octyl, or 2-ethyl-hexyl, $C_1$-$C_{18}$alkyl which is substituted by E' and/or interrupted by D', such as —CH$_2$(OCH$_2$CH$_2$)$_w$OCH$_3$, w=1, 2, 3, or 4, $C_6$-$C_{24}$aryl, such as phenyl, naphthyl, or biphenyl, $C_6$-$C_{24}$aryl which is substituted by G', such as —C$_6$H$_4$OCH$_3$, —C$_6$H$_4$OCH$_2$CH$_3$, —C$_6$H$_3$(OCH$_3$)$_2$, —C$_6$H$_3$(OCH$_2$CH$_3$)$_2$, —C$_6$H$_4$—CH$_3$, —C$_6$H$_3$(CH$_3$)$_2$, —C$_6$H$_2$(CH$_3$)$_3$, or —C$_6$H$_4$tBu, or $A^9$ and $A^{10}$ together form a 4 to 8 membered ring, especially a 5 or 6 membered ring, such as cyclohexyl, or cyclopentyl.

Preferably, $A^{14}$ and $A^{15}$ are independently of each other H, $C_1$-$C_{18}$alkyl, such as methyl, ethyl, n-propyl, iso-propyl, n-butyl, isobutyl, or sec-butyl, or $C_6$-$C_{24}$aryl, such as phenyl, naphthyl, or biphenyl.

D' is preferably —CO—, —COO—, —S—, —SO—, —SO$_2$—, —O—, —NA$^{25}$-, wherein $A^{25}$ is $C_1$-$C_{18}$alkyl, such as methyl, ethyl, n-propyl, iso-propyl, n-butyl, isobutyl, or sec-butyl, or $C_6$-$C_{24}$aryl, such as phenyl, naphthyl, or biphenyl.

E' is preferably —OA$^{29}$; —SA$^{29}$; —NA$^{25}$A$^{25}$; —COA$^{28}$; —COOA$^{27}$; —CONA$^{25}$A$^{25}$; or —CN; wherein $A^{25}$, $A^{27}$, $A^{28}$ and $A^{29}$ are independently of each other $C_1$-$C_{18}$alkyl, such as methyl, ethyl, n-propyl, iso-propyl, n-butyl, isobutyl, sec-butyl, hexyl, octyl, or 2-ethyl-hexyl, or $C_6$-$C_{24}$ aryl, such as phenyl, naphthyl, or biphenyl.

Among the above-mentioned groups M the following groups are preferred:

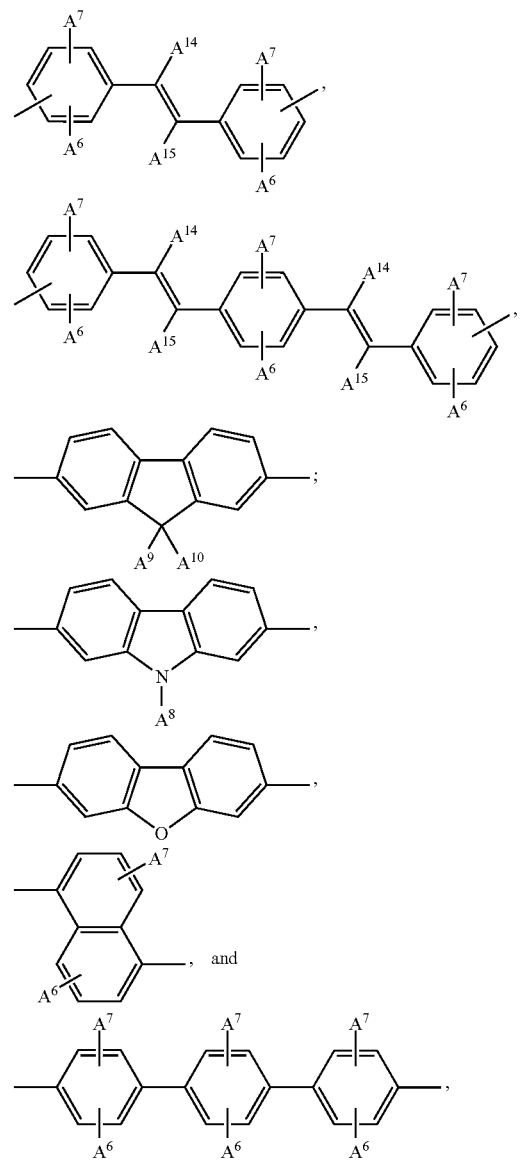

wherein $A^6$, $A^7$, $A^{14}$, $A^{15}$, $A^9$ and $A^{10}$ are as defined above.

Examples of especially preferred groups M are:

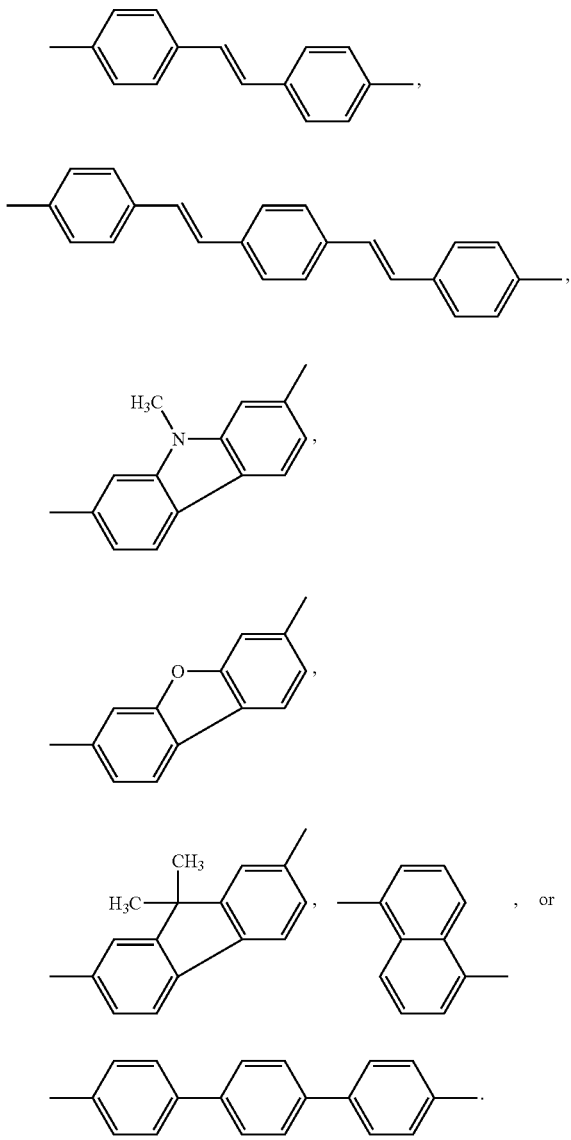

Examples of preferred groups X, Y and W are given below, wherein most preferably X, Y and W are independently of each other a group of formula

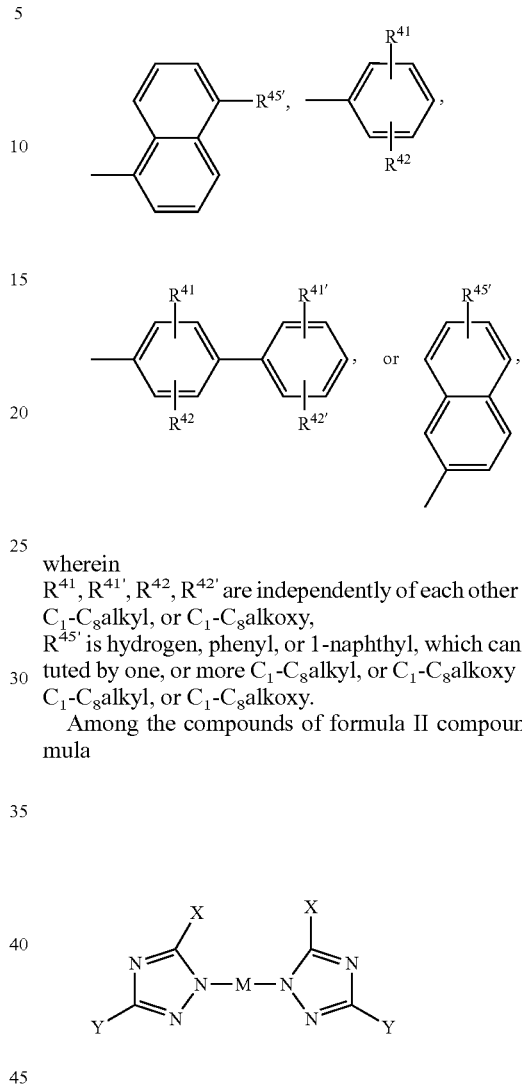

wherein
$R^{41}, R^{41'}, R^{42}, R^{42'}$ are independently of each other hydrogen, $C_1$-$C_8$alkyl, or $C_1$-$C_8$alkoxy,
$R^{45'}$ is hydrogen, phenyl, or 1-naphthyl, which can be substituted by one, or more $C_1$-$C_8$alkyl, or $C_1$-$C_8$alkoxy groups; or $C_1$-$C_8$alkyl, or $C_1$-$C_8$alkoxy.

Among the compounds of formula II compounds of formula $$\text{(IIa)}$$

are more preferred.

Examples of especially preferred compounds are:

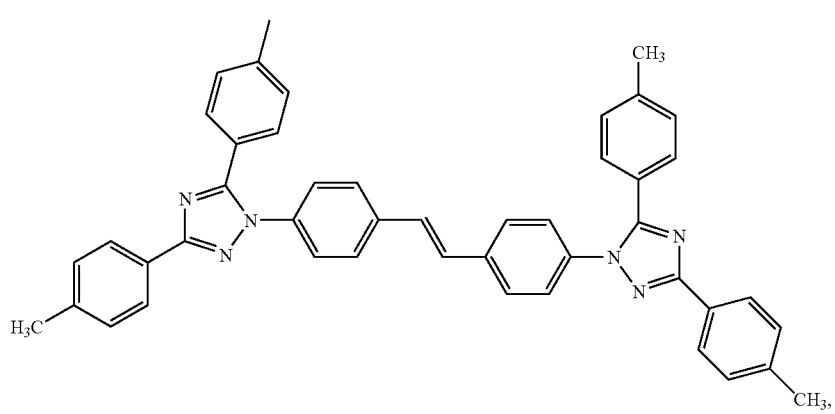

(D-1)

-continued
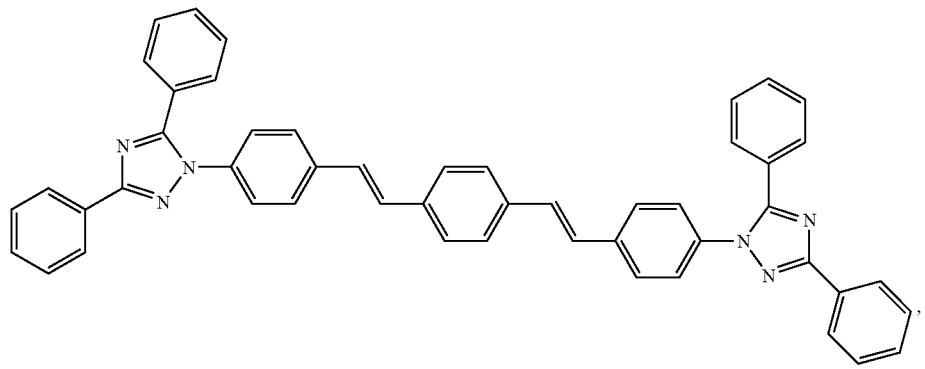
(D-2)
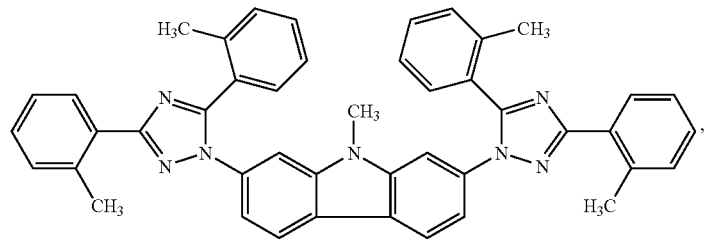
(D-3)
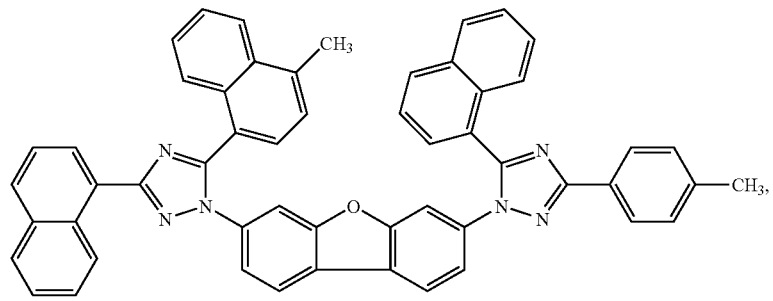
(D-4)
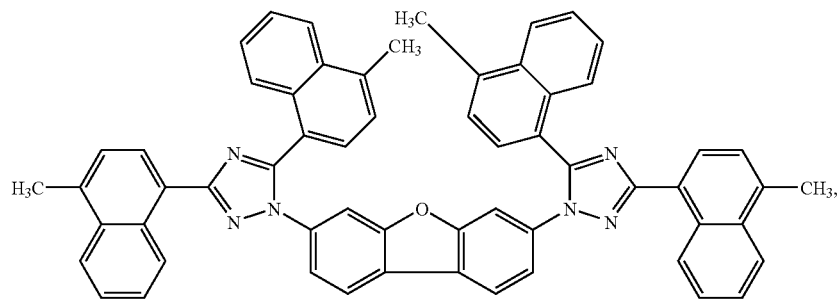
(D-5)

-continued

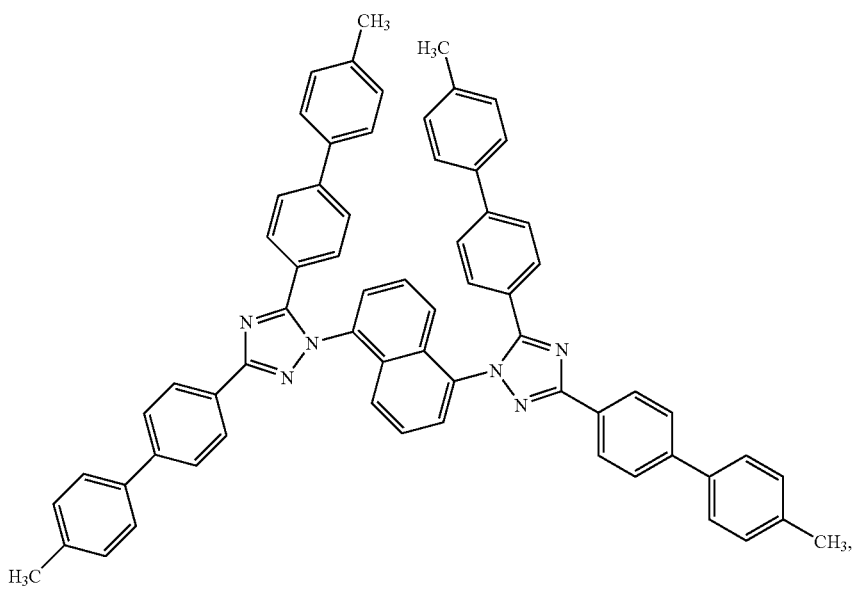

(D-6)

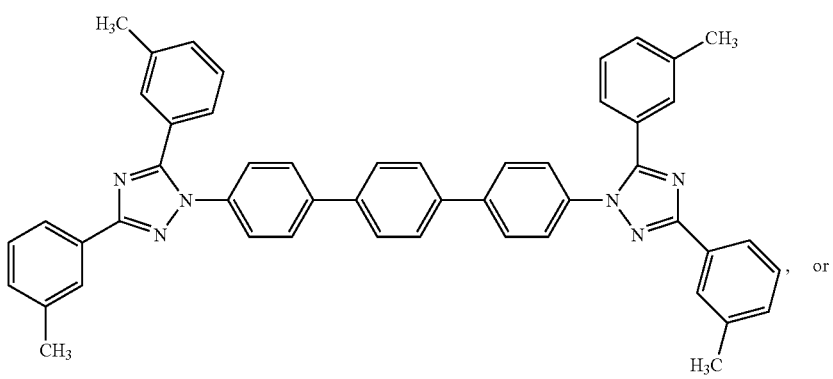

(D-7), or

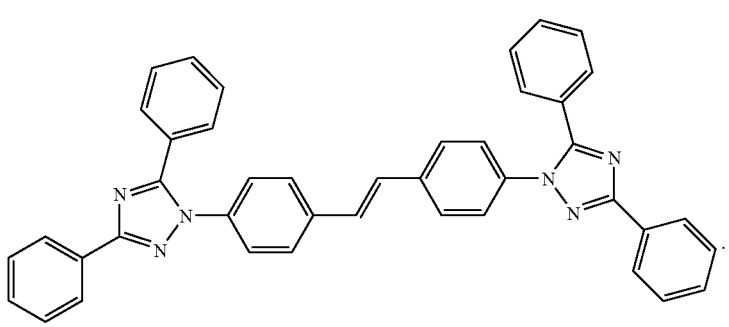

(D-8).

In further preferred embodiment of the present invention at least one of the groups X, Y and W is a polycyclic aryl group, especially pentalenyl, indenyl, azulenyl, naphthyl, biphenylenyl, as-indacenyl, s-indacenyl, acenaphthylenyl, phenanthryl, anthracenyl, fluoranthenyl, acephenanthrylenyl, aceanthrylenyl, triphenylenyl, pyrenyl, chrysenyl, naphthacenyl, picenyl, perylenyl, pentacenyl, pentaphenyl, hexacenyl, or hexaphenyl, which can optionally be substituted by G, wherein G is as defined above. Among the above groups naphthyl, biphenylenyl, phenanthryl, anthracenyl, triphenylenyl and pyrenyl are preferred.

If the triazole is a compound of formula I, it can, in principle be a compound of formula

(Ia)

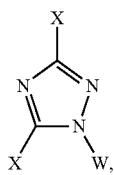 (Ib)
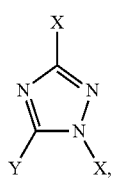 (Ic)
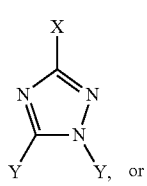 (Id)
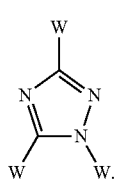 (Ie)
In a further preferred embodiment of the present invention at least one, especially two and very especially all three of the groups X, Y and W are independently of each other a group of the formula $-(W^1)_a-(W^2)_b-W^3$, wherein
a and b are 1, or 1,
$W^1$ and $W^2$ are independently of each other a group of formula
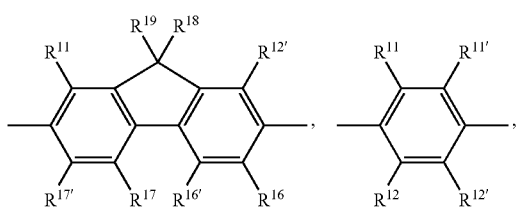
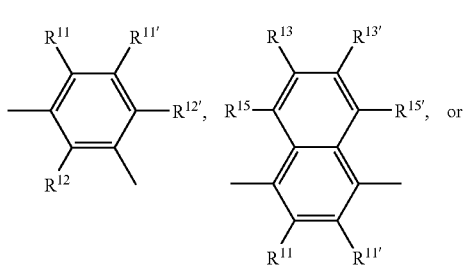
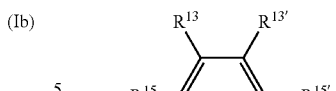
and $W^3$ is a group of formula
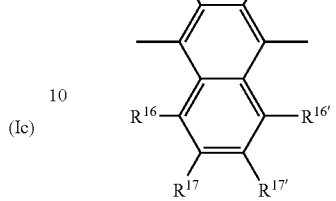
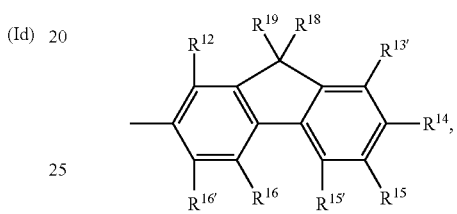
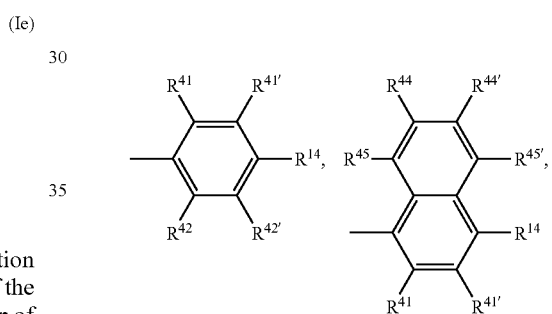
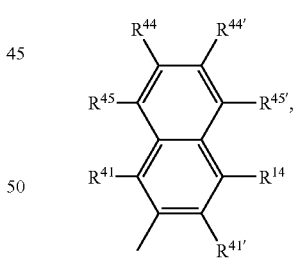
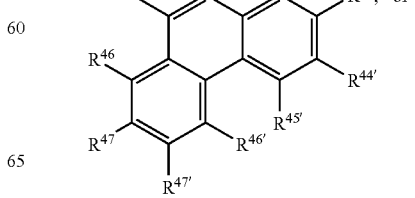

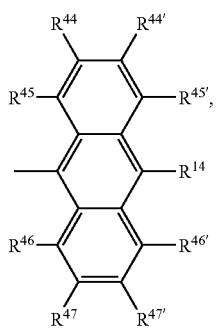

wherein R¹¹, R¹¹', R¹², R¹²', R¹³, R¹³', R¹⁵, R¹⁵', R¹⁶, R¹⁶', R¹⁷, R¹⁷', R⁴¹, R⁴¹', R⁴², R⁴²', R⁴⁴, R⁴⁴', R⁴⁵, R⁴⁵', R⁴⁶, R⁴⁶', R⁴⁷ and R⁴⁷' are independently of each other H, E, $C_6$-$C_{18}$aryl; $C_6$-$C_{18}$aryl which is substituted by G; $C_1$-$C_{18}$alkyl; $C_1$-$C_{18}$alkyl which is substituted by E and/or interrupted by D; $C_1$-$C_{18}$alkoxy; or $C_1$-$C_{18}$alkoxy which is substituted by E and/or interrupted by D; $C_7$-$C_{18}$aralkyl; or $C_7$-$C_{18}$aralkyl which is substituted by G;

R¹⁴ is H, $C_1$-$C_{18}$alkyl; or $C_1$-$C_{18}$alkyl which is substituted by E and/or interrupted by D; $C_1$-$C_{18}$alkoxy; or $C_1$-$C_{18}$alkoxy which is substituted by E and/or interrupted by D;

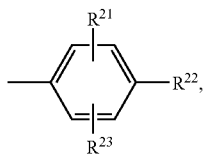

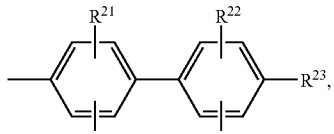

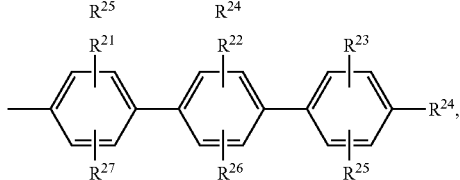

R¹⁸ and R¹⁹ are independently of each other $C_1$-$C_{18}$alkyl; $C_1$-$C_{18}$alkoxy, $C_6$-$C_{18}$aryl; $C_7$-$C_{18}$aralkyl; or R¹⁸ and R¹⁹ together form a ring especially a five- or six-membered ring, which can optionally be substituted by $C_1$-$C_8$alkyl, R²¹, R²², R²³, R²⁴, R²⁵, R²⁶ and R²⁷ are independently of each other H, E, $C_1$-$C_{18}$alkyl; $C_1$-$C_{18}$alkyl which is substituted by E and/or interrupted by D; $C_7$-$C_{18}$aralkyl; $C_7$-$C_{18}$aralkyl which is substituted by G; or W³ is a group of formula

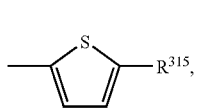
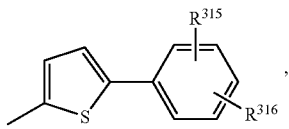

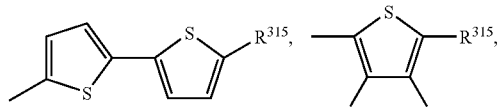

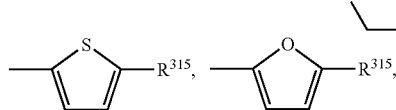

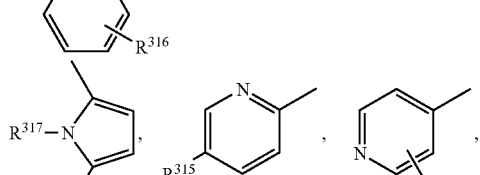

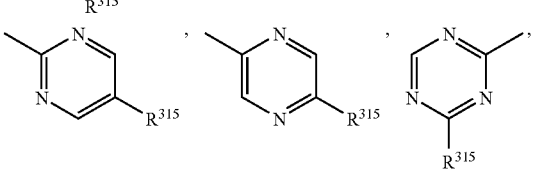

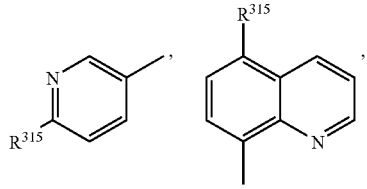

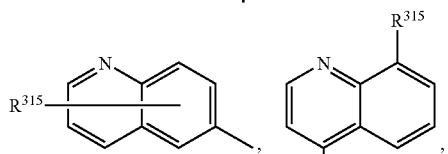

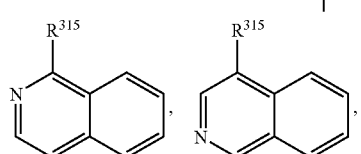

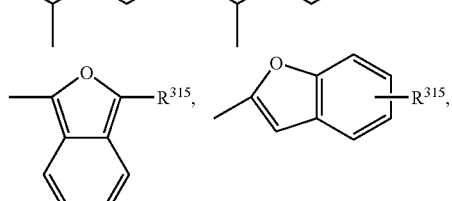

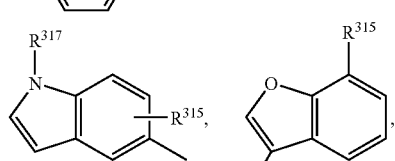

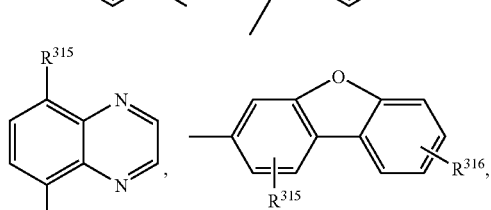

-continued

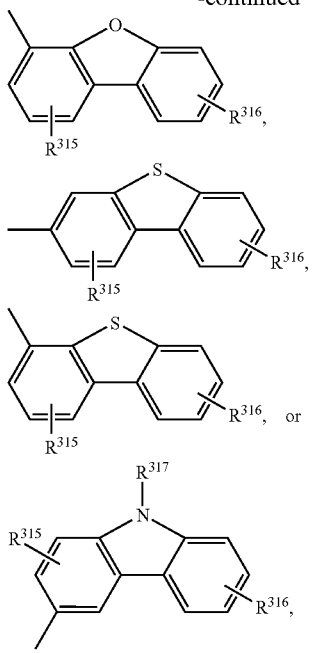

wherein
$R^{315}$ and $R^{316}$ are independently of each other a hydrogen atom, a $C_1$-$C_{18}$alkyl group, a $C_1$-$C_{18}$alkoxy group, a group of formula

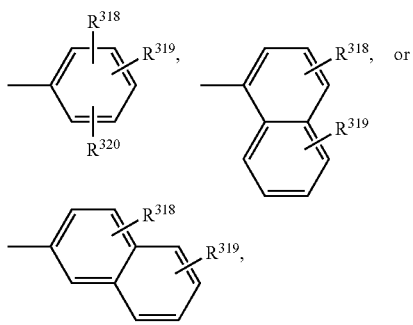

wherein $R^{318}$, $R^{319}$ and $R^{320}$ independently from each other stand for hydrogen, $C_1$-$C_8$-alkyl, $C_1$-$C_8$-alkoxy, or phenyl, and $R^{317}$ stands for is a hydrogen atom, a $C_1$-$C_{25}$alkyl group, which might be interrupted by —O—, a cycloalkyl group, a $C_7$-$C_{18}$aralkyl group, a $C_6$-$C_{18}$aryl group, or a heterocyclic group, which may be substituted by G; wherein D is —CO—, —COO—, —OCOO—, —S—, —SO—, —SO$_2$—, —O—, —NR$^5$—, SiR$^{61}$R$^{62}$—, —POR$^5$—, —CR$^{63}$=CR$^{64}$— or —C≡C—;

E is —OR$^5$, —SR$^5$, —NR$^5$R$^6$, —COR$^8$, —COOR$^7$, —OCOOR$^7$, —CONR$^5$R$^6$, —CN, or halogen;

G is E, or $C_1$-$C_{18}$alkyl; wherein $R^5$ and $R^6$ are independently of each other $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl, or $C_1$-$C_{18}$alkyl which is interrupted by —O—; or $R^5$ and $R^6$ together form a five or six membered ring, in particular

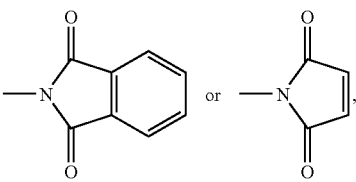

$R^7$ is $C_7$-$C_{12}$alkylaryl; $C_1$-$C_{18}$alkyl; or $C_1$-$C_{18}$alkyl which is interrupted by —O—;

$R^8$ is $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; $C_7$-$C_{12}$alkylaryl, or $C_1$-$C_{18}$alkyl which is interrupted by —O—;

$R^{61}$ and $R^{62}$ are independently of each other $C_6$-$C_{18}$aryl; $C_6$-$C_{18}$aryl which is substituted by $C_1$-$C_{18}$alkyl, or $C_1$-$C_{18}$alkoxy; or $C_1$-$C_{18}$alkyl which is interrupted by —O—, and $R^{63}$ and $R^{64}$ are independently of each other H, $C_6$-$C_{18}$aryl; $C_6$-$C_{18}$aryl which is substituted by $C_1$-$C_{18}$alkyl, $C_1$-$C_{18}$alkoxy; or $C_1$-$C_{18}$alkyl which is interrupted by —O—.

The groups X, Y and W can be different, or the same, or only two of them can be the same.

If $W^3$ is derived from a heteroaromatic group, it is preferably a group of formula

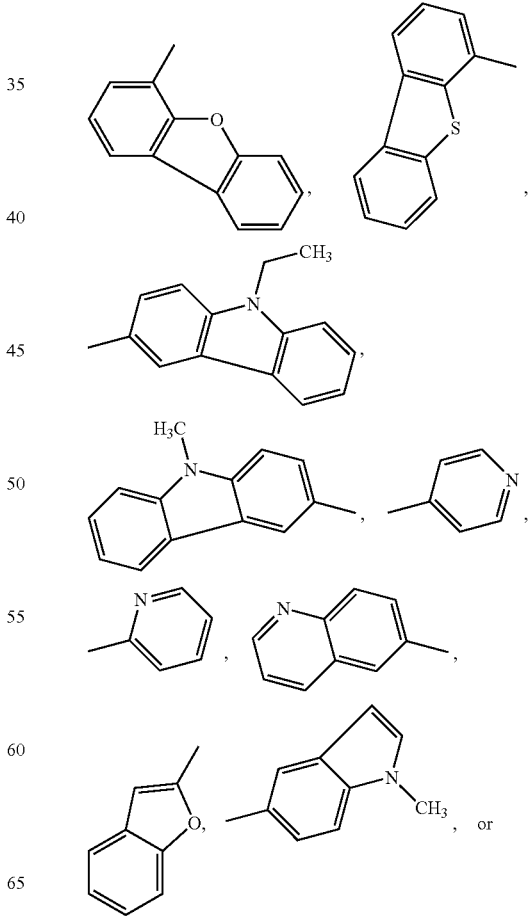

-continued
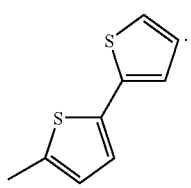
Examples of preferred groups $W^1$ and $W^2$ are
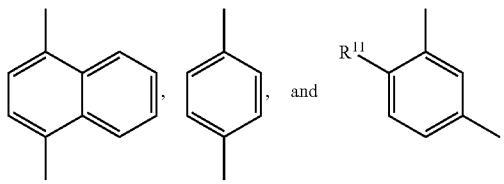
Examples of preferred groups $W^3$ are
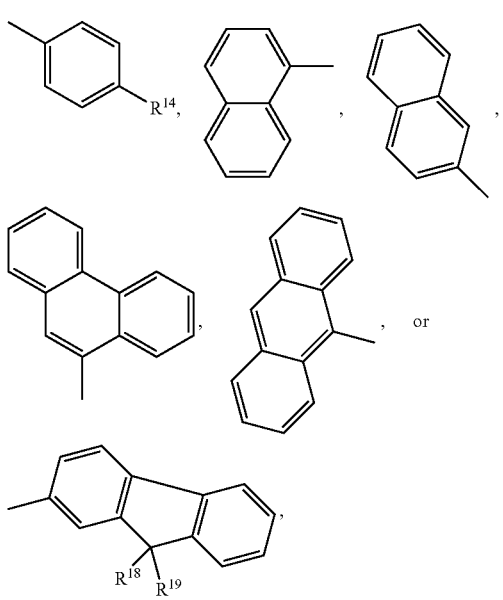
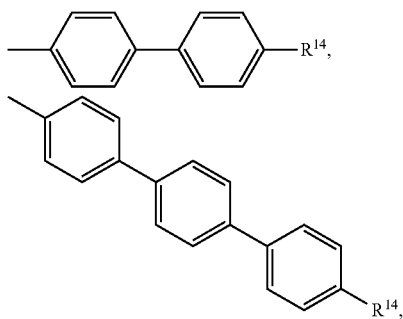
wherein $R^{14}$, $R^{18}$ and $R^{19}$ are independently of each other hydrogen, or $C_1$-$C_8$alkyl.
Examples of preferred groups —$(W^1)_a$—$(W^2)_b$—$W^3$ are
-continued
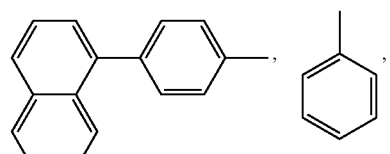
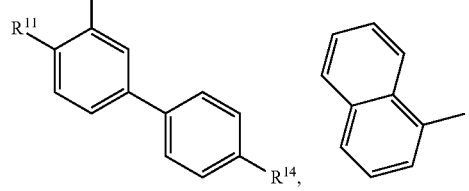
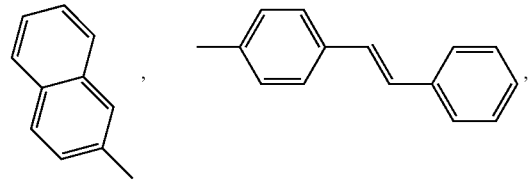
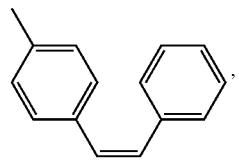
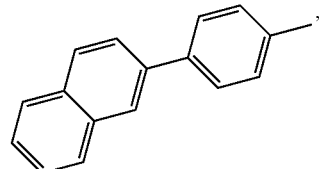
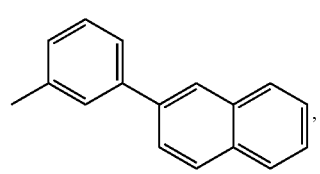
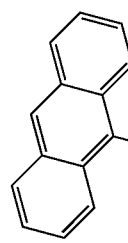
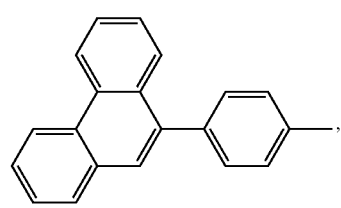

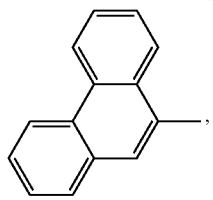
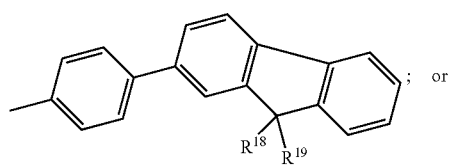
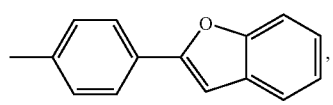
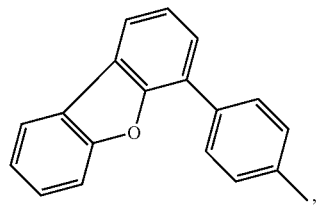
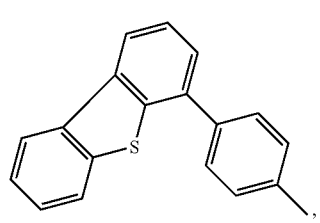
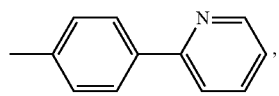
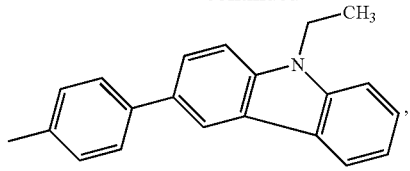
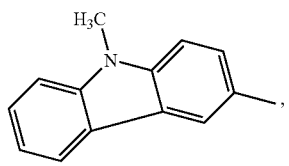
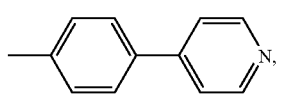
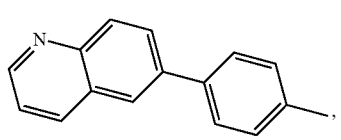
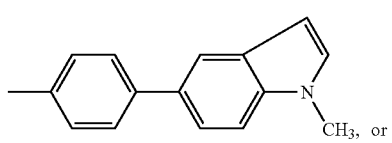
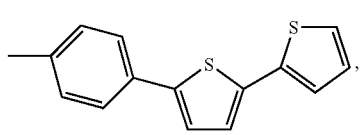
wherein $R^{11}$, $R^{14}$, $R^{18}$ and $R^{19}$ are independently of each other hydrogen, or $C_1$-$C_8$alkyl. $R^{18}$ and $R^{19}$ are preferably $C_1$-$C_8$alkyl.
Examples of especially preferred compounds are given below:

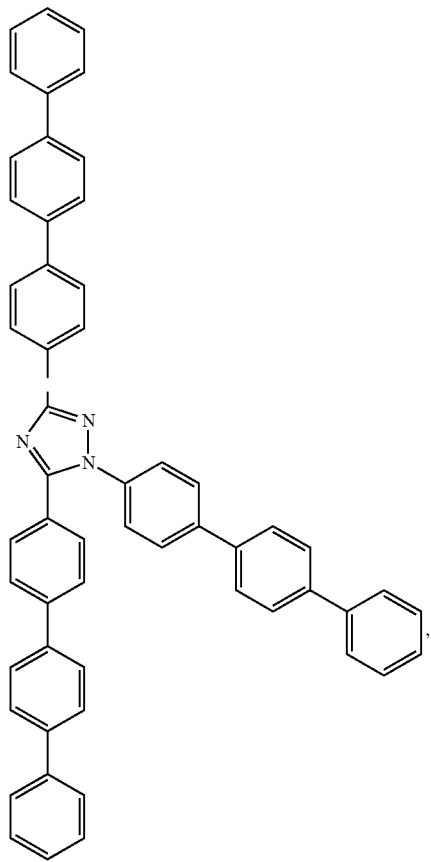
(A-1)
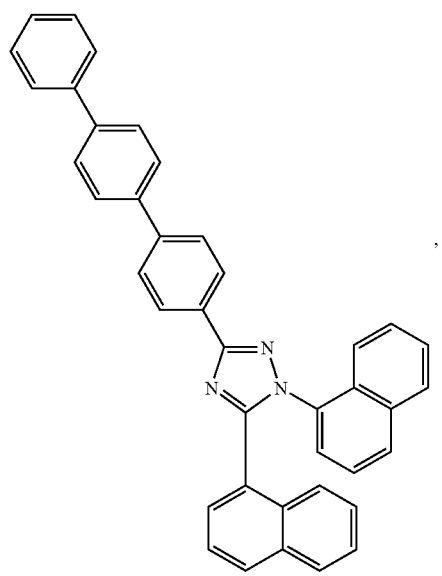
(A-2)
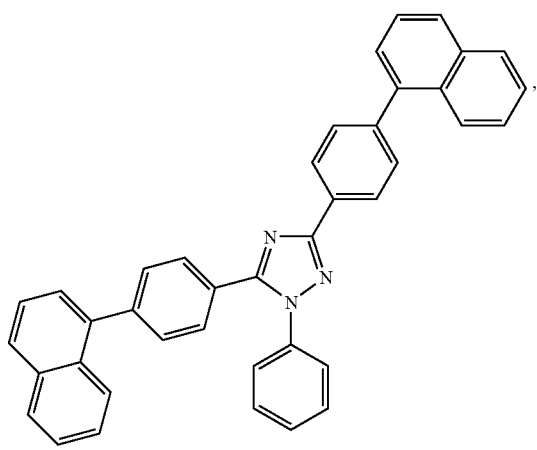
(A-3)

-continued
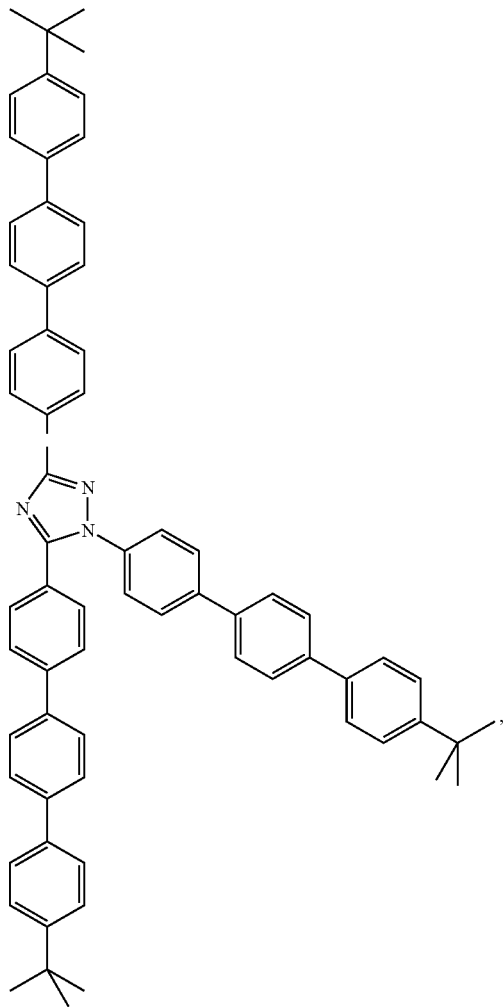
(A-4)
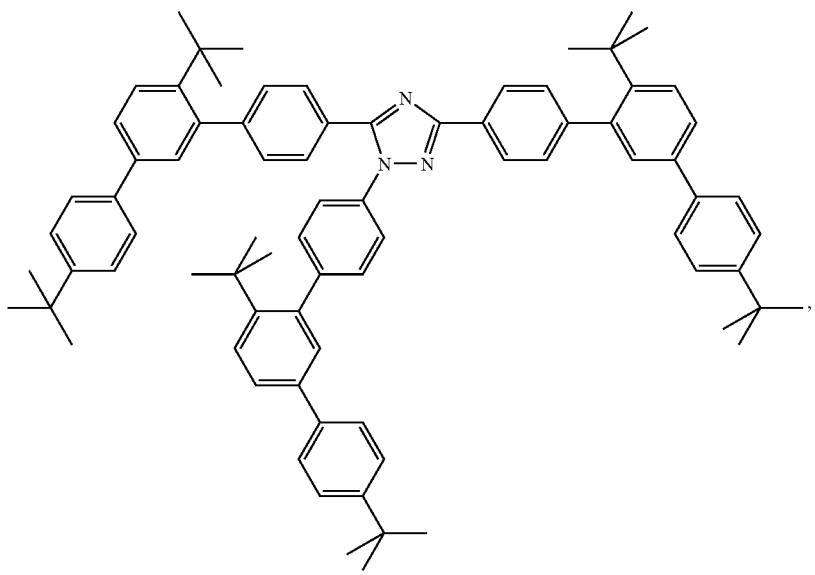
(A-5)

(A-6)
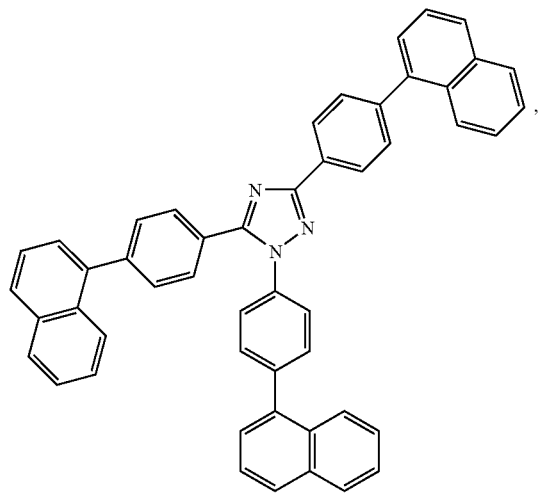
(A-7)
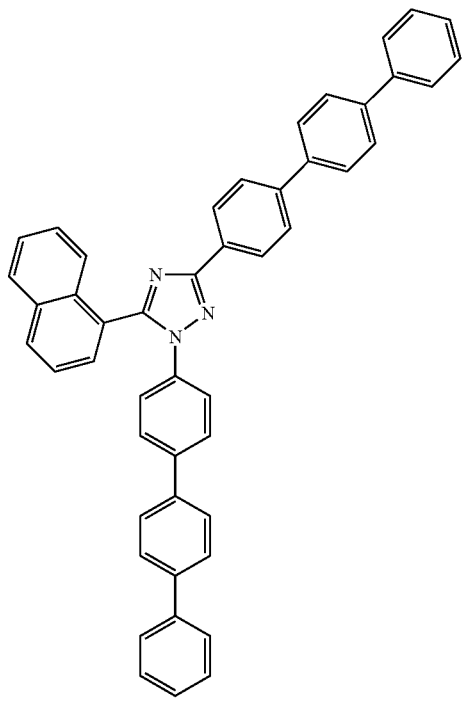
(A-8)
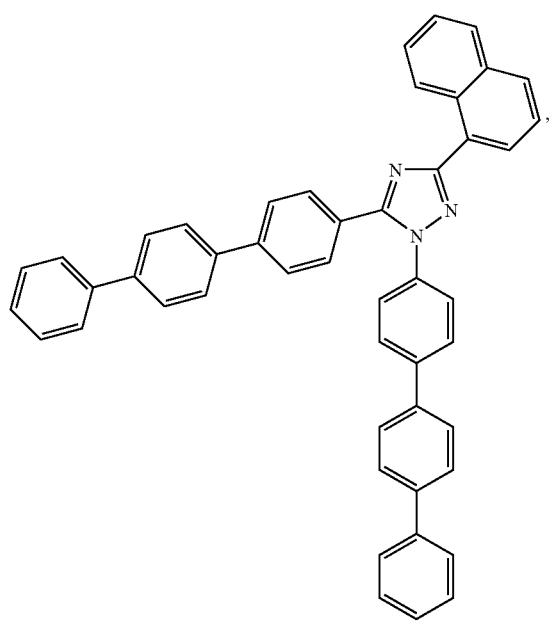
(A-9)
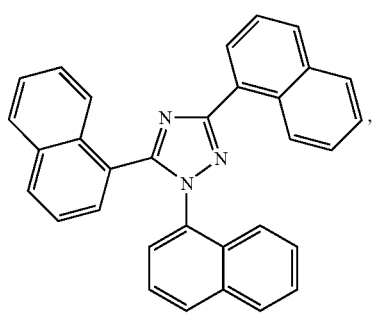

-continued
(A-10)
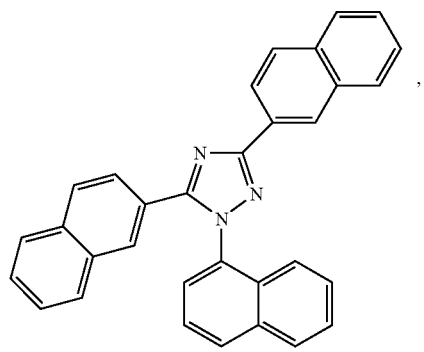
(A-11)
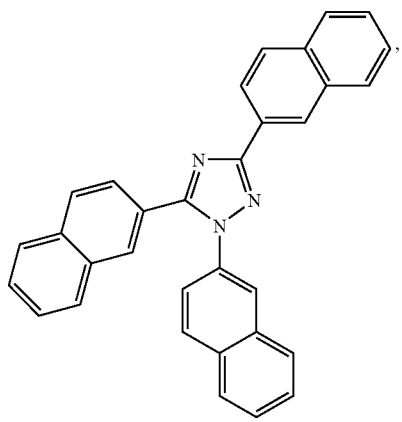
(A-12)
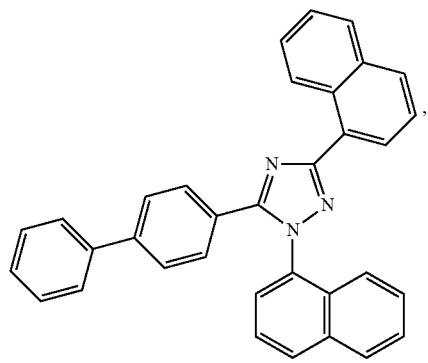
(A-13)
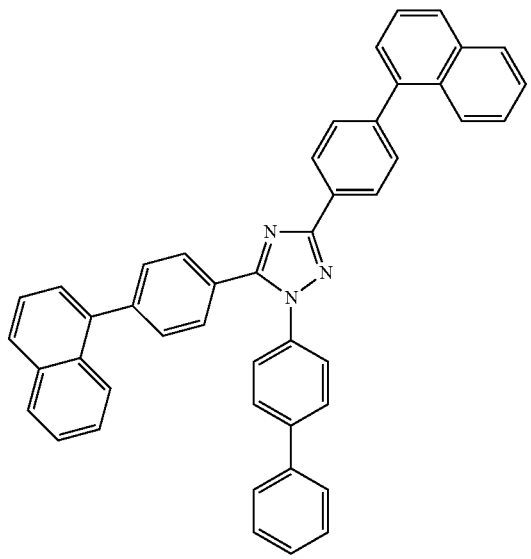
(A-14)
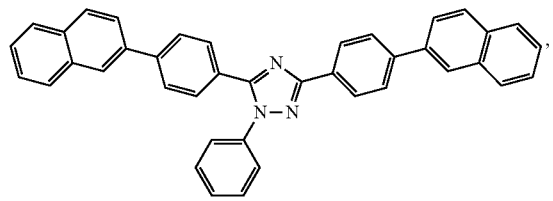
(A-15)
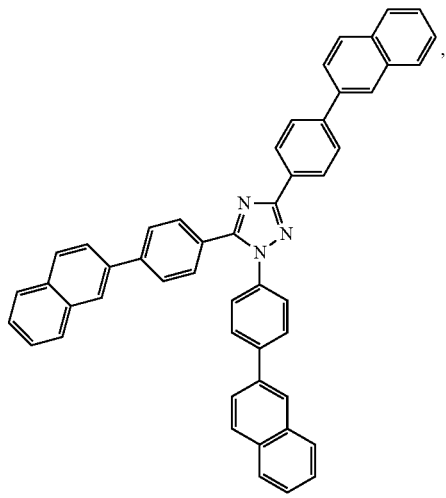

(A-16)
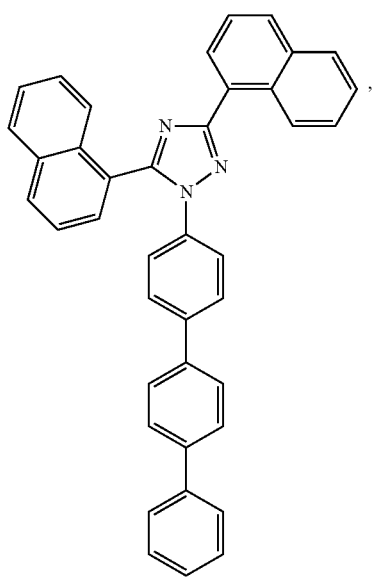
(A-17)
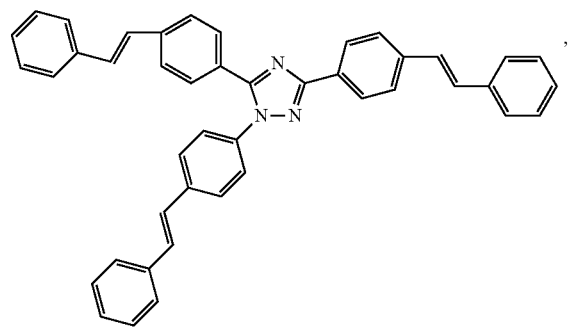
(A-18)
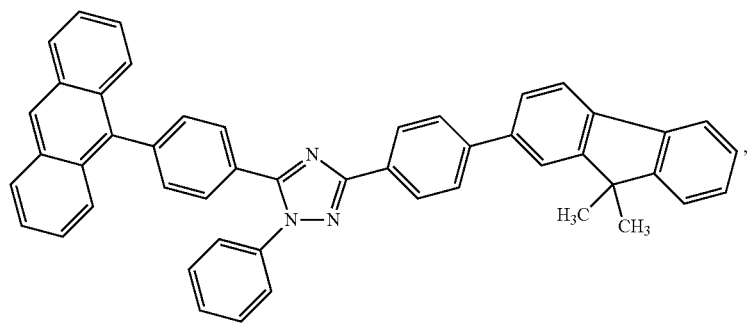
(A-19)
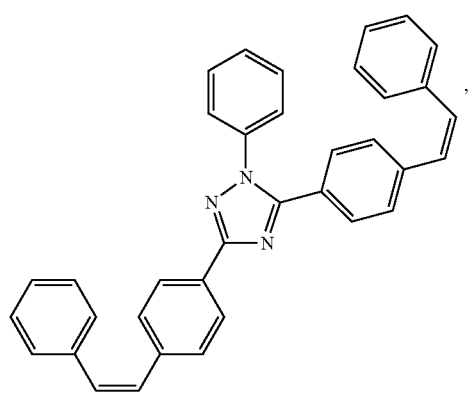
(A-20)
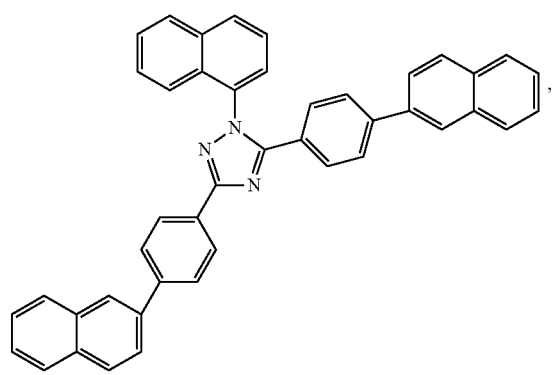

-continued
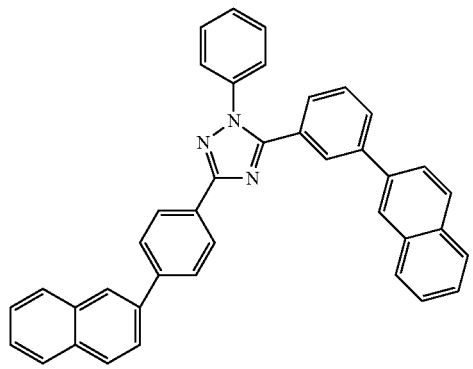
(A-21)
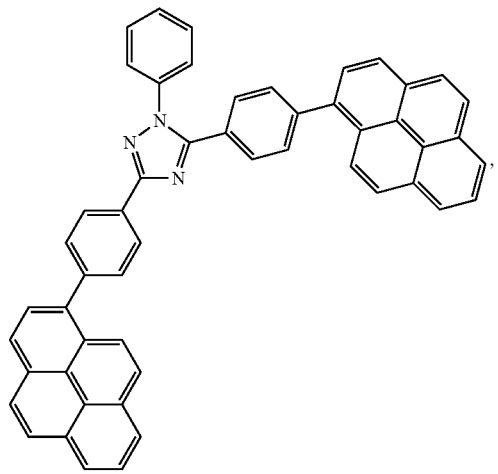
(A-22)
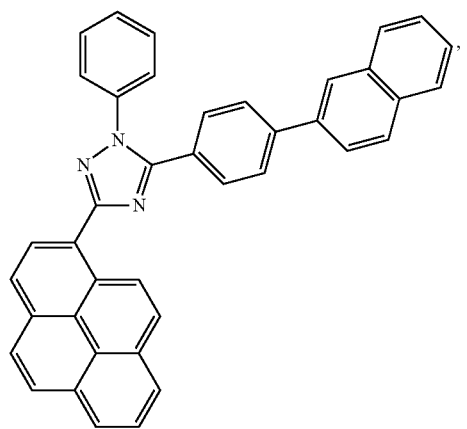
(A-23)
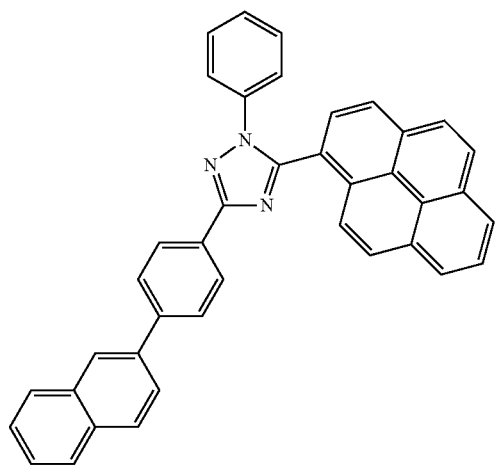
(A-24)
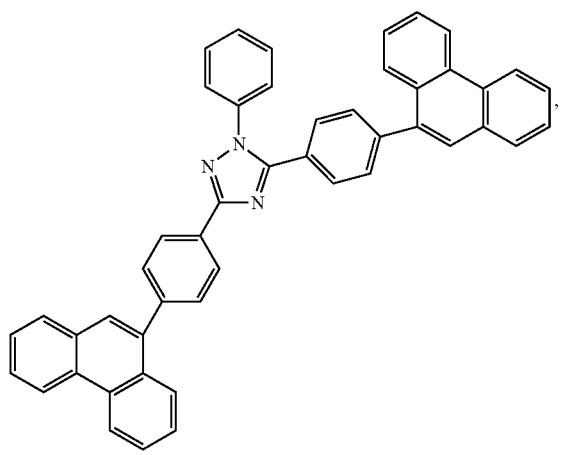
(A-25)
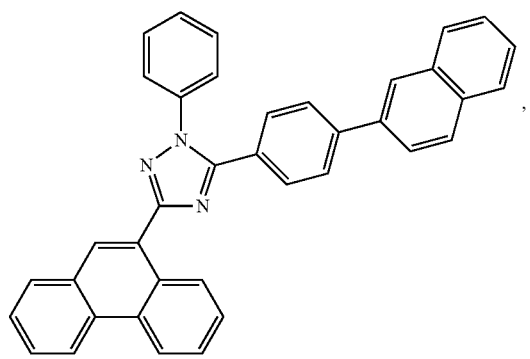
(A-26)

-continued
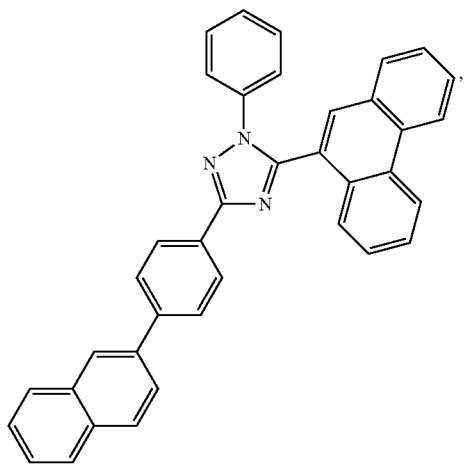
(A-27)
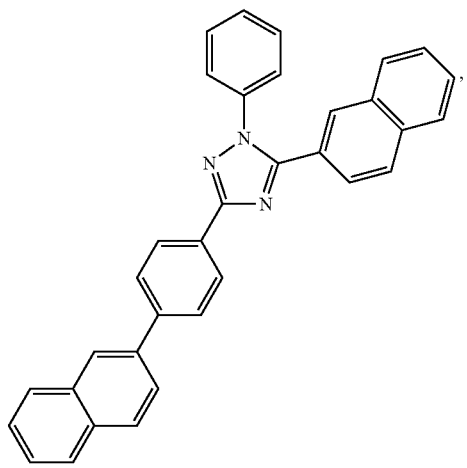
(A-28)
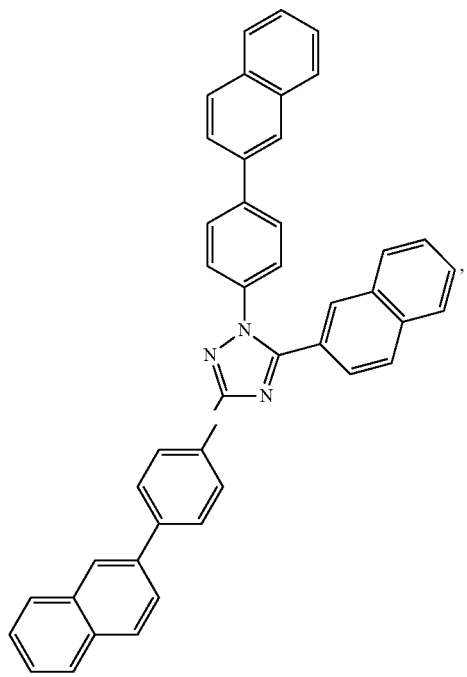
(A-29)
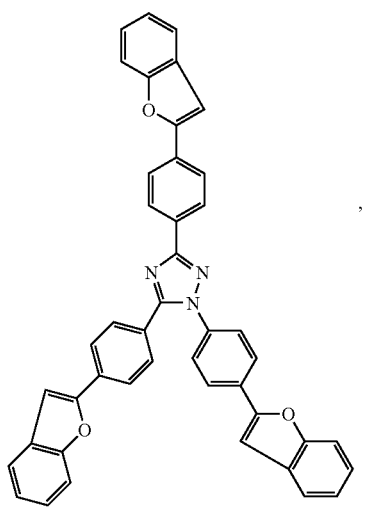
(C-1)

-continued
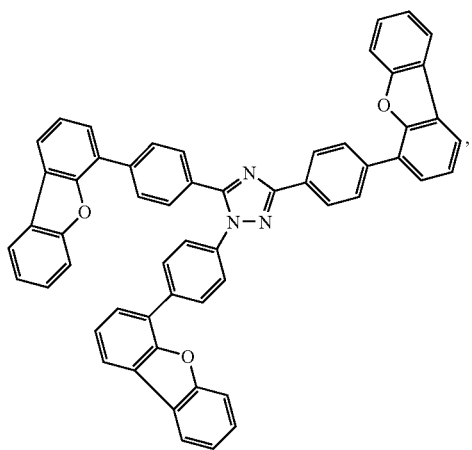
(C-2)
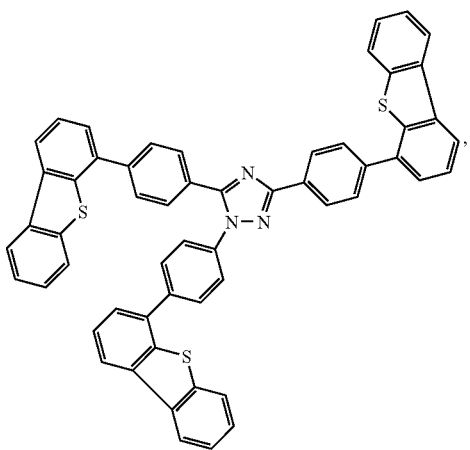
(C-3)
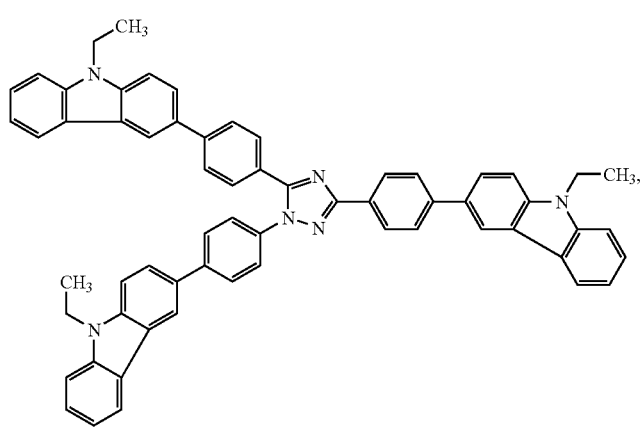
(C-4)
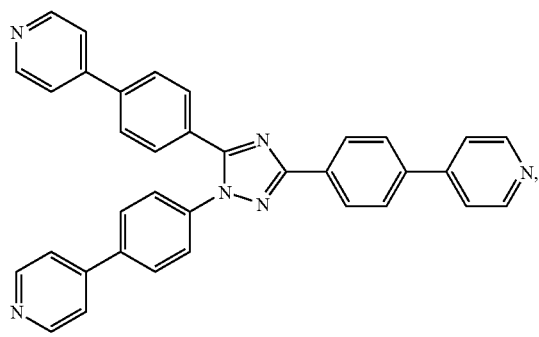
(C-5)
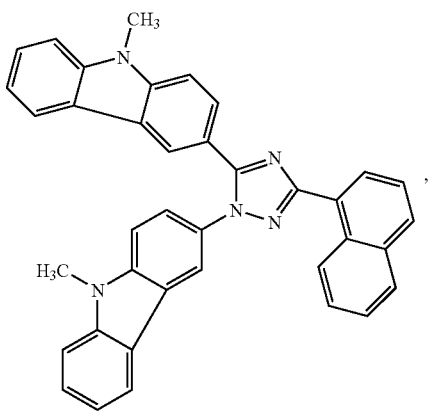
(C-6)

-continued
(C-7)
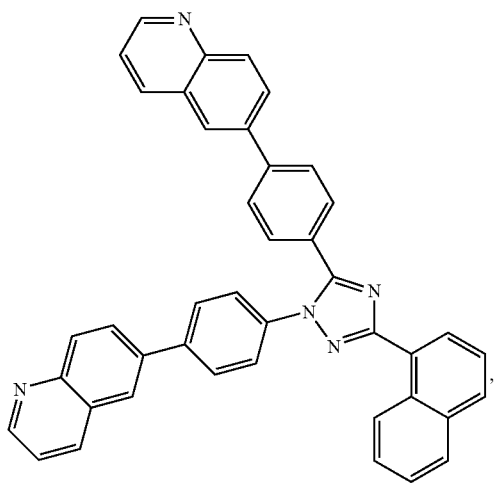
(C-8)
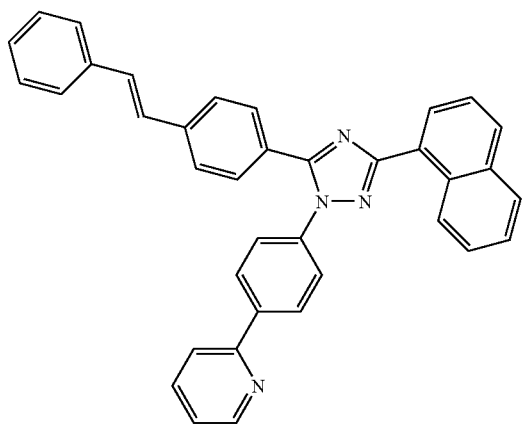
(C-9)
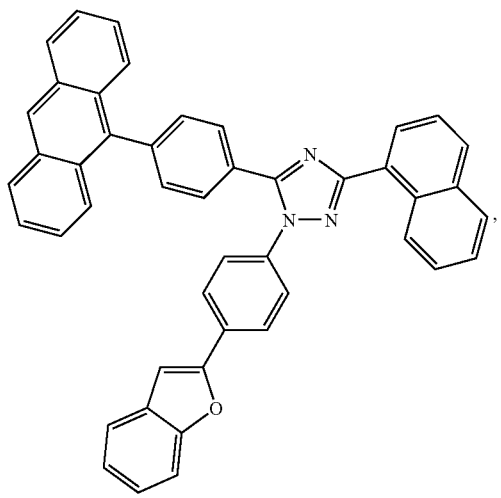
(C-10)
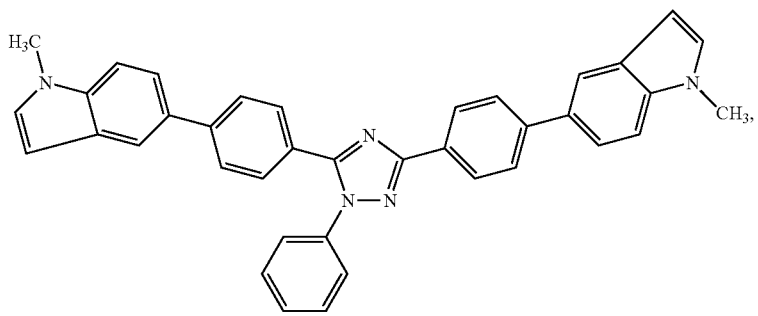
(C-11)
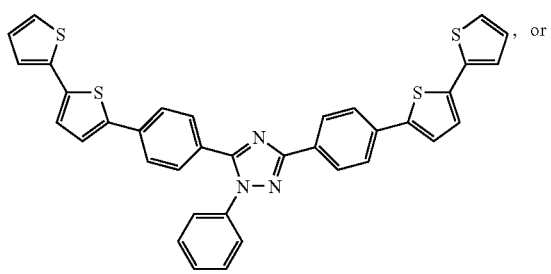, or
(C-12)
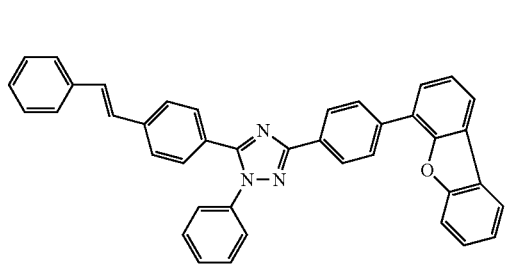

In another preferred embodiment at least one, preferably two, and most preferred all three substituents X, Y and W are independently of each other a group of the formula —$W^1$—$(W^2)_b$—$W^3$, wherein b is 0, or, 1, $W^1$ and $W^2$ are independently of each other a group of formula

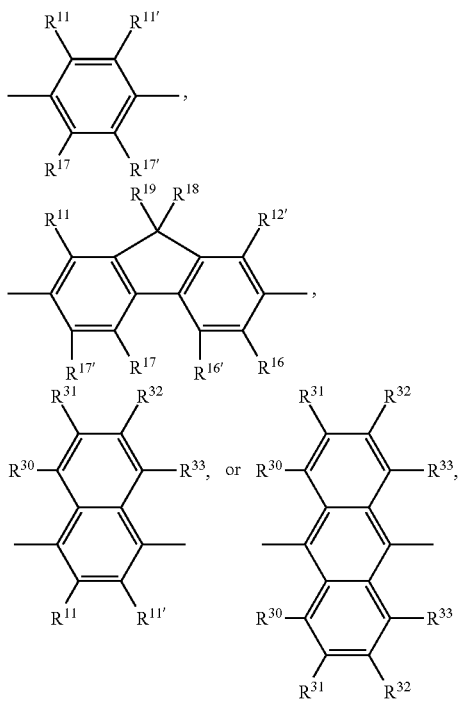

$W^3$ is a group of formula

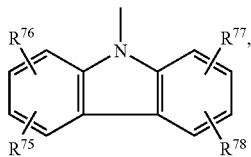

or —$NR^{70}R^{71}$, wherein $R^{70}$ and $R^{71}$ are independently of each other a group of formula

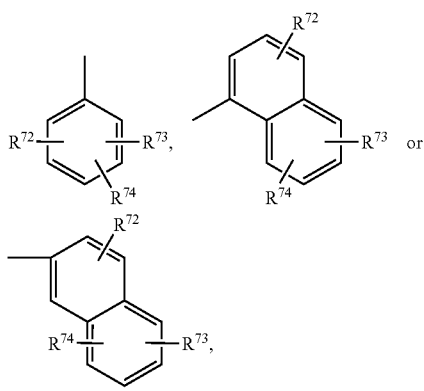

wherein $R^{72}$, $R^{73}$ and $R^{74}$ are independently of each other hydrogen, $C_1$-$C_8$alkyl, a hydroxyl group, a mercapto group, $C_1$-$C_8$alkoxy, $C_1$-$C_8$alkylthio, halogen, halo-$C_1$-$C_8$alkyl, a cyano group, an aldehyde group, a ketone group, a carboxyl group, an ester group, a carbamoyl group, an amino group, a nitro group, a silyl group or a siloxanyl group, $R^{75}$, $R^{76}$, $R^{77}$ and $R^{78}$ are independently of each other H, E, $C_6$-$C_{18}$aryl; $C_6$-$C_{18}$aryl which is substituted by E; $C_1$-$C_{18}$alkyl; $C_1$-$C_{18}$alkyl which is substituted by G and/or interrupted by D; $C_7$-$C_{18}$aralkyl; or $C_7$-$C_{18}$aralkyl which is substituted by E; wherein D, E, G, $R^{11}$, $R^{11'}$, $R^{12'}$, $R^{16}$, $R^{16'}$, $R^{17}$, $R^{17'}$, $R^{30}$, $R^{31}$, $R^{32}$ and $R^{33}$ are as defined in claim 5; or $R^{70}$ and $R^{71}$ together with the nitrogen atom to which they are bonded form a five or six membered heterocyclic ring, such as

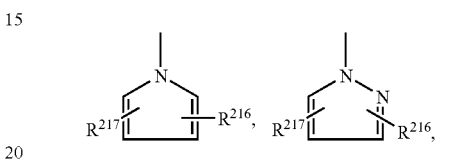

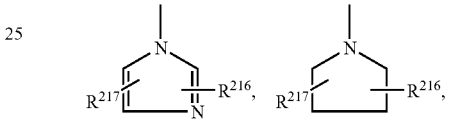

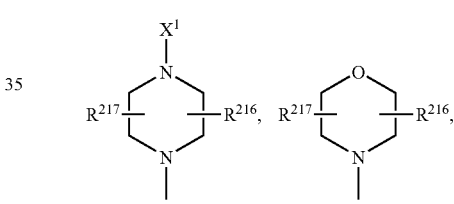

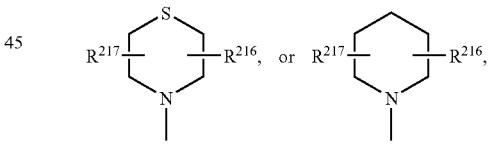

which can be condensed by one or two optionally substituted phenyl groups, such as

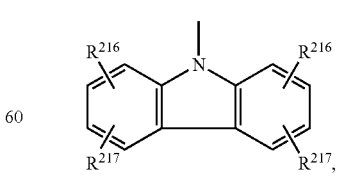

wherein $R^{216}$ and $R^{217}$ independently from each other stands for hydrogen, $C_1$-$C_8$alkyl, $C_1$-$C_8$alkoxy, or phenyl, and $X^1$ stands for hydrogen, or $C_1$-$C_8$alkyl.

In said embodiment compounds of formula I are especially preferred, wherein

X, Y and W are a group of the formula —W$^1$—(W$^2$)$_b$—W$^3$, wherein b is 0, or 1, W$^1$ and W$^2$ are independently of each other a group of formula

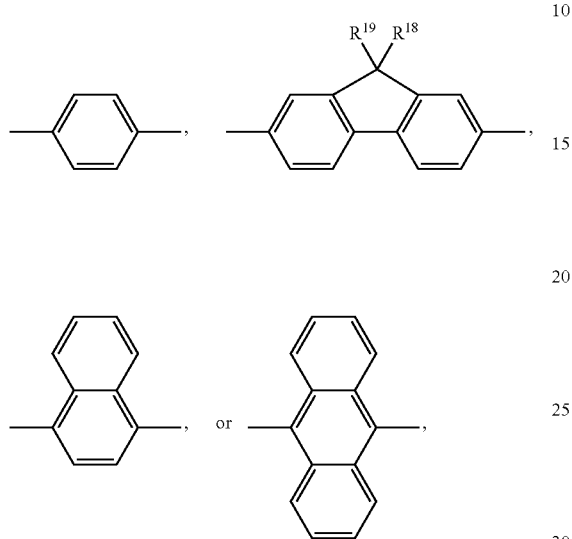

W$^3$ is a group of formula

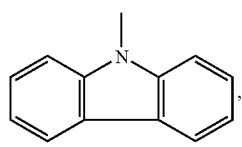

or —NR$^{70}$R$^{71}$, wherein R$^{70}$ and R$^{71}$ are independently of each other a group of formula

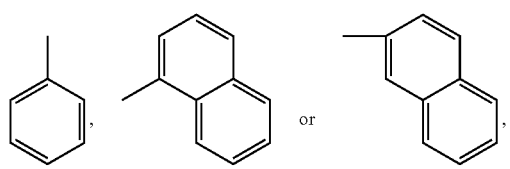

wherein R$^{18}$ and R$^{19}$ are independently of each other C$_1$-C$_{18}$alkyl, or cyclohexyl, or R$^{70}$ and R$^{71}$ together with the nitrogen atom, to which they are bonded, form a group

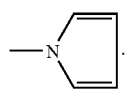

Examples of preferred compounds are given below:

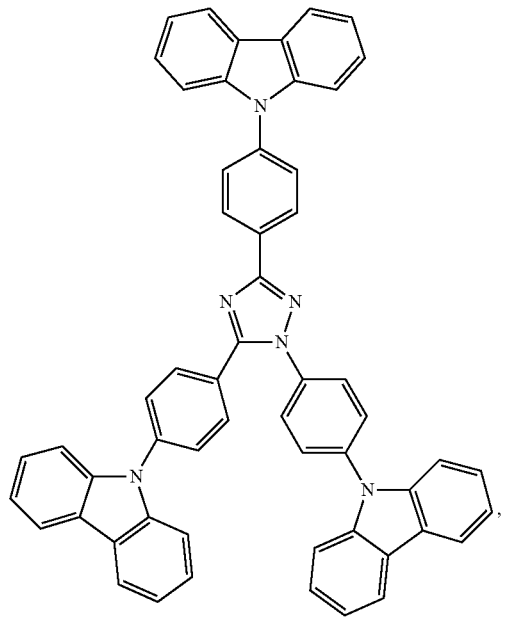

(B-1)

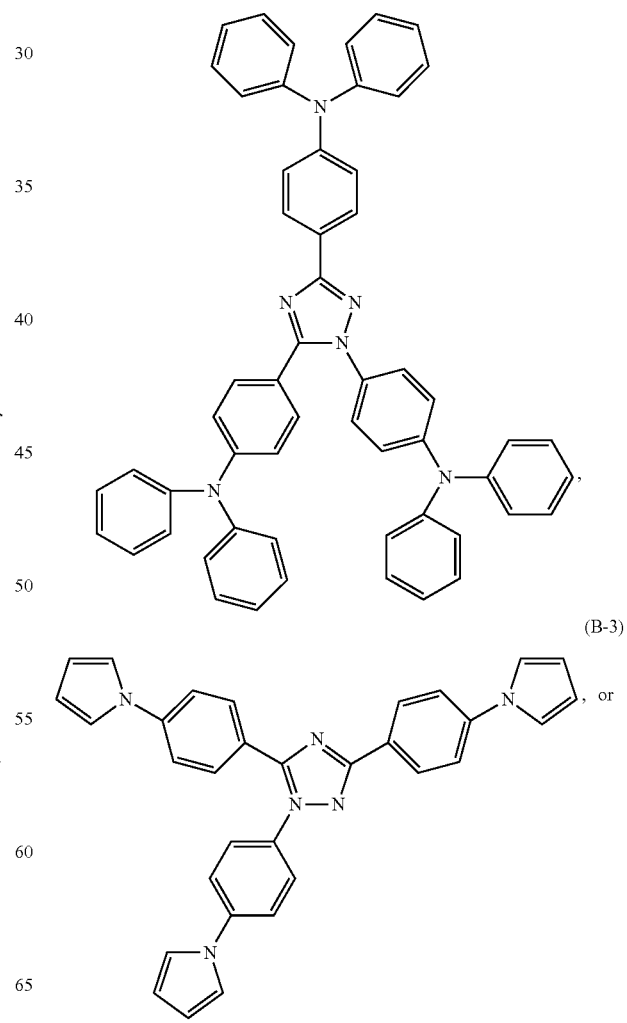

(B-2)

(B-3)

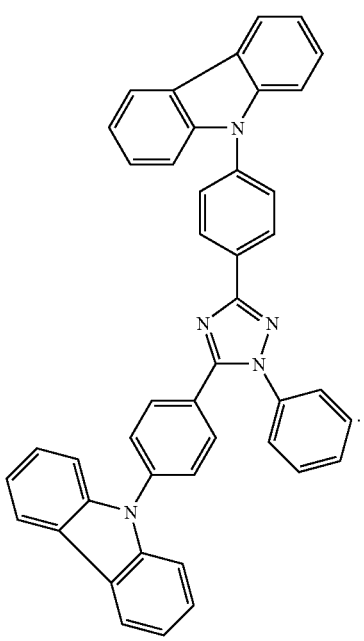

The present triazoles compounds show a high solid state fluorescence in the desired wavelength range and can be prepared according to or analogous to known procedures (see, for example, Letters in Organic chemistry (2004) 231).

The triazole compounds of the present invention of the formula:

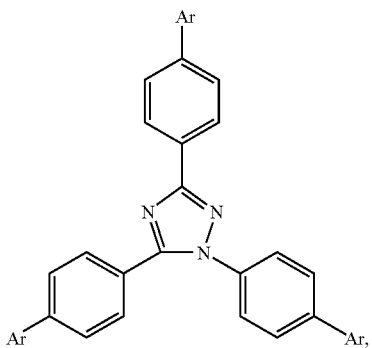

wherein Ar is $W^3$, can, for example, be prepared according to a process, which comprises reacting a derivative of formula

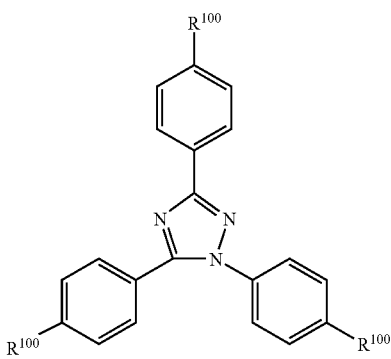

wherein $R^{100}$ stands for halogen such as chloro or bromo, preferably bromo, or E having the meaning of

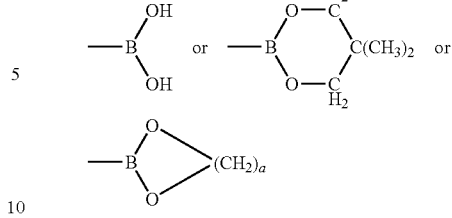 (B-4)

wherein a is 2 or 3,
with boronic acid derivative
E-Ar, or—in case $R^{100}$ is not halogen—Hal-Ar,
wherein Hal stands for halogen, preferably for bromo, in the presence of an allylpalladium catalyst of the μ-halo(triisopropylphosphine)($\eta^3$-allyl)palladium(II) type (see for example WO99/47474).

Accordingly, unsymmetrical substituted triazine compounds of the present invention of the formula:

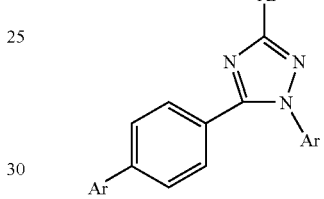

can, for example, be prepared according to a process, which comprises reacting a derivative of formula

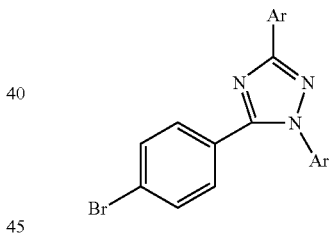

with a boronic acid derivative E-Ar, wherein E is as defined above.

The starting compound

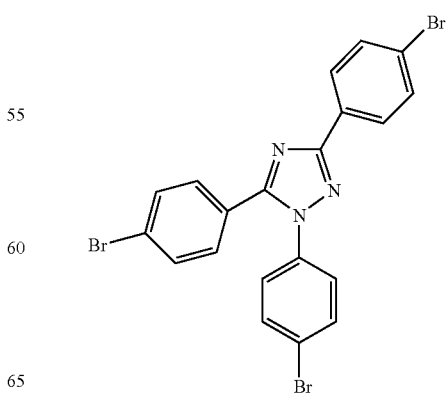

is, for example, available by reacting

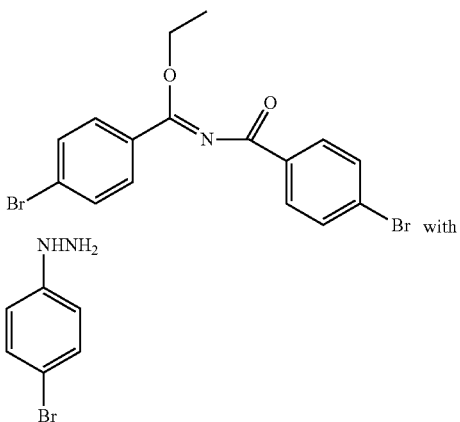

(see, for example, Synthesis (1983) 483).

The starting compound

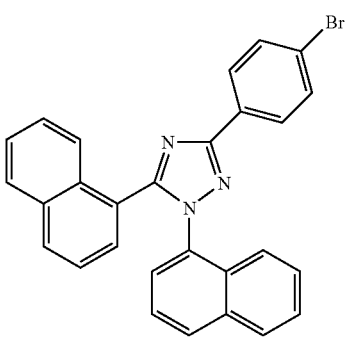 [SMILES: Brc1ccc(-c2nc(-c3cccc4ccccc34)n(-c3cccc4ccccc34)n2)cc1]

is, for example, available by reacting

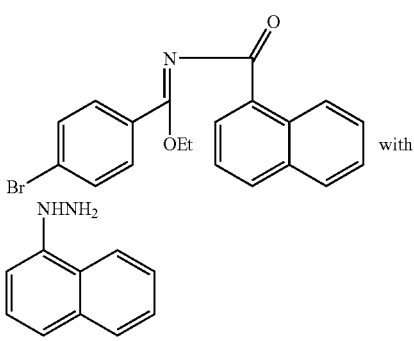

(see, for example, (see, for example, Synthesis (1983) 483).

Preferably, the reaction is carried out in the presence of an organic solvent, such as an aromatic hydrocarbon or a usual polar organic solvent, such as benzene, toluene, xylene, tetrahydrofurane, or dioxane, or mixtures thereof, most preferred toluene. Usually, the amount of the solvent is chosen in the range of from 1 to 10 l per mol of boronic acid derivative. Also preferred, the reaction is carried out under an inert atmosphere such as nitrogen, or argon.

Further, it is preferred to carry out the reaction in the presence of an aqueous base, such as an alkali metal hydroxide or carbonate such as NaOH, KOH, $Na_2CO_3$, $K_2CO_3$, $Cs_2CO_3$ and the like, preferably an aqueous $K_2CO_3$ solution is chosen. Usually, the molar ratio of the base to compound III is chosen in the range of from 0.5:1 to 50:1.

Generally, the reaction temperature is chosen in the range of from 40 to 180° C., preferably under reflux conditions.

Preferred, the reaction time is chosen in the range of from 1 to 80 hours, more preferably from 20 to 72 hours.

In a preferred embodiment a usual catalyst for coupling reactions or for polycondensation reactions is used, preferably Pd-based catalyst such as known tetrakis(triarylphosphonium)-palladium, preferably $(Ph_3P)_4Pd$ and derivatives thereof. Usually, the catalyst is added in a molar ratio from inventive DPP polymer to the catalyst in the range of from 100:1 to 10:1, preferably from 50:1 to 30:1.

Also preferred, the catalyst is added as in solution or suspension. Preferably, an appropriate organic solvent such as the ones described above, preferably benzene, toluene, xylene, THF, dioxane, more preferably toluene, or mixtures thereof, is used. The amount of solvent usually is chosen in the range of from 1 to 10 l per mol of boronic acid derivative.

The obtained inventive polymer can be isolated by well-known methods. Preferably, after cooling down the reaction mixture to room temperature, it is poured into acetone and the obtained precipitation is filtered off, washed and dried.

$C_1$-$C_{18}$Alkyl is a branched or unbranched radical such as for example methyl, ethyl, propyl, isopropyl, n-butyl, sec-butyl, isobutyl, tert-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methylheptyl, n-octyl, 2-ethylhexyl, 1,1,3-trimethylhexyl, 1,1,3,3-tetramethylpentyl, nonyl, decyl, undecyl, 1-methylundecyl, dodecyl, 1,1,3,3,5,5-hexamethylhexyl, tridecyl, tetradecyl, pentadecyl, hexadecyl, heptadecyl, or octadecyl.

$C_1$-$C_{18}$Alkoxy radicals are straight-chain or branched alkoxy radicals, e.g. methoxy, ethoxy, n-propoxy, isopropoxy, n-butoxy, sec-butoxy, tert-butoxy, amyloxy, isoamyloxy or tert-amyloxy, heptyloxy, octyloxy, isooctyloxy, nonyloxy, decyloxy, undecyloxy, dodecyloxy, tetradecyloxy, pentadecyloxy, hexadecyloxy, heptadecyloxy and octadecyloxy.

$C_2$-$C_{18}$Alkenyl radicals are straight-chain or branched alkenyl radicals, such as e.g. vinyl, allyl, methallyl, isopropenyl, 2-butenyl, 3-butenyl, isobutenyl, n-penta-2,4-dienyl, 3-methyl-but-2-enyl, n-oct-2-enyl, n-dodec-2-enyl, isododecenyl, n-dodec-2-enyl or n-octadec-4-enyl.

$C_{2-24}$Alkynyl is straight-chain or branched and preferably $C_{2-8}$alkynyl, which may be unsubstituted or substituted, such as, for example, ethynyl, 1-propyn-3-yl, 1-butyn-4-yl, 1-pentyn-5-yl, 2-methyl-3-butyn-2-yl, 1,4-pentadiyn-3-yl, 1,3-pentadiyn-5-yl, 1-hexyn-6-yl, cis-3-methyl-2-penten-4-yn-1-yl, trans-3-methyl-2-penten-4-yn-1-yl, 1,3-hexadiyn-5-yl, 1-octyn-8-yl, 1-nonyn-9-yl, 1-decyn-10-yl or 1-tetracosyn-24-yl, $C_4$-$C_{18}$cycloalkyl is preferably $C_5$-$C_{12}$cycloalkyl, such as, for example, cyclopentyl, cyclohexyl, cycloheptyl, cyclooctyl, cyclononyl, cyclodecyl, cyclododecyl. Cyclohexyl and cyclododecyl are most preferred.

The term "aryl group" is typically $C_6$-$C_{30}$aryl, such as phenyl, indenyl, azulenyl, naphthyl, biphenyl, terphenylyl or quadphenylyl, as-indacenyl, s-indacenyl, acenaphthylenyl, phenanthryl, fluoranthenyl, triphenlenyl, chrysenyl, naphthacen, picenyl, perylenyl, pentaphenyl, hexacenyl, pyrenyl, or anthracenyl, preferably phenyl, 1-naphthyl, 2-naphthyl, 9-phenanthryl, 2- or 9-fluorenyl, 3- or 4-biphenyl, which may be unsubstituted or substituted. Examples of $C_6$-$C_{18}$aryl are phenyl, 1-naphthyl, 2-naphthyl, 3- or 4-biphenyl, 9-phenanthryl, 2- or 9-fluorenyl, which may be unsubstituted or substituted.

$C_7$-$C_{24}$aralkyl radicals are preferably $C_7$-$C_{18}$aralkyl radicals, which may be substituted, such as, for example, benzyl, 2-benzyl-2-propyl, β-phenyl-ethyl, α,α-dimethyl benzyl, ω-phenyl-butyl, ω,ω-dimethyl-ω-phenyl-butyl, ω-phenyl-dodecyl, ω-phenyl-octadecyl, ω-phenyl-eicosyl or ω-phenyl-docosyl, preferably $C_7$-$C_{18}$aralkyl such as benzyl, 2-benzyl-2-propyl, β-phenyl-ethyl, α,α-dimethylbenzyl, ω-phenyl-butyl, ω,ω-dimethyl-ω-phenyl-butyl, ω-phenyl-dodecyl or ω-phenyl-octadecyl, and particularly preferred $C_7$-$C_{12}$aralkyl such as benzyl, 2-benzyl-2-propyl, β-phenyl-ethyl, α,α-dimethyl benzyl, ω-phenyl-butyl, or ω,ω-dimethyl-ω-phenyl-butyl, in which both the aliphatic hydrocarbon group and aromatic hydrocarbon group may be unsubstituted or substituted.

$C_7$-$C_{12}$alkylaryl is, for example, a phenyl group substituted with one, two or three $C_1$-$C_6$alkyl groups, such as, for example, 2-, 3-, or 4-methylphenyl, 2-, 3-, or 4-ethylphenyl, 3-, or 4-isopropylphenyl, 3,4-dimethylphenyl, 3,5-dimethylphenyl, or 3,4,5-trimethylphenyl.

The term "heteroaryl group", especially $C_2$-$C_{30}$heteroaryl, is a ring, or ring system, wherein nitrogen, oxygen or sulfur are the possible hetero atoms, and is typically an unsaturated heterocyclic radical with five to 18 atoms having at least six conjugated π-electrons such as thienyl, benzo[b]thienyl, dibenzo[b,d]thienyl, thianthrenyl, furyl, furfuryl, 2H-pyranyl, benzofuranyl, isobenzofuranyl, 2H-chromenyl, xanthenyl, dibenzofuranyl, phenoxythienyl, pyrrolyl, imidazolyl, pyrazolyl, pyridyl, bipyridyl, triazinyl, pyrimidinyl, pyrazinyl, 1H-pyrrolizinyl, isoindolyl, pyridazinyl, indolizinyl, isoindolyl, indolyl, 3H-indolyl, phthalazinyl, naphthyridinyl, quinoxalinyl, quinazolinyl, cinnolinyl, indazolyl, purinyl, quinolizinyl, chinolyl, isochinolyl, phthalazinyl, naphthyridinyl, chinoxalinyl, chinazolinyl, cinnolinyl, pteridinyl, carbazolyl, 4aH-carbazolyl, carbolinyl, benzotriazolyl, benzoxazolyl, phenanthridinyl, acridinyl, perimidinyl, phenanthrolinyl, phenazinyl, isothiazolyl, phenothiazinyl, isoxazolyl, furazanyl or phenoxazinyl, preferably the above-mentioned mono- or bicyclic heterocyclic radicals, which may be unsubstituted or substituted.

Halogen is fluorine, chlorine, bromine and iodine.

The terms "haloalkyl" mean groups given by partially or wholly substituting the above-mentioned alkyl group, with halogen, such as trifluoromethyl etc. The "aldehyde group, ketone group, ester group, carbamoyl group and amino group" include those substituted by an alkyl group, a cycloalkyl group, an aryl group, an aralkyl group or a heterocyclic group, wherein the alkyl group, the cycloalkyl group, the aryl group, the aralkyl group and the heterocyclic group may be unsubstituted or substituted. The term "silyl group" means a group of formula —$SiR^{62}R^{63}R^{64}$, wherein $R^{62}$, $R^{63}$ and $R^{64}$ are independently of each other a $C_1$-$C_8$alkyl group, in particular a $C_1$-$C_4$ alkyl group, a $C_6$-$C_{24}$aryl group or a $C_7$-$C_{12}$aralkyl group, such as a trimethylsilyl group. The term "siloxanyl group" means a group of formula —O—$SiR^{62}R^{63}R^{64}$, wherein $R^{62}$, $R^{63}$ and $R^{64}$ are as defined above, such as a trimethylsiloxanyl group.

Possible substituents of the above-mentioned groups are $C_1$-$C_8$alkyl, a hydroxyl group, a mercapto group, $C_1$-$C_8$alkoxy, $C_1$-$C_8$alkylthio, halogen, halo-$C_1$-$C_8$alkyl, a cyano group, an aldehyde group, a ketone group, a carboxyl group, an ester group, a carbamoyl group, an amino group, a nitro group or a silyl group.

As described above, the aforementioned radicals may be substituted by E and/or, if desired, interrupted by D. Interruptions are of course possible only in the case of radicals containing at least 2 carbon atoms connected to one another by single bonds; $C_6$-$C_{18}$aryl is not interrupted; interrupted arylalkyl or alkylaryl contains the unit D in the alkyl moiety. $C_1$-$C_{18}$alkyl substituted by one or more E and/or interrupted by one or more units D is, for example, $(CH_2CH_2O)_n$—$R^x$, where n is a number from the range 1-9 and $R^x$ is H or $C_1$-$C_{10}$alkyl or $C_2$-$C_{10}$alkanoyl (e.g. CO—CH($C_2H_5$)$C_4H_9$), $CH_2$—$CH(OR^{y'})$—$CH_2$—O—$R^y$, where $R^y$ is $C_1$-$C_{18}$alkyl, $C_5$-$C_{12}$cycloalkyl, phenyl, $C_7$-$C_{15}$-phenylalkyl, and $R^{y'}$ embraces the same definitions as $R^y$ or is H; $C_1$-$C_8$alkylene-COO—$R^z$, e.g. $CH_2COOR^z$, $CH(CH_3)COOR^z$, $C(CH_3)_2CO$-$OR^z$, where $R^z$ is H, $C_1$-$C_{18}$alkyl, $(CH_2CH_2O)_{1-9}$—$R^x$, and $R^x$ embraces the definitions indicated above; $CH_2CH_2$—O—CO—CH=$CH_2$; $CH_2CH(OH)CH_2$—O—CO—$C(CH_3)$=$CH_2$.

The electroluminescent devices may be employed for full color display panels in, for example, mobile phones, televisions and personal computer screens.

The electroluminescent devices of the present invention are otherwise designed as is known in the art, for example as described in U.S. Pat. Nos. 5,518,824, 6,225,467, 6,280,859, 5,629,389, 5,486,406, 5,104,740, 5,116,708 and 6,057,048, the relevant disclosures of which are hereby incorporated by reference.

For example, organic EL devices contain one or more layers such as:
substrate; base electrode; hole-injecting layer; hole transporting layer; emitter layer; electron-transporting layer; electron-injecting layer; top electrode; contacts and encapsulation.

This structure is a general case and may have additional layers or may be simplified by omitting layers so that one layer performs a plurality of tasks. For instance, the simplest organic EL device consists of two electrodes which sandwich an organic layer that performs all functions, including the function of light emission.

A preferred EL device comprises in this order:
(a) an anode,
(b) a hole injecting layer and/or a hole transporting layer,
(c) a light-emitting layer,
(d) optionally an electron transporting layer and
(e) a cathode.

The triazole compounds of the present invention can, in principal be used for any organic layer, such as, for example, hole transporting layer, light emitting layer, or electron transporting layer, but are preferably used as the light emitting material in the light emitting layer, optionally as a host or guest component, or electron transporting layer.

In particular, the present organic compounds function as light emitters and are contained in the light emission layer or form the light-emitting layer.

The light emitting compounds of this invention exhibit intense fluorescence in the solid state and have excellent electric-field-applied light emission characteristics. Further, the light emitting compounds of this invention are excellent in the injection of holes from a metal electrode and the transportation of holes; as well as being excellent in the injection of electrons from a metal electrode and the transportation of electrons. They are effectively used as light emitting materials and may be used in combination with other hole transporting materials, other electron transporting materials or other dopants.

The organic compounds of the present invention form uniform thin films. The light emitting layers may therefore be formed of the present organic compounds alone.

Alternatively, the light-emitting layer may contain a known light-emitting material, a known dopant, a known hole transporting material or a known electron transporting material as required. In the organic EL device, a decrease in the brightness and life caused by quenching can be prevented by forming it as a multi-layered structure. The light-emitting material, a dopant, a hole-injecting material and an electron-injecting material may be used in combination as required. Further, a dopant can improve the light emission brightness and the light emission efficiency, and can attain the red or blue light emission. Further, each of the hole transporting zone, the light-emitting layer and the electron transporting zone may have the layer structure of at least two layers. In the hole transporting zone in this case, a layer to which holes are injected from an electrode is called "hole-injecting layer", and a layer which receives holes from the hole-injecting layer and transport the holes to a light-emitting layer is called "hole transporting layer". In the electron transporting zone, a layer to which electrons are injected from an electrode is called "electron-injecting layer", and a layer which receives electrons from the electron-injecting layer and transports the electrons to a light-emitting layer is called "electron transporting layer". These layers are selected and used depending upon factors such as the energy level and heat resistance of materials and adhesion to an organic layer or metal electrode.

The light-emitting material or the dopant which may be used in the light-emitting layer together with the organic compounds of the present invention includes for example anthracene, naphthalene, phenanthrene, pyrene, tetracene, coronene, chrysene, fluorescein, perylene, phthaloperylene, naphthaloperylene, perinone, phthaloperinone, naphthaloperinone, diphenylbutadiene, tetraphenylbutadiene, coumarine, oxadiazole, aldazine, bisbenzoxazoline, bisstyryl, pyrazine, cyclopentadiene, quinoline metal complex, aminoquinoline metal complex, benzoquinoline metal complex, imine, diphenylethylene, vinyl anthracene, diaminocarbazole, pyran, thiopyran, polymethine, merocyanine, an imidazole-chelated oxynoid compound, quinacridone, rubrene, and fluorescent dyestuffs for a dyestuff laser or for brightening.

It is also possible to use the compounds of the present invention with phosphorescent materials as a dopant in the light-emitting layer. Examples of the phosphorescent materials are, for example, metal complexes of Ir, Pt, Eu, Ru, Rh, Pd, Ag, Re, Os and Au and are described, for example, in JP2005-11804 and WO2004/034751.

Examples of typical structures of the metal complex are shown below:

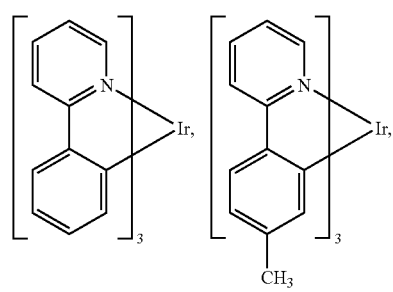

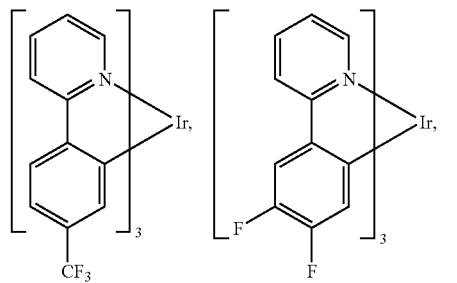

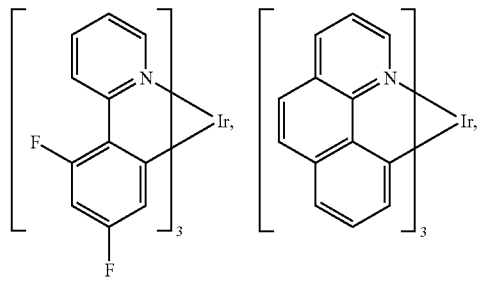

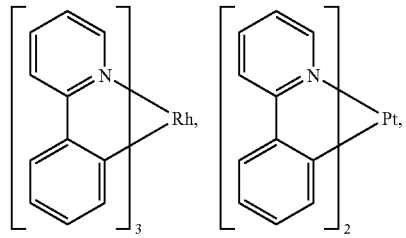

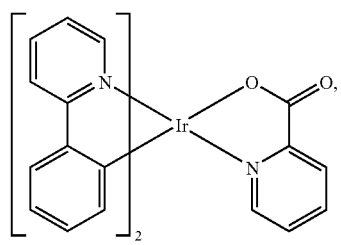

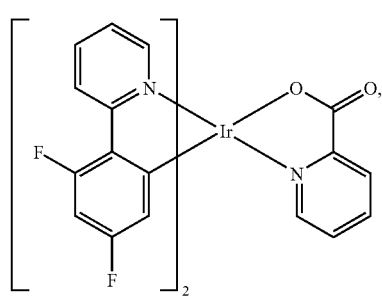

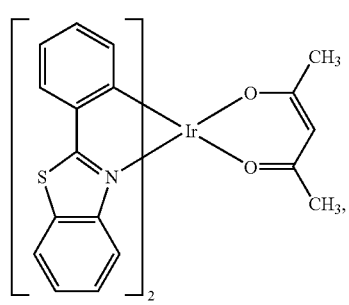

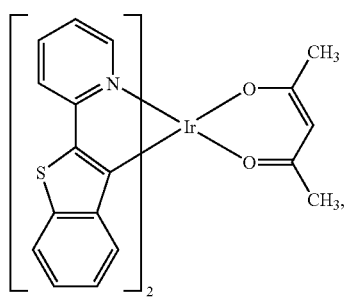
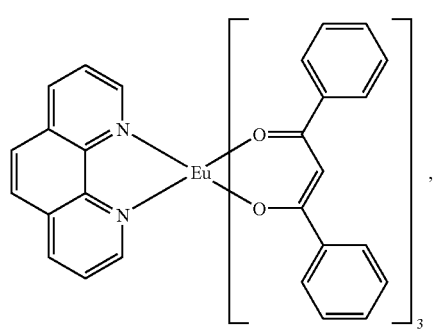
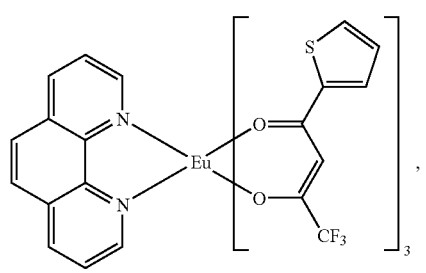
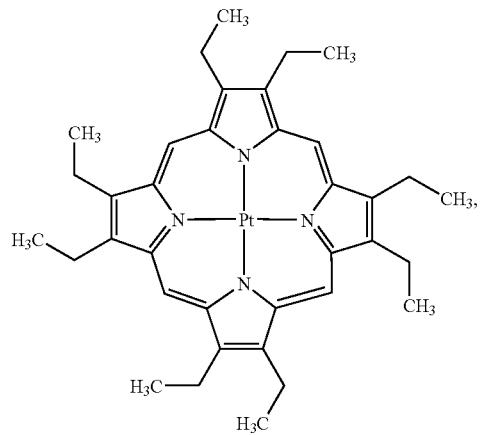
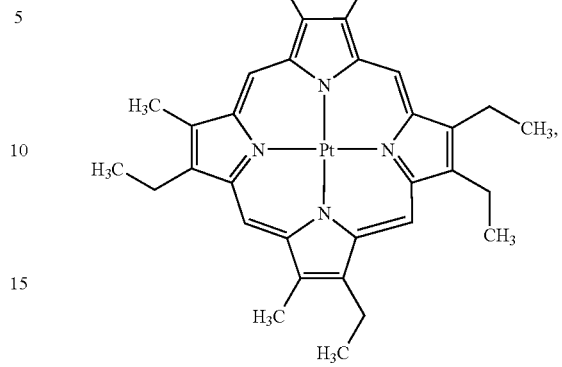
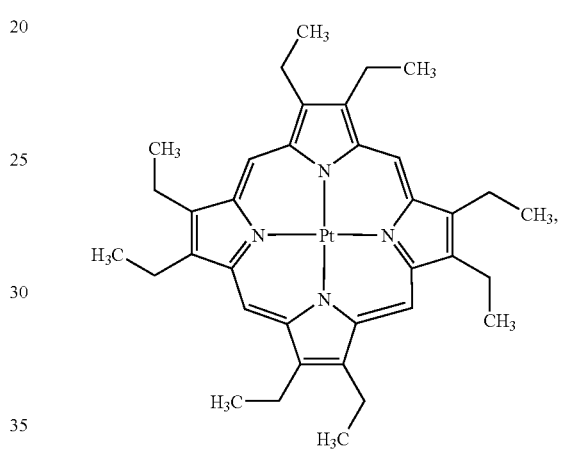
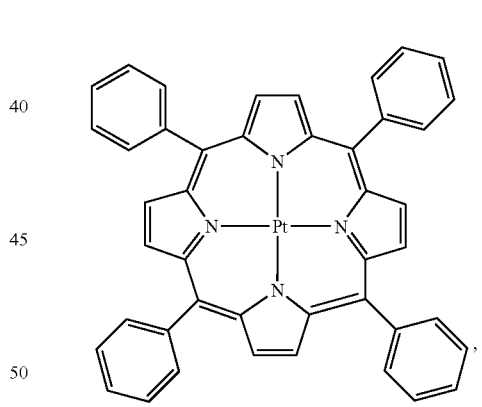
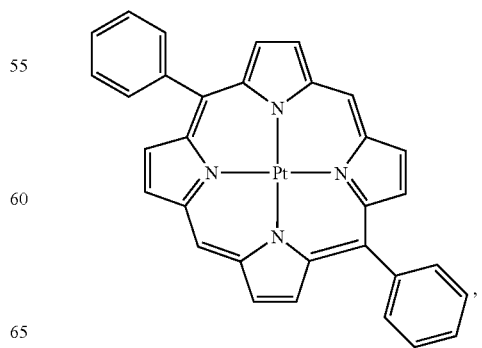

63
-continued
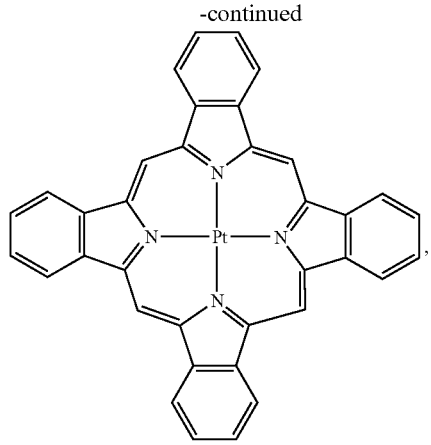
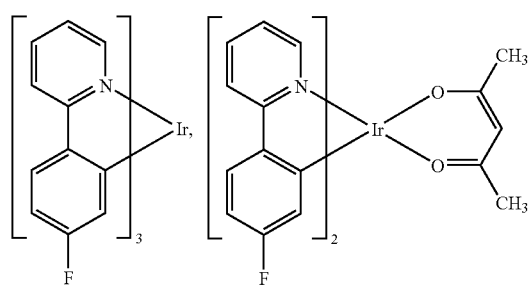
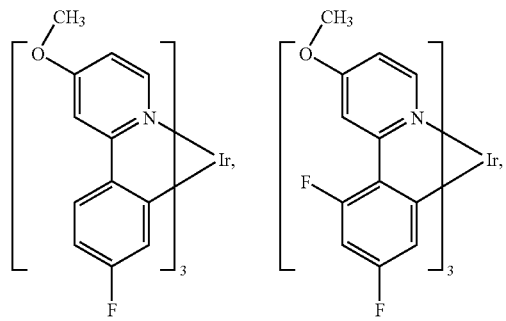
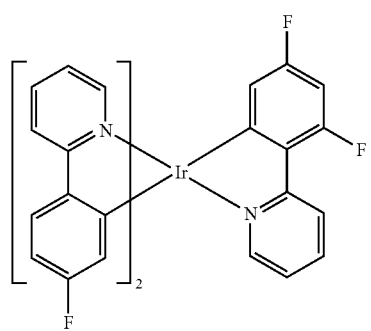
64
-continued
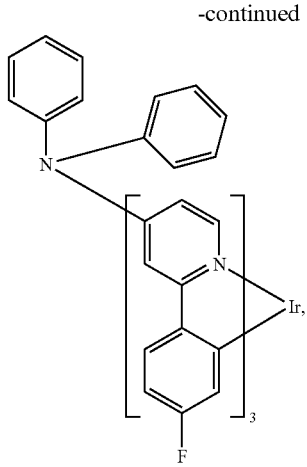
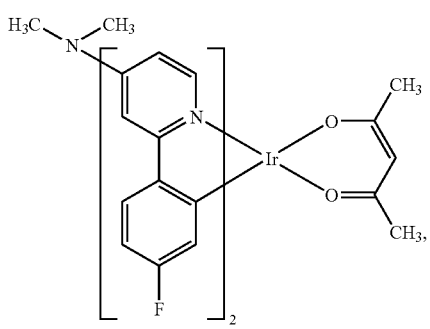
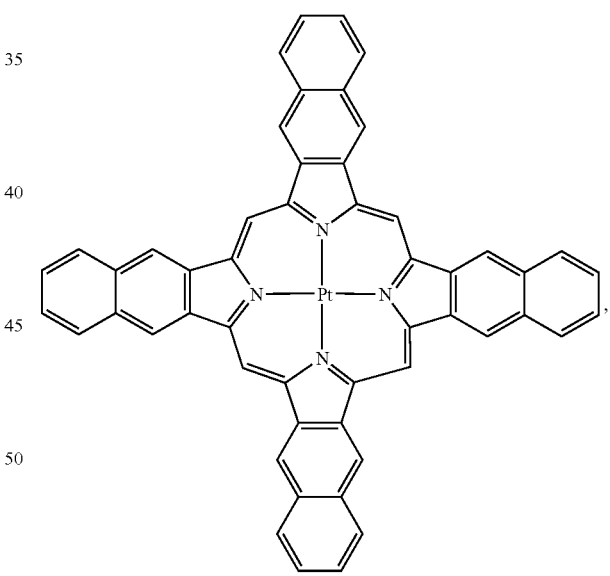
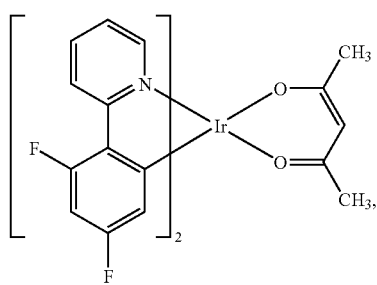

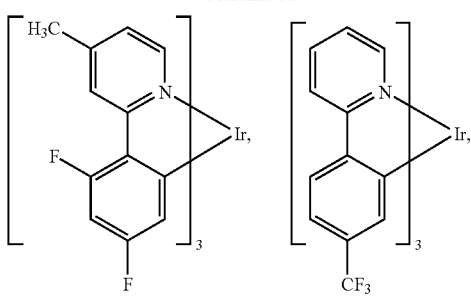
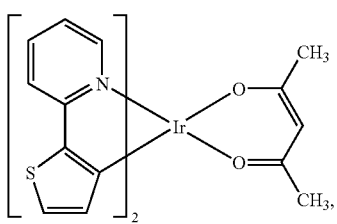
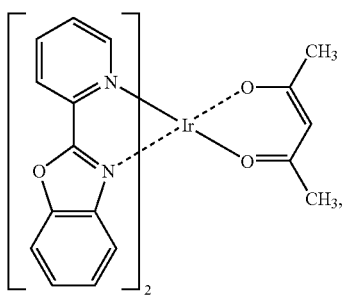
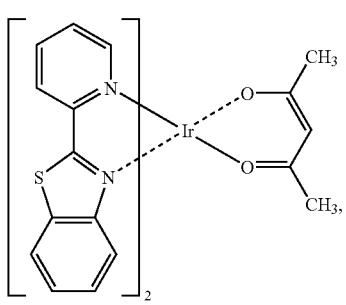
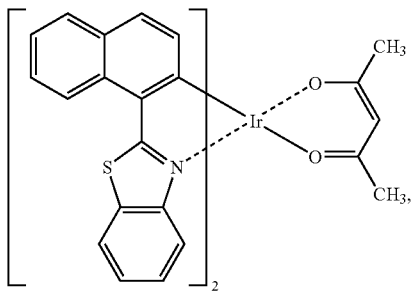
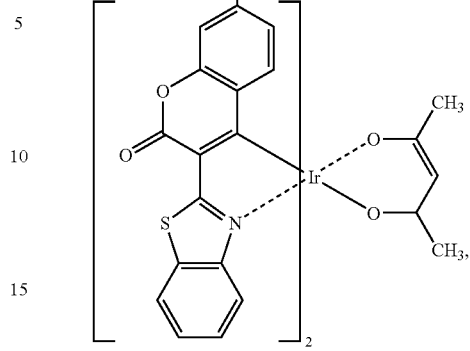
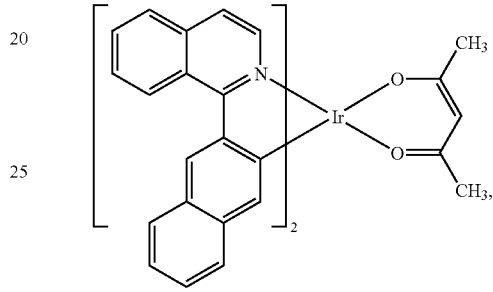
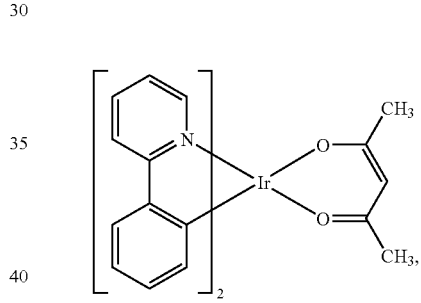
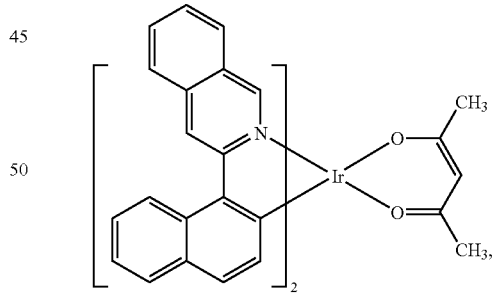
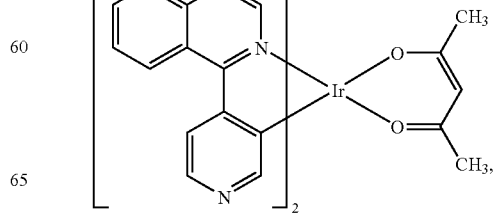

-continued

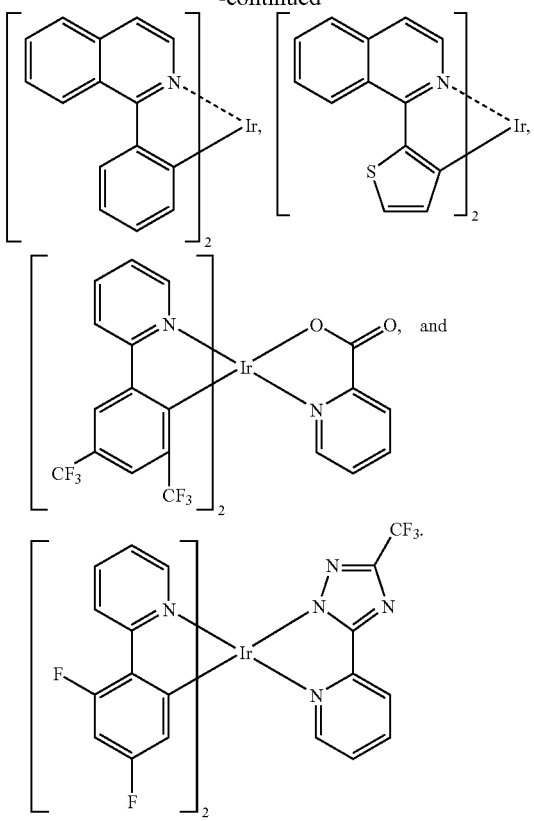

In that case the electroluminescent device may comprise in this order
(a) an anode, such as, for example, ITO,
(b1) a hole injecting layer, such as, for example, CuPc,
(b2) a hole transporting layer, such as, for example, NPD, or TCTA,
(c) a light-emitting layer, comprising a phosphorescent compound and a triazole compound of the present invention, especially a compound A-1 to A-29, or D1 to D8,
a positive hole inhibiting layer, such as, for example, BCP,
(d) an electron transporting layer, such as, for example, Alq$_3$, and
an inorganic compound layer, such as, for example, LiF,
(e) a cathode, such as, for example, Al.

If the triazole compounds of the present invention are used as host together with guest compounds, such as, for example, 2,5,8,11-tetra-t-butylperylene, or the compounds, described, for example, in WO2004039786, such as, for example,

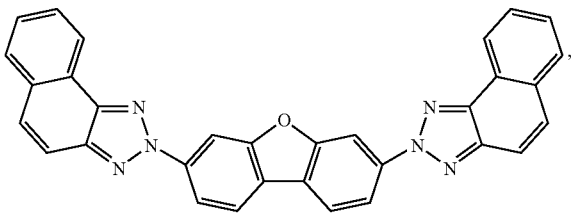 [SMILES: c1ccc2c(c1)ccc1nn(-c3ccc4c(c3)oc3cc(-n5nc6ccc7ccccc7c6n5)ccc34)nc12]

the electroluminescent device may comprise in this order
(a) an anode, such as, for example, ITO,
(b1) a hole injecting layer, such as, for example, CuPc,
(b2) a hole transporting layer, such as, for example, NPD, or TCTA,
(c) a light-emitting layer, comprising a fluorescent guest compound and a triazole host compound of the present invention, especially a compound A-1 to A-21, or B1 to B4, optionally a positive hole inhibiting layer, such as, for example, BCP,
(d) an electron transporting layer, such as, for example, Alq$_3$, or TPBI and an inorganic compound layer, such as, for example, LiF,
(e) a cathode, such as, for example, Al.

The weight ratio of compound of the formula I, or II to the dopant is in general 50:50 to 99.99:0.01, preferably 80:20 to 99.99:0.01, more preferably 90:10 to 99.9:0.1.

If the guest is a phosphorescent compound, its concentration is normally 5-10%.

The compounds of the present invention and the above compound or compounds that can be used in a light-emitting layer may be used in any mixing ratio for forming a light-emitting layer. That is, the organic compounds of the present invention may provide a main component for forming a light-emitting layer, or they may be a doping material in another main material, depending upon a combination of the above compounds with the organic compounds of the present invention.

The hole-injecting material is selected from compounds which are capable of transporting holes, are capable of receiving holes from the anode, have an excellent effect of injecting holes to a light-emitting layer or a light-emitting material, prevent the movement of excitons generated in a light-emitting layer to an electron-injecting zone or an electron-injecting material and have the excellent capability of forming a thin film. Suitable hole-injecting materials include for example a phthalocyanine derivative, a naphthalocyanine derivative, a porphyrin derivative, oxazole, oxadiazole, triazole, imidazole, imidazolone, imidazolthione, pyrazoline, pyrazolone, tetrahydroimidazole, oxazole, oxadiazole, hydrazone, acylhydrazone, polyarylalkane, stilbene, butadiene, benzidine type triphenylamine, styrylamine type triphenylamine, diamine type triphenylamine, derivatives of these, and polymer materials such as polyvinylcarbazole, polysilane and an electroconducting polymer.

In the organic EL device of the present invention, the hole-injecting material which is more effective is an aromatic tertiary amine derivative or a phthalocyanine derivative. Although not specially limited, specific examples of the tertiary amine derivative include triphenylamine, tritolylamine, tolyidiphenylamine, N,N'-diphenyl-N,N'-(3-methylphenyl)-1,1-biphenyl-4,4'-diamine, N,N,N',N'-tetra(4-methylphenyl)-1,1'-phenyl-4,4'-diamine, N,N,N',N'-tetra(4-methylphenyl)-1,1'-biphenyl-4,4'-diamine, N,N'-diphenyl-N,N'-di(1-naphthyl)-1,1'-biphenyl-4,4'-diamine, N,N'-di(methylphenyl)-N,N'-di(4-n-butylphenyl)-phenanthrene-9,10-diamine, 4,4', 4''-tris(3-methylphenyl)-N-phenylamino)triphenylamine, 1,1-bis(4-di-p-tolylaminophenyl)cyclohexane, and oligomers or polymers having aromatic tertiary amine structures of these.

Although not specially limited, specific examples of the phthalocyanine (Pc) derivative include phthalocyanine derivatives or naphthalocyanine derivatives such as H$_2$Pc, CuPc, CoPc, NiPc, ZnPc, PdPc, FePc, MnPc, ClAlPc, ClGaPc, ClInPc, ClSnPc, Cl$_2$SiPc, (HO)AlPc, (HO)GaPc, VOPc, TiOPc, MoOPc, and GaPc-O—GaPc.

The hole transporting layer can reduce the driving voltage of the device and improve the confinement of the injected charge recombination within the light emitting layer, comprising the compounds of the present invention. Any conventional suitable aromatic amine hole transporting material described for the hole-injecting layer may be selected for forming this layer.

A preferred class of hole transporting materials is comprised of 4,4'-bis(9-carbazolyl)-1,1'-biphenyl compounds of the formula

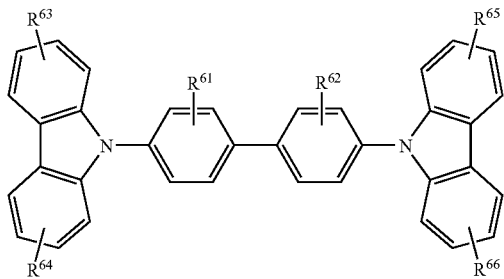

wherein $R^{61}$ and $R^{62}$ is a hydrogen atom or an $C_1$-$C_3$alkyl group; $R^{63}$ through $R^{66}$ are substituents independently selected from the group consisting of hydrogen, a $C_1$-$C_6$alkyl group, a $C_1$-$C_6$alkoxy group, a halogen atom, a dialkylamino group, a $C_6$-$C_{30}$aryl group, and the like. Illustrative examples of 4,4'-bis(9-carbazolyl)-1,1'-biphenyl compounds include 4,4'-bis(9-carbazolyl)-1,1'-biphenyl and 4,4'-bis(3-methyl-9-carbazolyl)-1,1'-biphenyl, and the like; or 4,4',4''-tri-(N-carbazoyl)triphenylamine (TCTA).

In addition, polymeric material can be used as a hole injection material and a hole transporting material, such as poly (N-vinylcarbazole) (PVK), polythiophenes, polypyrrole, polyaniline, and copolymers such as poly(3,4-ethylenedioxythiophene)/poly(4-styrenesulfonate) also called PEDOT/PSS.

The electron transporting layer is not necessarily required for the present device, but is optionally and preferably used for the primary purpose of improving the electron injection characteristics of the EL devices and the emission uniformity. Illustrative examples of electron transporting compounds, which can be utilized in this layer, include the metal chelates of 8-hydroxyquinoline as disclosed in U.S. Pat. Nos. 4,539, 507, 5,151,629, and 5,150,006, the disclosures of which are totally incorporated herein by reference.

Examples of suitable electron transporting materials are metal complex compounds and nitrogen-containing five-membered ring derivatives.

Although not specially limited, specific examples of the metal complex compound include lithium 8-hydroxyquinolinate, zinc bis(8-hydroxyquinolinate), copper bis(8-hydroxyquinolinate), manganese bis(8-hydroxyquinolinate), aluminum tris(8-hydroxyquinolinate), aluminum tris(2-methyl-8-hydroxyquinolinate), gallium tris(8-hydroxyquinolinate), beryllium bis(10-hydroxybenzo[h]quinolinate), zinc bis(10-hydroxybenzo[h]quinolinate), chlorogallium bis(2-methyl-8-quinolinate), gallium bis(2-methyl-8-quinolinate)(o-cresolate), aluminum bis(2-methyl-8-quinolinate)(1-naphtholate), gallium bis(2-methyl-8-quinolinate)(2-naphtholate), gallium bis(2-methyl-8-quinolinate)phenolate, zinc bis(o-(2-benzooxazolyl)phenolate), zinc bis(o-(2-benzothiazolyl)phenolate) and zinc bis(o-(2-benzotrizolyl)phenolate). The nitrogen-containing five-membered derivative is preferably an oxazole, thiazole, thiadiazole, or triazole derivative. Although not specially limited, specific examples of the above nitrogen-containing five-membered derivative include 2,5-bis(1-phenyl)-1,3,4-oxazole, 1,4-bis(2-(4-methyl-5-phenyloxazolyl)benzene, 2,5-bis(1-phenyl)-1,3,4-thiazole, 2,5-bis(1-phenyl)-1,3,4-oxadiazole, 2-(4'-tert-butylphenyl)-5-(4''-biphenyl) 1,3,4-oxadiazole, 2,5-bis(1-naphthyl)-1,3,4-oxadiazole, 1,4-bis[2-(5-phenyloxadiazolyl)]benzene, 1,4-bis[2-(5-phenyloxadiazolyl)-4-tert-butylbenzene], 2-(4'-tert-butylphenyl)-5-(4''-biphenyl)-1,3,4-thiadiazole, 2,5-bis(1-naphthyl)-1,3,4-thiadiazole, 1,4-bis[2-(5-phenylthiazolyl)]benzene, 2-(4'-tert-butylphenyl)-5-(4''-biphenyl)-1,3,4-triazole, 2,5-bis(1-naphthyl)-1,3,4-triazole and 1,4-bis[2-(5-phenyltriazolyl)]benzene. Another class of electron transport materials are oxadiazole metal chelates, such as bis[2-(2-hydroxyphenyl)-5-phenyl-1,3,4-oxadiazolato]zinc; bis[2-(2-hydroxyphenyl)-5-phenyl-1,3,4-oxadiazolato]beryllium; bis [2-(2-hydroxyphenyl)-5-(1-naphthyl)-1,3,4-oxadiazolato] zinc; bis[2-(2-hydroxyphenyl)-5-(1-naphthyl)-1,3,4-oxadiazolato]beryllium; bis[5-biphenyl-2-(2-hydroxyphenyl)-1,3,4-oxadiazolato]zinc; bis[5-biphenyl-2-(2-hydroxyphenyl)-1,3,4-oxadiazolato]beryllium; bis(2-hydroxyphenyl)-5-phenyl-1,3,4-oxadiazolato]lithium; bis[2-(2-hydroxyphenyl)-5-p-tolyl-1,3,4-oxadiazolato]zinc; b is 2-(2-hydroxyphenyl)-5-p-tolyl-1,3,4-oxadiazolato]beryllium; bis[5-(p-tert-butylphenyl)-2-(2-hydroxyphenyl)-1,3,4-oxadiazolato]zinc; bis[5-(p-tert-butylphenyl)-2-(2-hydroxyphenyl)-1,3,4-oxadiazolato]beryllium; bis[2-(2-hydroxyphenyl)-5-(3-fluorophenyl)-1,3,4-oxadiazolato] zinc; bis[2-(2-hydroxyphenyl)-5-(4-fluorophenyl)-1,3,4-oxadiazolato]zinc; bis[2-(2-hydroxyphenyl)-5-(4-fluorophenyl)-1,3,4-oxadiazolato]beryllium; bis[5-(4-chlorophenyl)-2-(2-hydroxyphenyl)-1,3,4-oxadiazolato] zinc; bis[2-(2-hydroxy phenyl)-5-(4-methoxyphenyl)-1,3,4-oxadiazolato]zinc; bis[2-(2-hydroxy-4-methylphenyl)-5-phenyl-1,3,4-oxadiazolato]zinc; bis[2-.alpha.-(2-hydroxynaphthyl)-5-phenyl-1,3,4-oxadiazolato]zinc; bis[2-(2-hydroxyphenyl)-5-p-pyridyl-1,3,4-oxadiazolato]zinc; bis [2-(2-hydroxyphenyl)-5-p-pyridyl-1,3,4-oxadiazolato] beryllium; bis[2-(2-hydroxyphenyl)-5-(2-thiophenyl)-1,3,4-oxadiazolato]zinc; bis[2-(2-hydroxyphenyl)-5-phenyl-1,3,4-thiadiazolato]zinc; bis[2-(2-hydroxyphenyl)-5-phenyl-1,3,4-thiadiazolato]beryllium; bis[2-(2-hydroxyphenyl)-5-(1-naphthyl)-1,3,4-thiadiazolato]zinc; and bis[2-(2-hydroxyphenyl)-5-(1-naphthyl)-1,3,4-thiadiazolato] beryllium, and the like.

Other suitable compounds for the electron transporting material are heterocyclic compounds, such as benzimidazole derivatives, benzoxazole derivatives, oxadiazole derivatives, thiadiazole derivative, triazole derivatives, pyrazine derivatives, phenanthroline derivatives, quinoxaline derivatives, quinoline derivatives, benzoquinoline derivatives, oligo-pyridine derivatives, e.g. bipyridine derivatives and terpyridine derivatives, naphthylidine derivatives, indole derivatives and naphthalimide derivatives; silole derivatives; and phosphineoxide derivatives, such as, for example, 1,3,5-tris-(N-phenyl-benzimidazol-2-yl)benzene (TPBI).

The property of charge injection can be improved by adding an electron-accepting compound to the hole injection layer and/or the hole transporting layer and electron-donating material to the electron transporting layer.

It is possible to add a reducing dopant to the electron transporting layer to improve the EL device property. The reducing dopant is a material that can reduce the electron transporting material. Examples of the reducing dopant are alkali metals, such as Na, K, Rb and Cs, and alkaline earth metals, such as Ca, Sr and Ba.

The organic EL device of the present invention may comprise an inorganic compound layer between at least one of the electrodes and the above organic thin layer. Examples of the inorganic compound used for the inorganic compound layer include various types of oxides, nitrides and oxide nitrides, such as alkali metal oxides, alkaline earth metal oxides, rare earth metal oxides, alkali metal halides, alkaline earth metal halides, rare earth metal halides, $SiO_x$, $AlO_x$, $SiN_x$, SiON, AlON, GeO$_x$, LiO$_x$, LiON, TiO$_x$, TiON, TaO$_x$, TaON, TaN$_x$ and C. In particular, as the component contacting the anode, SiO$_x$, AlO$_x$, SiN$_x$, SiON, AlON, GeO$_x$ and C are preferred, because a suitable interface layer of injection is formed. As the component contacting the cathode, LiF, MgF$_2$, CaF$_2$ and NaF are preferable.

A positive hole inhibiting layer can be formed by preparing an organic film containing at least one positive hole inhibiting material between the electron transporting layer and the light-emitting layer.

It is preferred that the positive hole inhibiting materials for a positive hole inhibiting layer have high electron injection/transporting efficiency from the electron transporting layer to the light emission layer and also have higher ionisation potential than the light emitting layer to prevent the flowing out of positive holes from the light emitting layer to avoid a drop in luminescence efficiency.

As the positive hole inhibiting material known materials, such as Balq, TAZ and phenanthroline derivatives, e.g. bathocuproine (BCP), can be used:

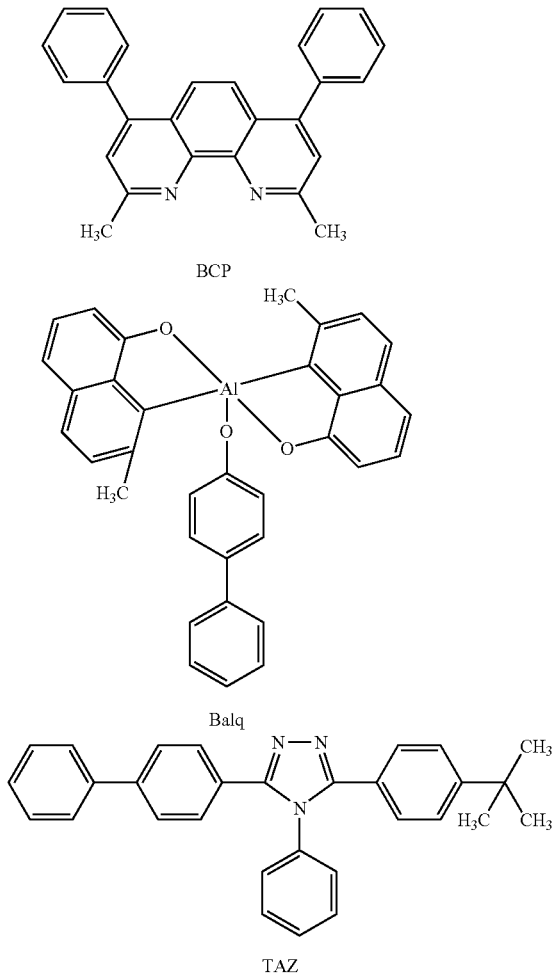

BCP

Balq

TAZ

In the organic EL device of the present invention, the light-emitting layer may contain, in addition to the light-emitting organic material of the present invention, at least one of other light-emitting material, other dopant, other hole-injecting material and other electron-injecting material. For improving the organic EL device of the present invention in the stability against temperature, humidity and ambient atmosphere, a protective layer may be formed on the surface of the device, or the device as a whole may be sealed with a silicone oil, or the like. The electrically conductive material used for the anode of the organic EL device is suitably selected from those materials having a work function of greater than 4 eV. The electrically conductive material includes carbon, aluminum, vanadium, iron, cobalt, nickel, tungsten, silver, gold, platinum, palladium, alloys of these, metal oxides such as tin oxide and indium oxide used for ITO substrates or NESA substrates, and organic electroconducting polymers, such as polythiophene and polypyrrole.

The electrically conductive material used for the cathode is suitably selected from those having a work function of smaller than 4 eV. The electrically conductive material includes magnesium, calcium, tin, lead, titanium, yttrium, lithium, ruthenium, manganese, aluminum and alloys of these, while the electrically conductive material shall not be limited to these. Examples of the alloys include magnesium/silver, magnesium/indium and lithium/aluminum, while the alloys shall not be limited to these. Each of the anode and the cathode may have a layer structure formed of two layers or more as required.

For the effective light emission of the organic EL device, at least one of the electrodes is desirably sufficiently transparent in the light emission wavelength region of the device. Further, the substrate is desirably transparent as well. The transparent electrode is produced from the above electrically conductive material by a deposition method or a sputtering method such that a predetermined light transmittance is secured. The electrode on the light emission surface side has for instance a light transmittance of at least 10%. The substrate is not specially limited so long as it has adequate mechanical and thermal strength and has transparency. For example, it is selected from glass substrates and substrates of transparent resins such as a polyethylene substrate, a polyethylene terephthalate substrate, a polyether sulfone substrate and a polypropylene substrate.

In the organic EL device of the present invention, each layer can be formed by any one of dry film forming methods such as a vacuum deposition method, a sputtering method, a plasma method and an ion plating method and wet film forming methods such as a spin coating method, a dipping method and a flow coating method. The thickness of each layer is not specially limited, while each layer is required to have a proper thickness. When the layer thickness is too large, inefficiently, a high voltage is required to achieve predetermined emission of light. When the layer thickness is too small, the layer is liable to have a pinhole, etc., so that sufficient light emission brightness is hard to obtain when an electric field is applied. The thickness of each layer is for example in the range of from about 5 nm to about 10 µm, for instance about 10 nm to about 0.2 µm.

In the wet film forming method, a material for forming an intended layer is dissolved or dispersed in a proper solvent such as ethanol, chloroform, tetrahydrofuran and dioxane, and a thin film is formed from the solution or dispersion. The solvent shall not be limited to the above solvents. For improving the film formability and preventing the occurrence of pinholes in any layer, the above solution or dispersion for forming the layer may contain a proper resin and a proper additive. The resin that can be used includes insulating resins such as polystyrene, polycarbonate, polyarylate, polyester, polyamide, polyurethane, polysulfone, polymethyl methacrylate, polymethyl acrylate and cellulose, copolymers of these, photoconductive resins such as poly-N-vinylcarbozole and polysilane, and electroconducting polymers such as polythiophene and polypyrrole. The above additive includes an antioxidant, an ultraviolet absorbent and a plasticizer.

When the light-emitting organic material of the present invention is used in a light-emitting layer of an organic EL device, an organic EL device can be improved in organic EL device characteristics such as light emission efficiency and maximum light emission brightness. Further, the organic EL device of the present invention is remarkably stable against heat and electric current and gives a usable light emission brightness at a low actuation voltage. The problematic deterioration of conventional devices can be remarkably decreased.

The organic EL device of the present invention has significant industrial values since it can be adapted for a flat panel display of an on-wall television set, a flat light-emitting device, a light source for a copying machine or a printer, a light source for a liquid crystal display or counter, a display signboard, lighting application and a signal light.

The material of the present invention can be used in the fields of an organic EL device, an electrophotographic photoreceptor, a photoelectric converter, a solar cell, and an image sensor.

The following Examples illustrate the invention. In the Examples and throughout this application, the term light emitting material means the present triazine compounds.

EXAMPLES

Example 1

A) 4-Bromo-N-[1-(4-bromo-phenyl)-1-ethoxy-meth-(z)-ylidene]benzamide

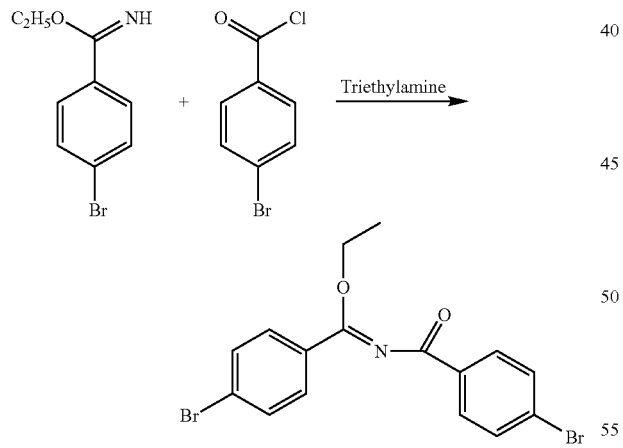

4-Bromobenzenecarboximidate (25 g, 0.10 mole) is added to toluene (225 ml). Then triethylamine (25 ml, 0.17 mole) is added. The reaction mixture is stirred at room temperature for 10 minutes. 4-bromobenzoyl chloride (25 g, 0.12 mole) in toluene (25 ml) is added to the reaction mixture in 30 minutes at room temperature. After stirring the reaction mixture overnight, it is filtered and the toluene layer is concentrated. The product, 4-Bromo-N-[1-(4-bromo-phenyl)-1-ethoxy-meth-(z)-ylidene]benzamide, from the toluene concentrate is then washed with methanol (30 ml) and dried in vacuum (Yield=30 g (62%)). The product is used without further purification in the next reaction step.

B) 1,3,5 tris-(4-bromophenyl)-1H-[1,2,4 triazole]

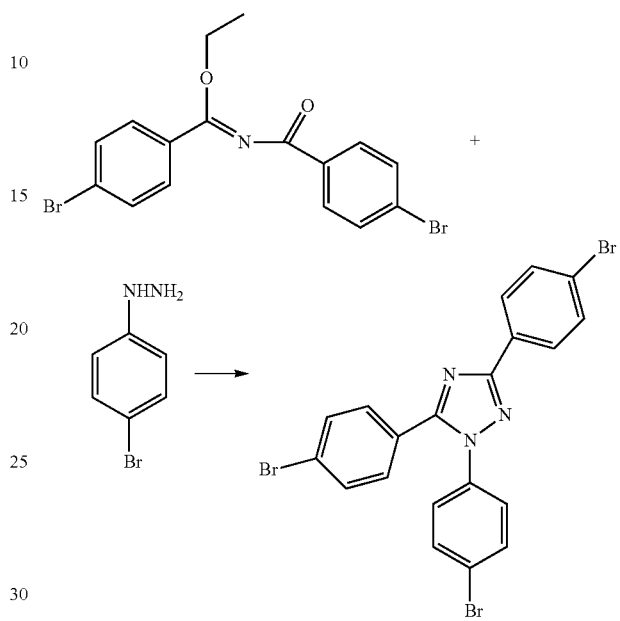

A solution of the product of step A) (20 g, 0.048 mmole) and 4-bromophenyl hydrazine (11 g, 0.05 mol) in 300 ml tetrachloromethane (CCl$_4$) is stirred at room temperature for 5 hours. The reaction mixture is filtered and washed with carbon tetrachloride (25 ml). The combined filtrate is concentrated under vacuum. The crude product is washed with methanol (Yield=11.8 g (46%)).

Mp.=167-8° C.

$^1$H NMR (ppm, CDCl$_3$): 8.07 (d, J=8.60 Hz, 2H), 7.59 (d, J=8.60 Hz, 4H), 7.53 (d, J=8.60 Hz, 2H), 7.28 (d, J=8.60 Hz, 2H)

C) 1,3,5,tris tertriphenyl-1H-[1,2,4]triazole—Compound 7

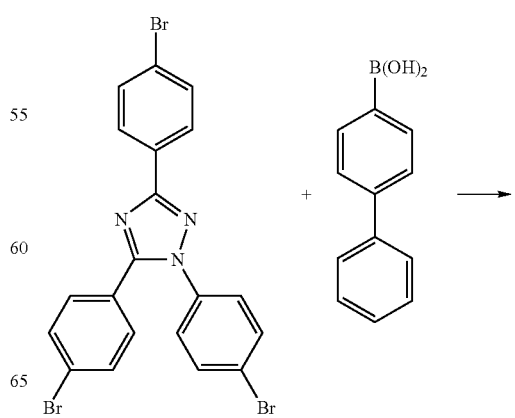

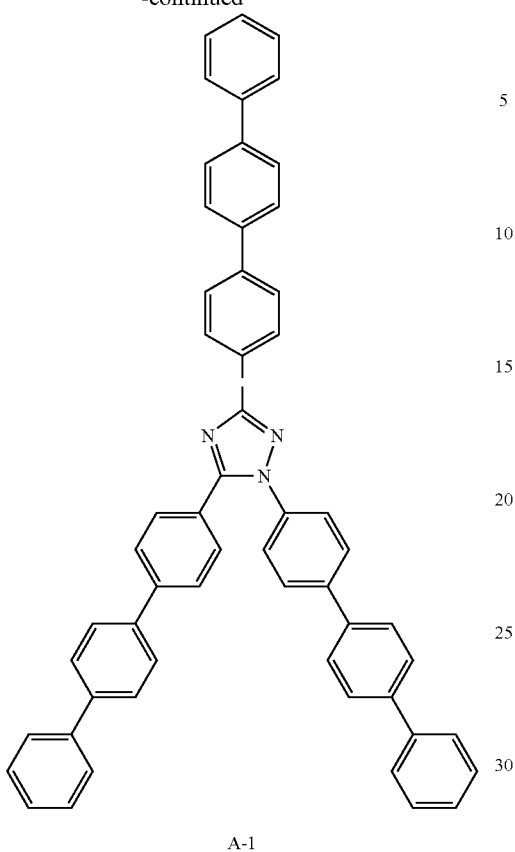

A-1

The compound obtained in step B) (6.0 g, 0.011 mole), 4-biphenyl boronic acid (7.3 g, 0.037 mole), palladium acetate (170 mg), potassium phosphate (12.7 g, 0.06 mole), and tetrabutyl ammonium bromide (500 mg) are charged to a flask containing 180 ml of THF. Then potassium carbonate (8.3 g, 0.06 mole) in 60 ml of water is added and the reaction mixture is stirred and refluxed at 80° C. under a nitrogen atmosphere for 24 hours. The reaction mixture is cooled and diluted with 100 ml of water, stirred for 15 minutes and filtered. The solid is crystallised twice from 400 ml ethylene dichloride, then absorbed on silica gel and chromatographed using ethylene dichloride:hexane (10:90). The silica gel bed is stirred with ethylene dichloride and filtered and the solid obtained, compound A-1, is again crystallised with ethylene dichloride (Yield=2.72 g (32.4%)).

Mp.=252-4° C.

$^1$H NMR (ppm, CDCl$_3$): 8.37 (d, J=8.30 Hz, 2H), 7.82-7.58 (m, 28H), 7.5-7.46 (m, 6H), 7.4-7.36 (m, 3H).

Example 2

A) Naphthalene-1-carboxylic acid 1-(4-bromo-phenyl)-1-ethoxy-methylideneamide

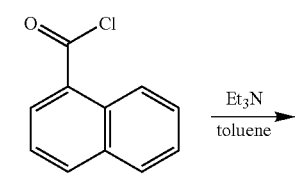

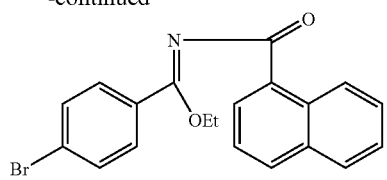

4-Bromobenzene carboximidate (6.0 g, 0.0263 mol) and triethyl amine (3.0 g, 0.0297 mol) is dissolved in toluene (15 ml). It is then cooled to 10° C. 1-naphthoyl chloride (5.0 g, 0.0263 mol) in toluene (10 ml) is added slowly to the reaction mixture over a period of 15 minutes under a nitrogen atmosphere. The reaction mixture is then stirred for 10 hours at 25° C. It is then filtered to remove the triethyl amine hydrochloride salt and the filtrate is concentrated to obtain a yellowish solid, which is washed with hexane (20 ml) and methanol (10 ml) respectively to obtain the pure desired product (Yield=7.5 g (75%)).

Mp.: 104-105° C.

$^1$H NMR (ppm, CDCl$_3$): 9.02 (d, J=7.8 Hz, 1H), 8.15 (d, J=7.8 Hz, 1H), 8.01 (d, J=7.8 Hz, 1H), 7.88 (d, J=7.8 Hz, 1H), 7.65-7.38 (m, 8H), 4.42 (q, J=7.0 Hz, 2H), 1.49 (t, J=7.0 Hz, 3H)

B) 3-(4-Bromo-phenyl)-1,5-di-naphthalen-1-yl-1H-[1,2,4]triazole

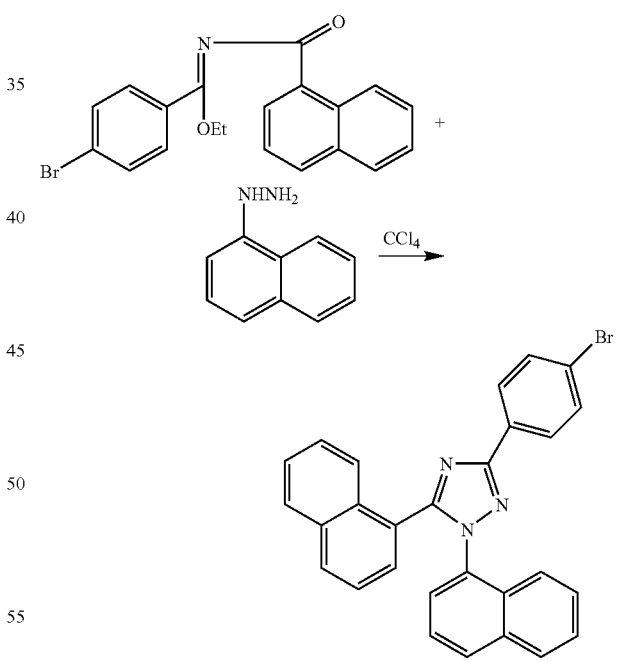

The compound obtained in step A) (1.0 g, 0.026 mol) and 1-naphthyl hydrazine (0.45 g, 0.028 mol) is dissolved in CCl$_4$ (15 ml) and stirred for 10 hours at 25° C. under a nitrogen atmosphere. The reaction mixture is stirred for 12 hours and filtered to remove traces of insoluble particles. The CCl$_4$ solution is then concentrated and a few drops of methanol are added to the residue, wherein a brownish solid is obtained (Yield=0.7 g (56%)).

Mp.: 218-220° C.

¹H NMR (ppm, CDCl₃): 8.3-8.15 (m, 3H), 7.9-7.75 (m, 5H), 7.63 (d, J=7.8 Hz, 2H), 7.58-7.46 (m, 4H), 7.3-7.2 (m, merged with CDCl₃ signal, 3H), 7.2-7.12 (m, 1H)

C) 1,5-Di-naphthalen-1-yl-3-[1,1',4',1"]terphenyl-4-yl-1H-[1,2,4]triazole

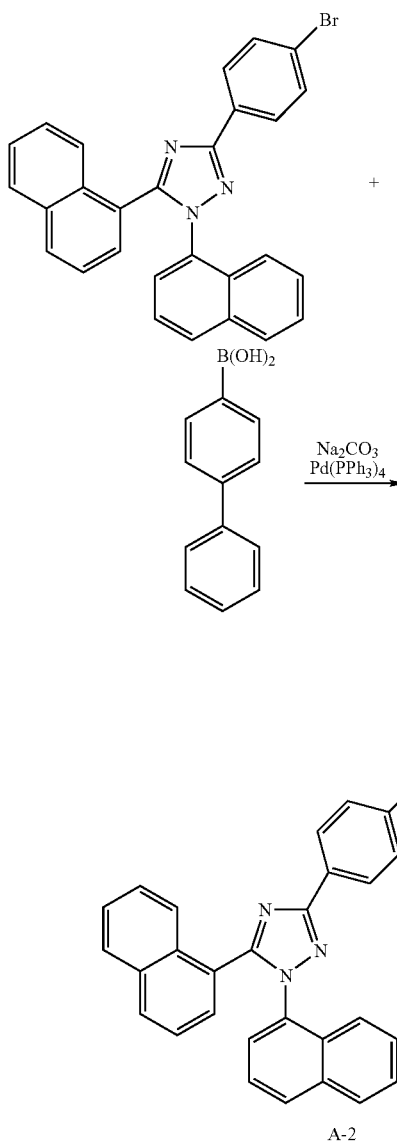

The compound obtained in step B) (2.0 g, 0.002 mmol) is dissolved in a toluene-ethanol mixture (27:4.5 ml). A sodium carbonate solution (1.0 g dissolved in 9.0 ml water) is added. 4-biphenyl boronic acid (1.0 g, 5.0 mmol) and Pd(PPh₃)₄ (0.275 g, 0.00023 mol) is then added to the reaction mixture under a nitrogen atmosphere. The reaction mixture is then stirred for 25 hours at 95° C. with constant monitoring by TLC (Thin Layer Chromatography). After heating for 25 hours the reaction mixture is cooled and the organic layer is separated off. The aqueous layer is extracted with dichloromethane (2×10 ml). The combined organic layer is dried over anhydrous sodium sulphate. The solvent is removed under vacuum and the residue chromatographed using a silica gel column. Elution with a ethylacetate-hexane mixture (7:93) result in the desired compound. The solid is crystallized from hexane-ethyl acetate (80:20) (Yield=0.4 g (17.3%)).

Mp.: 197-198° C.

¹H NMR (ppm, CDCl₃); 8.44 (d, J=8.2 Hz, 2H), 8.3 (d of multiplet, J=8.6 Hz, 1H), 7.9-7.75 (cluster of m, 9H), 7.7 (d, J=8.2 Hz, 2H), 7.67 (d, J=8.2 Hz, 2H), 7.56-7.7.42 (cluster of m, 6H), 7.38 (m, 1H), 7.3-7.26 (m, merged with CDCl₃ signal, 3H), 7.25-7.19 (m, 1H)

Example 3

3,5-bis(4'-(Napthalene-1"yl)phenyl)-1(phenyl)-[1H]-[1,2,4]triazole

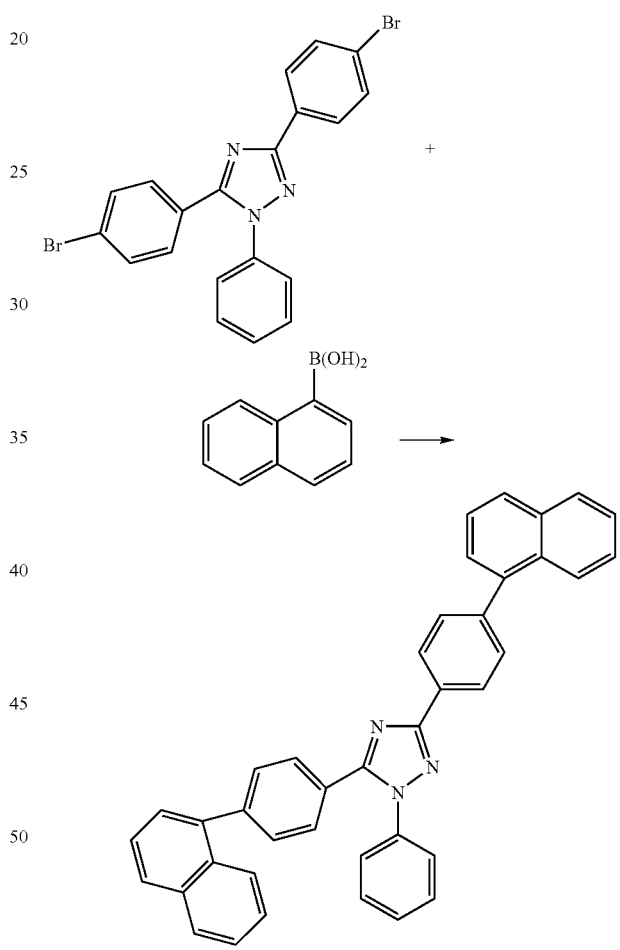

Napthalene-1-boronic acid (1.6 g, 0.009 mol) and sodium carbonate (1.0 g in 9 ml water) are stirred under a nitrogen atmosphere and tetrakis(triphenylphospine)palladium (0.1 g, 0.00009 mol) is added to the stirred solution. The stirring is continued at room temperature for 5 minutes and 1-naphthyl boronic acid (1.8 g, 0.0039 mol) dissolved in 27 ml toluene and 5 ml of ethanol is added. Then the reaction mixture is stirred at 85° C. under nitrogen for 24 hours. The reaction mixture is cooled to room temperature and diluted with water. The organic layer is separated and the aqueous layer extracted with ethyl acetate. The combined organic layer is dried, evaporated and the dried solid chromatographed on a silica gel column with hexane:ethyl acetate (98:2) (Yield=0.55 g (18%)).

Mp.=98-100° C.

$^1$H NMR (ppm, CDCl$_3$); 8.40 (d, J=8.21 Hz, 2H), 7.99 (d, J=8.21 Hz, 1H), 7.93-7.87 (m, 4H), 7.74 (d, J=8.21 Hz, 2H), 7.64 (d, J=8.21 Hz, 2H), 7.58-7.43 (m, 16H).

Example 4

1-Phenyl-3,5-bis-[4-styryl-phenyl]-1H-[1,2,4]triazole

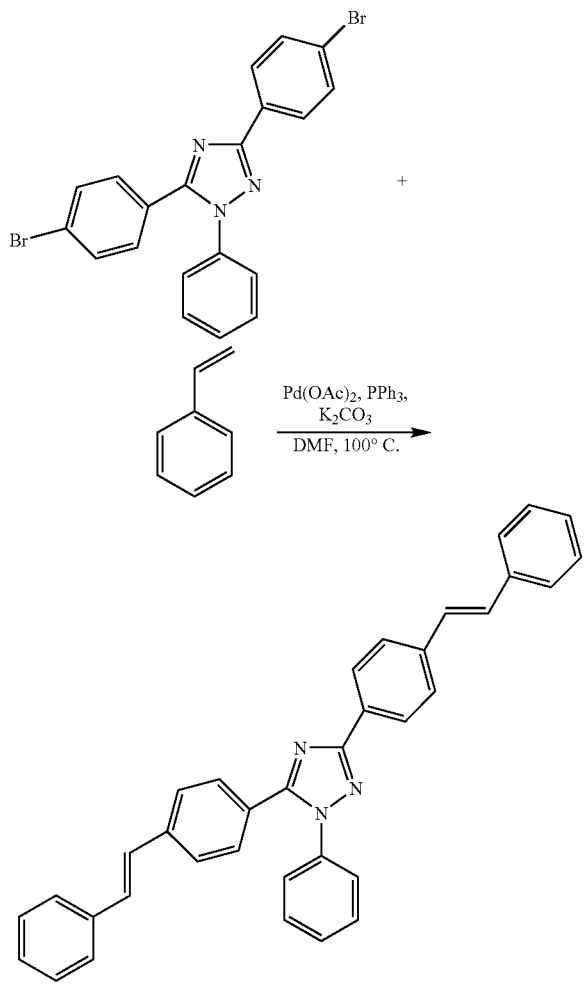

A-19

Styrene (1.72 g, 16.5 mmol), Pd(OAc)$_2$ (0.080 g, 0.35 mmol), PPh$_3$ (0.095 g, 0.36 mmol) and K$_2$CO$_3$ (2.0 g, 14.5 mmol) are added to the dibromo triazole shown above (2.5 g, 5.5 mmol) in DMF (25 ml) under a nitrogen atmosphere. The reaction mixture is stirred at 100° C. for 24 h, worked up and chromatographed. Elution with methylene chloride/hexane (1:1) give the desired product A-19 (yield: 1.2 g (43%); mp: 218-220° C.).

$^1$H NMR (ppm, CDCl$_3$): 8.24 (d, J=8.2 Hz, 2H), 7.62 (d, J=8.2 Hz, 2H), 7.6-7.44 (complex m, 12H), 7.37 (t, J=7.2 Hz, 4H), 7.31-7.25 (m, 3H), 7.19-7.1 (m, 4H).

Example 5

A) 3,5-Bis-(4-bromo-phenyl)-1-naphthalen-1-yl-1H-[1,2,4]triazole

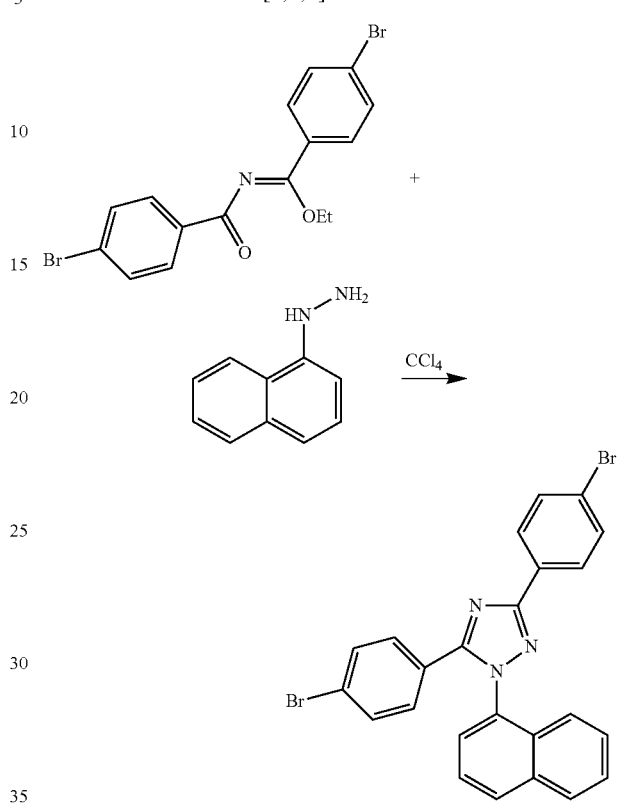

Naphthalene-1-hydrazine (2.5 g, 15.8 mmol) is added in portions to the acyl imidate prepared in Example 1A) (5.0 g, 12.1 mmol) in CCl$_4$ (60 ml) under a nitrogen atmosphere. The reaction mixture is stirred at room temperature for 7 h, the solvent is removed and the residue is chromatographed to obtain the desired triazole (yield: 2.5 g (41%), mp: 142-144° C.).

$^1$H NMR (ppm, CDCl$_3$): 8.13 (d, J=8.2 Hz, 2H), 8.03 (d, J=8.2 Hz, 1H), 7.97 (d, J=8.2 Hz, 1H), 7.61-7.42 (complex m, 7H), 7.39 (s, 4H).

B) 1-Naphthalene-1-yl-3,5-bis-(4-naphthalen-2-yl-phenyl)-1H-[1,2,4]triazole

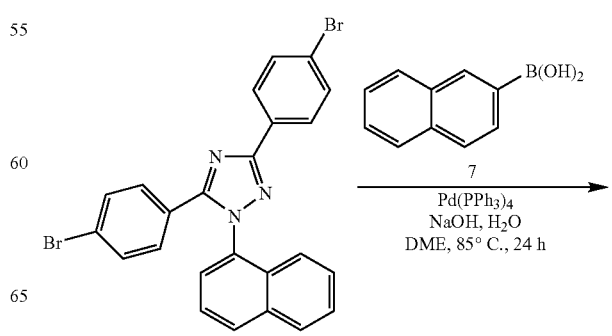

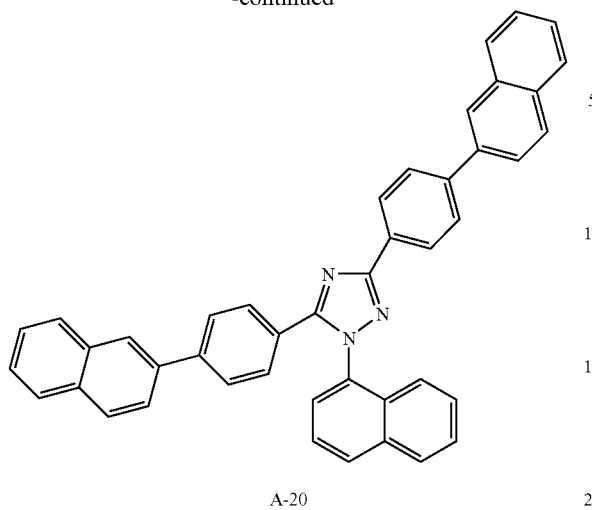

A-20

A sodium hydroxide solution (0.2 g NaOH dissolved in 5 ml of water) and 0.12 g (0.1 mmol) of Pd(PPh₃)₄ are added to 0.8 g (1.58 mmol) of the triazole obtained in step A) and 0.66 g (3.8 mmol) of naphthalene-2-boronic acid (7) in 12 ml of 1,2-dimethoxy ethane under a nitrogen atmosphere. The reaction mixture is stirred and heated at 85° C. for 24 h. The obtained brownish solid is filtered after cooling the reaction mixture to 15° C. The solid mass is taken up in 25 ml of ethyl acetate, stirred for 2 h at 60° C. and filtered in hot condition to obtain the desired compound A-20 (yield: 0.67 g (71%); mp: >250° C.).

$^1$H NMR (ppm, CDCl₃): 8.43 (d, J=7.8 Hz, 2H), 8.14 (s, 1H), 8.06 (t, J=4.6 Hz, 1H), 8.01-7.8 (complex m, 11H), 7.7-7.42 (complex m, 14H).

Example 6

A) 5-(3-Bromo-phenyl)-3-(4-bromo-phenyl)-1-phenyl-1H-[1,2,4]triazole

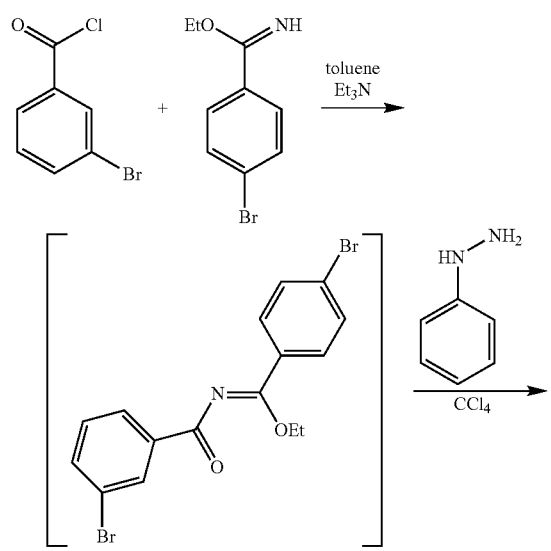

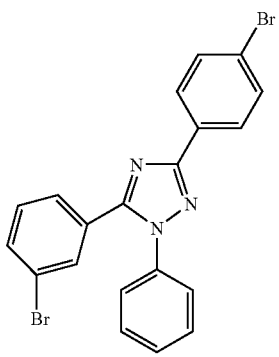

Triethyl amine (2 ml) is added to 2.5 g (10.9 mmol) of the imidate ether shown above in toluene (15 ml) and the reaction mixture is cooled to 15° C. 3-bromo benzoyl chloride (2.4 g, 10.9 mmol) in toluene (15 ml) is then added slowly to the stirred solution under nitrogen. The reaction mixture is stirred for 7 h at room temperature, filtered to remove the triethyl amine hydrochloride salt and concentrated to obtain the acyl imidate shown above, which is used without further purification for the cyclization reaction with phenyl hydrazine.

Phenyl hydrazine (1.2 g, 11.0 mmol) is added slowly to 4.5 g of the crude acyl imidate in CCl₄ (60 ml). The reaction mixture is stirred for 7 h at room temperature. The obtained brownish precipitate is filtered and the CCl₄ is concentrated to obtain a reddish colored residue. After addition of methanol a solid mass precipitated, which is filtered and washed with hexane, wherein 1.32 g of the desired compound are obtained (yield: 27%; mp: 129-131° C.).

$^1$H NMR (ppm, CDCl₃): 8.1 (d, J=8.2 Hz, 2H), 7.81 (s, 1H), 7.6 (d, J=8.2 Hz, 2H), 7.55 (d, J=8.2 Hz, 1H), 7.5-7.35 (complex m, 6H), 7.21 (m, 1H).

B) 5-(3-Naphthalen-2-yl-phenyl)-3-(4-naphthalen-2-yl-phenyl)-1-phenyl-1H[1,2,4]triazole

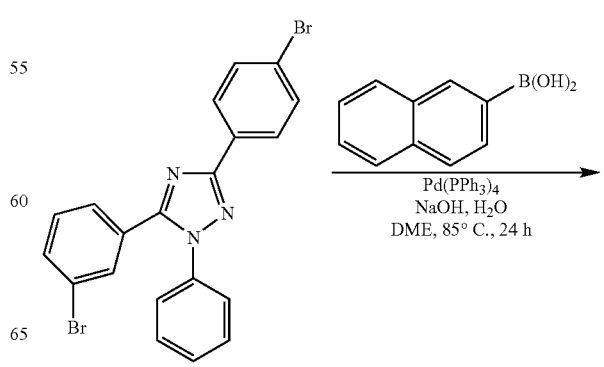

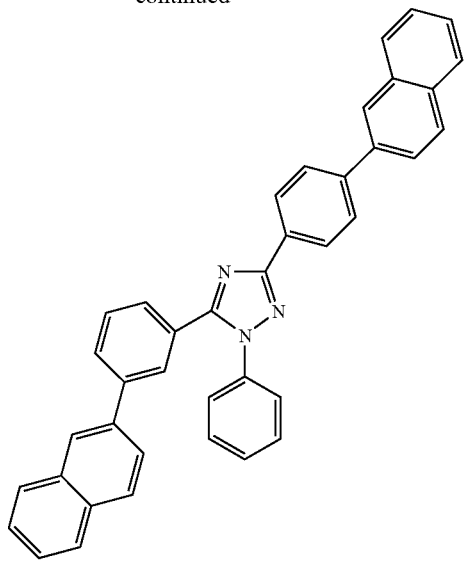

A-21

Sodium hydroxide solution (0.2 g NaOH dissolved in 5 ml of water) and 0.12 g (0.1 mmol) of Pd(PPh$_3$)$_4$ are added to 0.9 g (1.97 mmol) of the triazole obtained in step A) and 0.82 g (4.7 mmol) of naphthalene-2-boronic acid in 15 ml of 1,2-dimethoxy ethane under a nitrogen atmosphere. The reaction mixture is heated at 85° C. for 24 h, cooled and extracted with ethyl acetate. The organic solvent is removed and the residue is chromatographed. 0.4 g of desired compound A-21 is obtained as greenish solid (yield (40%); mp: 156-158° C.).

$^1$H NMR (ppm, CDCl$_3$): 8.38 (d, J=7.8 Hz, 2H), 8.12 (s, 1H), 7.88-7.75 (complex m, 12H), 7.67-7.41 (complex m, 12H).

Examples 7-12

Compounds A-6, A-7, A-14, A-15, B-1 and B-4 are synthesized in analogy to the procedures described for Examples 1-6.

Application Example 1

The following device structure is prepared: ITO/CuPC/TCTA/Compound A-1/TPBI/LiF/Al where ITO is indium tin oxide, CuPC is copper phthalocyanine, TCTA is 4,4',4"-tri-(N-carbazoyl)triphenylamine, and TPBI is 1,3,5-tris-(N-phenyl-benzimidazol-2-yl)benzene. Using this device structure, a brightness of 153 cd/m$^2$ is observed with a efficiency of 1.0 cd/A at 9V with an emission $\lambda_{max}$ at 438, 502 nm.

Application Example 2

The following device structure is prepared: ITO/CuPC/TCTA/Compound A-1+Compound 1 (2.4% by weight)/TPBI/LiF/Al. Using this device structure, a brightness of 86 cd/m$^2$ is observed with a efficiency of 2.7 cd/A at 9V with an emission $\lambda_{max}$ at 441 nm.

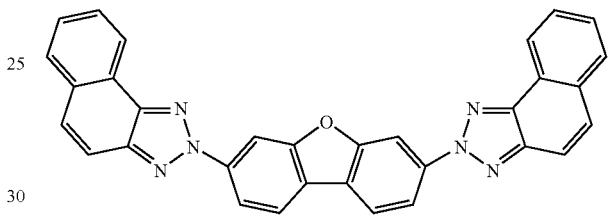

Compound 1 (Disclosed in WO2004039786)

Application Example 3

The following device structure is prepared: ITO/CuPC/TCTA/Compound A-2/TPBI/LiF/Al. Using this device structure, a brightness of 84 cd/m$^2$ is observed with a efficiency of 0.5 cd/A at 10 V with an emission $\lambda_{max}$ at 440 nm.

| Example | Compound | Mp. [° C.] | $^1$H NMR [ppm, CDCl$_3$] |
|---|---|---|---|
| 7 | A-6 | 210-212 | 8.44 (d, J = 8.2 Hz, 2H), 7.92-7.85 (m, 10H), 7.72-7.70 (m, 6H), 7.61-7.46 (complex m, 15H) |
| 8 | A-7 | >240 | 8.41 (d, J = 8.2 Hz, 2H), 8.03-7.9 (m, 3H), 7.81-7.74 (m, 4H), 7.72-7.3 (complex m, 24H) |
| 9 | A-14 | 202-205 | 8.38 (d, J = 8.2 Hz, 2H), 8.1 (s, 1H), 8.0 (s, 1H), 7.98-7.8 (complex m, 9H), 7.8-7.68 (m, 5H), 7.58-7.44 (m, 9H) |
| 10 | A-15 | >225 | 8.4 (d, J = 8.2 Hz, 2H), 8.14 (s, 1H), 8.1 (d, J = 5.8 Hz, 2H), 7.98-7.74 (complex m, 20H), 7.64 (d, J = 8.2 Hz, 2H), 7.56-7.48 (m, 6H) |
| 11 | B-1 | >230 | 8.57(d, J = 7.8 Hz, 2H), 8.18-8.15 (m, 6H), 7.86-7.73 (complex m, 8H), 7.54-7.42 (complex m, 14H), 7.34-7.30 (m, 6H) |
| 12 | B-4 | 190-192 | 8.51(d, J = 8.6 Hz, 2H), 8.16 (t, J = 7.04 Hz, 4H), 7.86(d, J = 8.6 Hz, 2H), 7.72 (d, J = 8.2 Hz, 2H), 7.64 (d, J = 8.2 Hz, 2H), 7.58-7.50 (complex m, 7H), 7.47-7.41(complex m, 6H), 7.31 (t, J = 7.04 Hz, 4H) |

Application Example 4

The following device structure is prepared: ITO/CuPC/TCTA/Compound A-2+Compound 1 (1.0% by weight)/TPBI/LiF/Al. Using this device structure, a brightness of 70 cd/m² is observed with a efficiency of 1.4 cd/A at 11V with an emission $\lambda_{max}$ at 440 nm.

Application Example 5

The following device structure is prepared: ITO/CuPC/TCTA/Compound A-3/TPBI/LiF/Al. Using this device structure, a brightness of 130 cd/m² is observed with a efficiency of 0.9 cd/A at 11V with an emission $\lambda_{max}$ at 441, 531 nm.

Application Example 6

The following device structure is prepared: ITO/CuPC/TCTA/Compound A-3+Compound 1 (1.6% by weight)/TPBI/LiF/Al. Using this device structure, a brightness of 98 cd/m² is observed with a efficiency of 1.0 cd/A at 11V with an emission $\lambda_{max}$ at 441 nm.

Application Examples 7-13

The following device structure is prepared: ITO/CuPC/NPD/Emitting layer (1,2,4-triazole of the present invention as a host+TBPe as a guest)/TPBI/LiF/Al where ITO is indium tin oxide, CuPC is copper phthalocyanine, NPD is N,N'-Di(naphthalene-1-yl)-N,N'-diphenyl-benzidine, TBPe is 2,5,8,11-tetra-t-butylperylene and TPBI is 1,3,5-tris-(N-phenyl-benzimidazol-2-yl)benzene. Using this device structure, bright blue EL emission is observed. The EL properties of the devices are summarized in the Table below.

| Application Example | Host | Guest (TBPe) concentration [%] | Brightness [cd/m²] | Current efficiency [cd/A] | Voltage [V] | Emission peak [nm] |
|---|---|---|---|---|---|---|
| 7 | A-3 | 1.5 | 95 | 2.4 | 9.4 | 463, 490 |
| 8 | A-6 | 2.7 | 110 | 1.7 | 8.0 | 465, 490 |
| 9 | A-14 | 1.6 | 133 | 3.3 | 7.9 | 436, 489 |
| 10 | A-19 | 1.4 | 111 | 1.9 | 8.4 | 465, 491 |
| 11 | A-20 | 2.3 | 107 | 2.7 | 8.3 | 465, 490 |
| 12 | A-21 | 1.8 | 111 | 2.8 | 9.0 | 465, 490 |
| 13 | B-4 | 1.7 | 75 | 2.6 | 8.0 | 466, 492 |

Application Examples 14-16

The following device structure is prepared: ITO/CuPC/NPD/Emitting material (1,2,4-triazole of the present invention as a host+btp₂Ir(acac) as a guest)/BCP/Alq₃/LiF/Al where BCP is bathocuproine and Alq₃ is tris-(8-hydroxyquinolinato)-aluminium. Using this device structure, pure red EL emission is observed. The EL properties are summarized in the Table below.

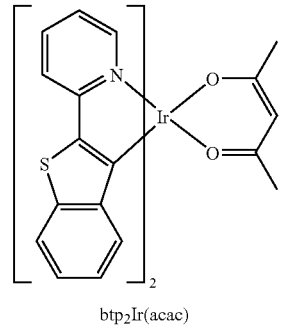

btp₂Ir(acac)

| Application Example | Host | Guest[1] concentration [%] | Brightness [cd/m²] | Current efficiency [cd/A] | Voltage [V] | Emission peak [nm] |
|---|---|---|---|---|---|---|
| 14 | A-14 | 8.9 | 81 | 4.1 | 9.6 | 617 |
| 15 | A-20 | 7.9 | 110 | 2.7 | 11.1 | 617 |
| 16 | A-21 | 7.0 | 75 | 3.7 | 10.9 | 616 |

[1](btp₂Ir(acac)).

The invention claimed is:
1. A compound of the formula:

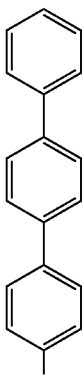

(A-1)

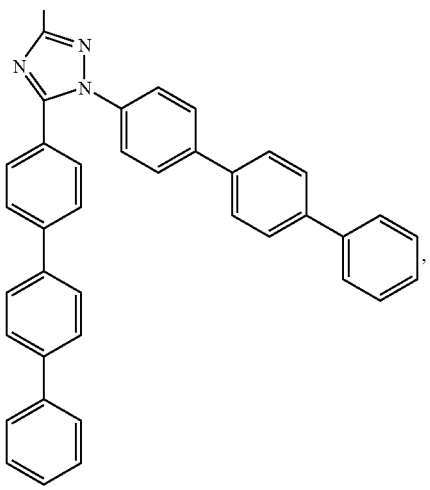
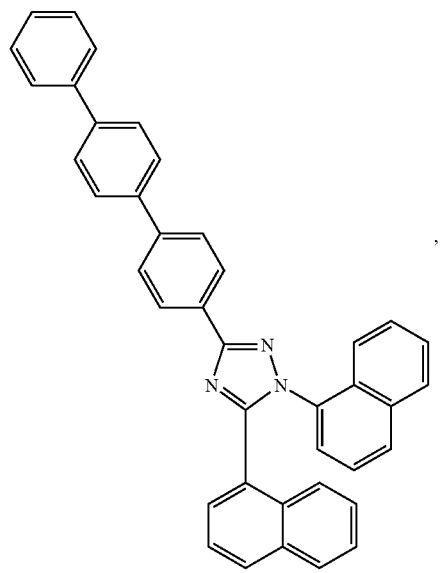
(A-2)
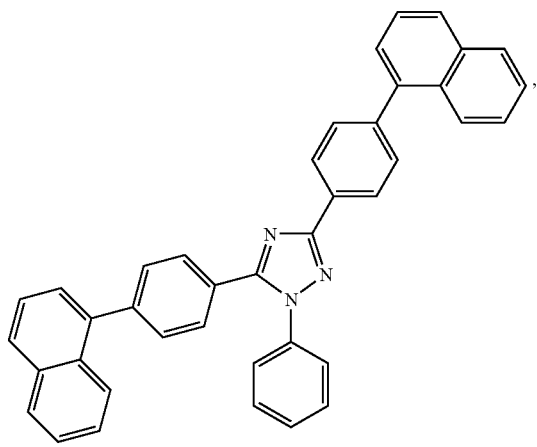
(A-3)
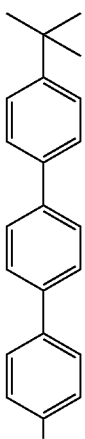
(A-4)

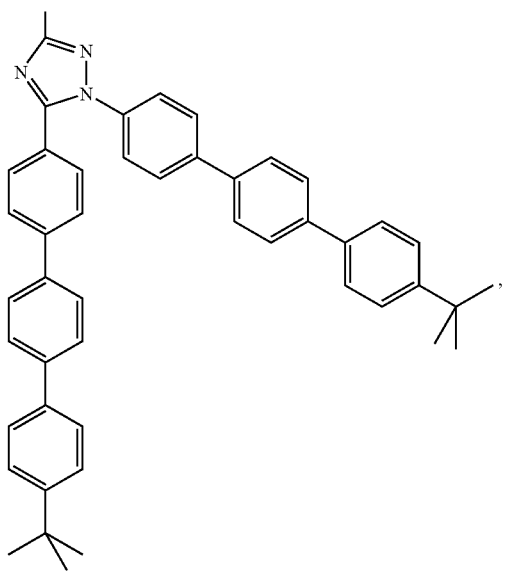
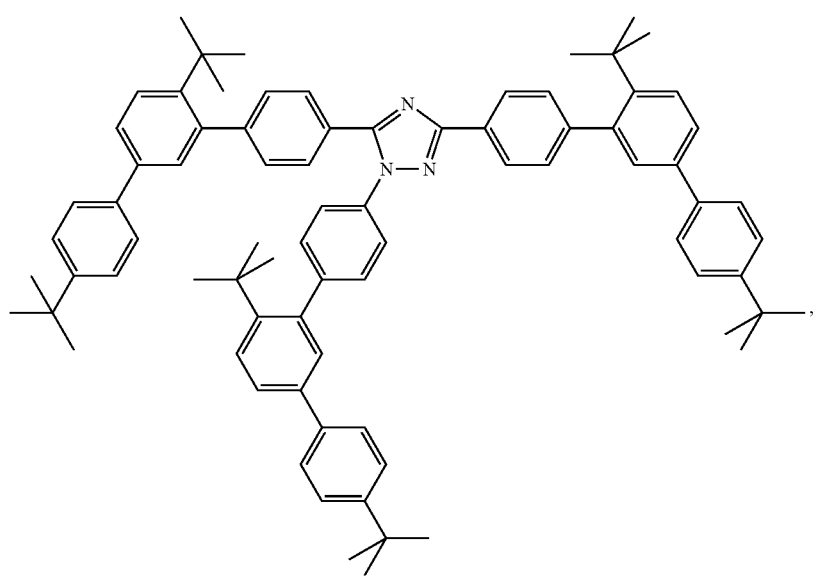
(A-5)

-continued
(A-6)
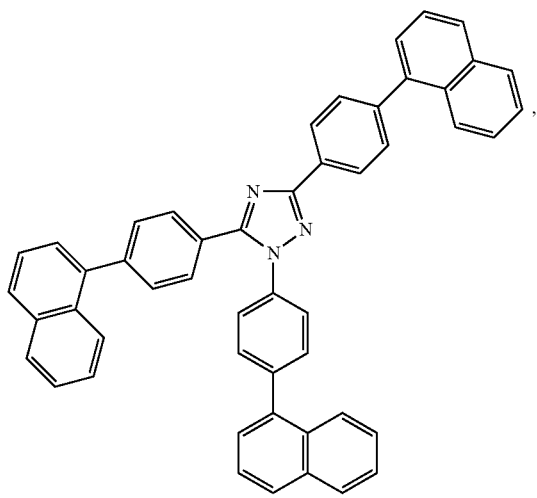
(A-7)
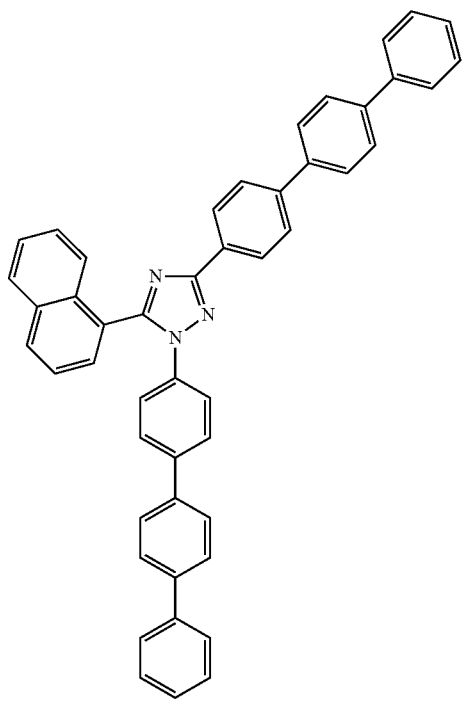
(A-8)
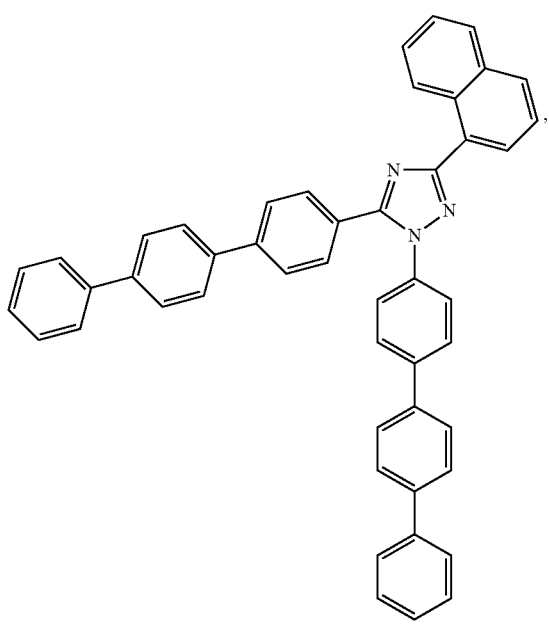
(A-9)
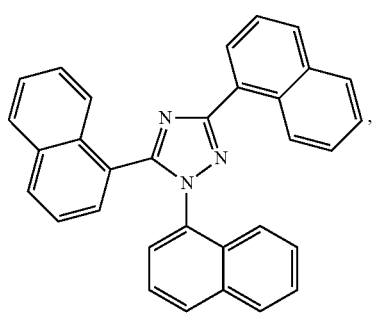

-continued
(A-10)
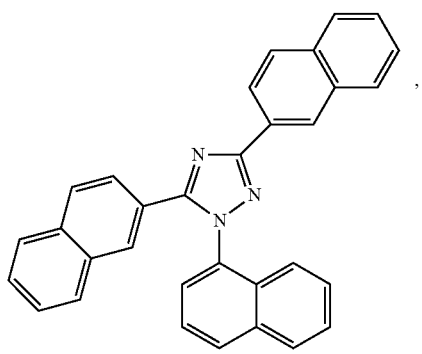
(A-11)
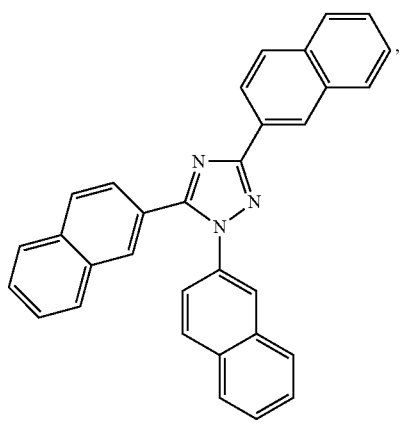
(A-12)
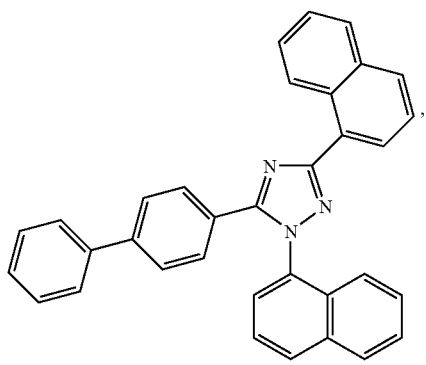
(A-13)
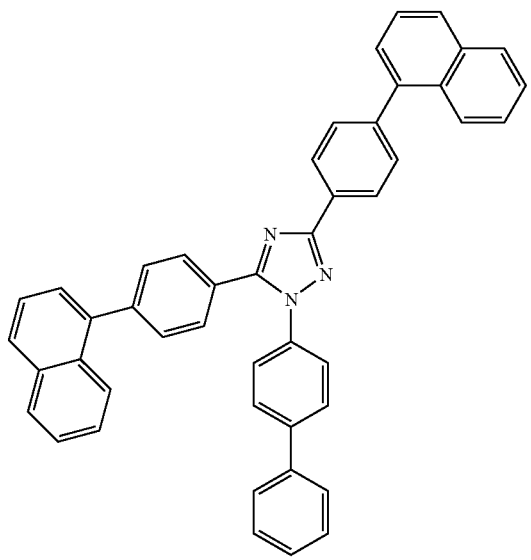
(A-14)
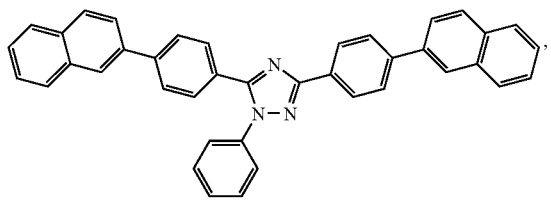
(A-15)
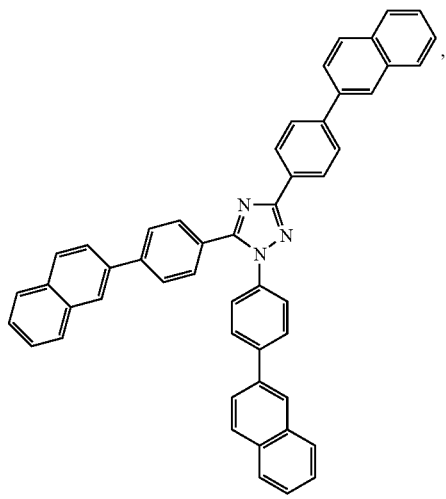

-continued
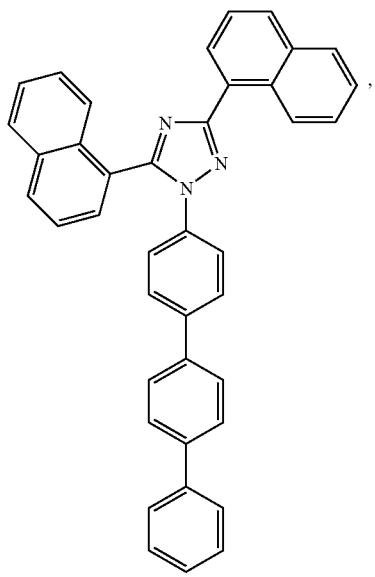
(A-16)
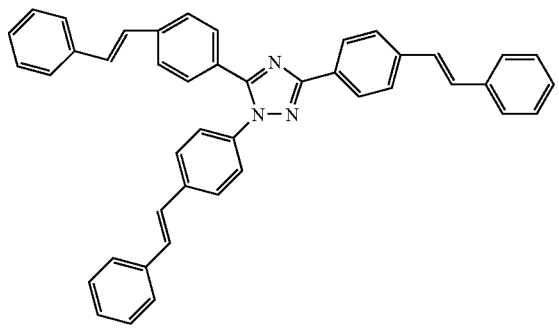
(A-17)
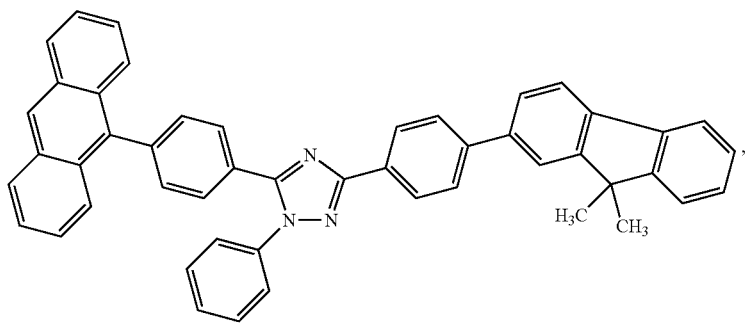
(A-18)
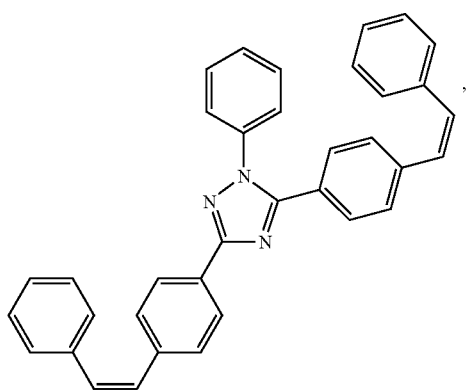
(A-19)
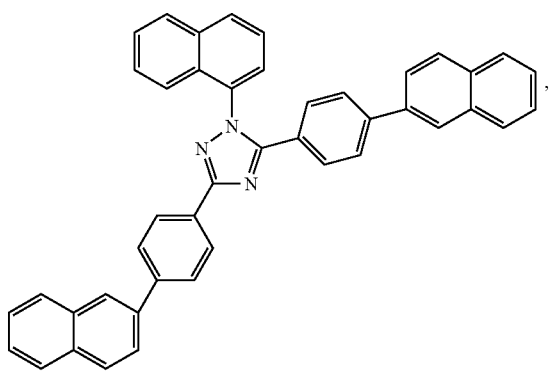
(A-20)

-continued
(A-21) 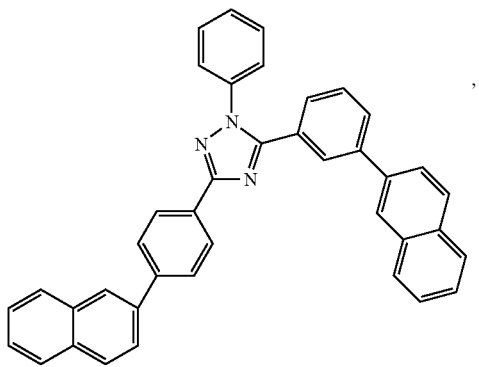
(A-22) 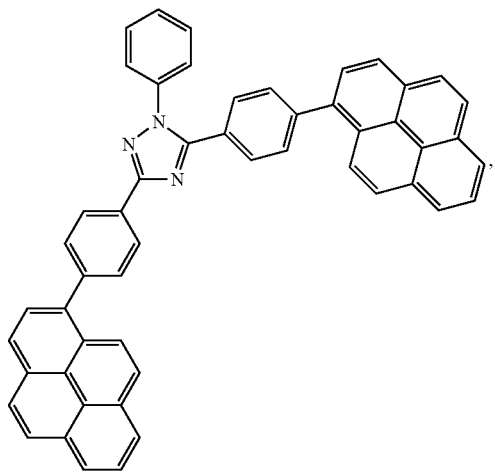
(A-23) 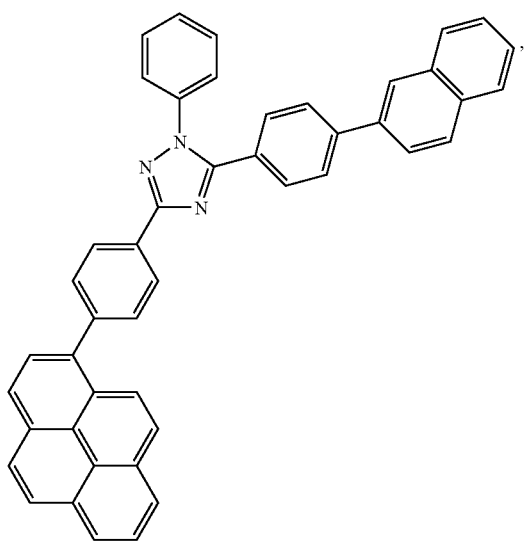
(A-24) 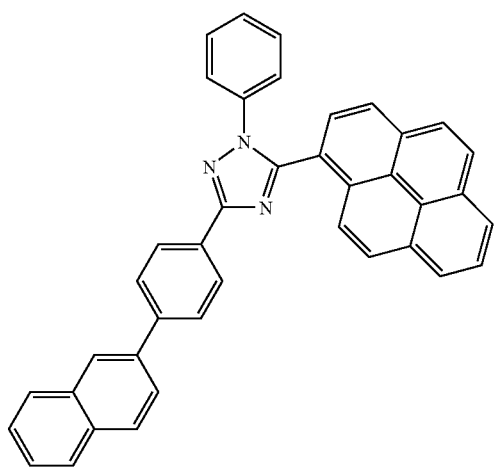
(A-25) 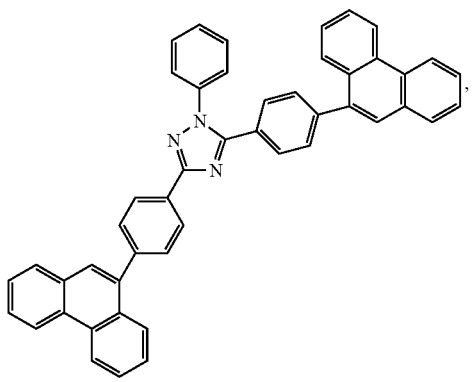
(A-26) 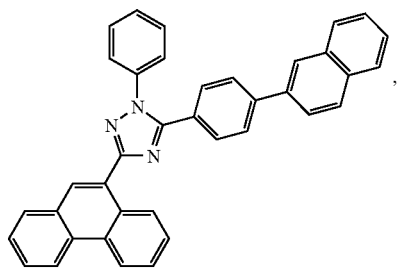

(A-27)
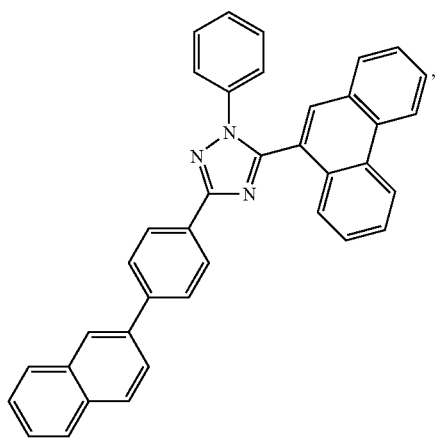
(A-28)
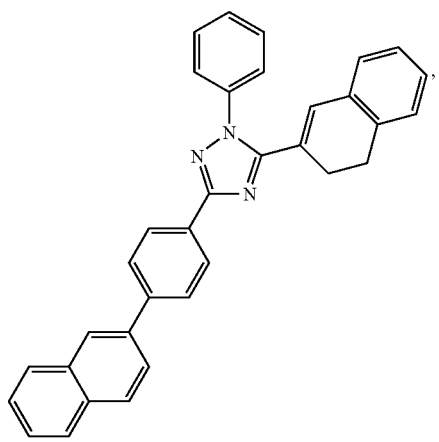
(A-29)
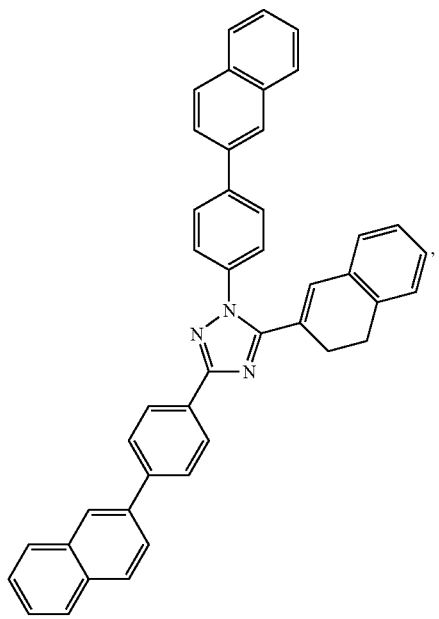
(C-1)
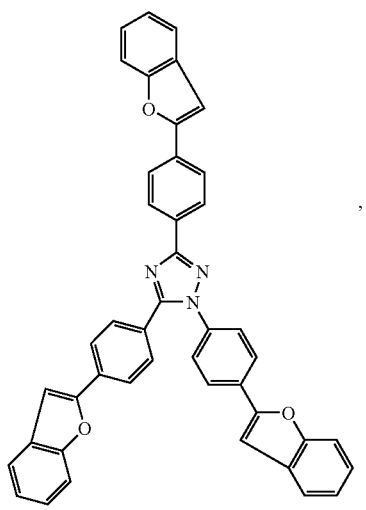

-continued
(C-2)
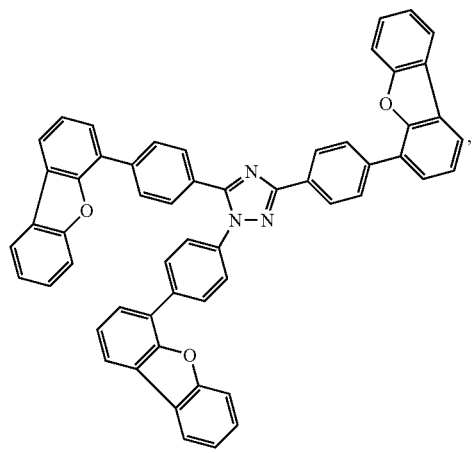
(C-3)
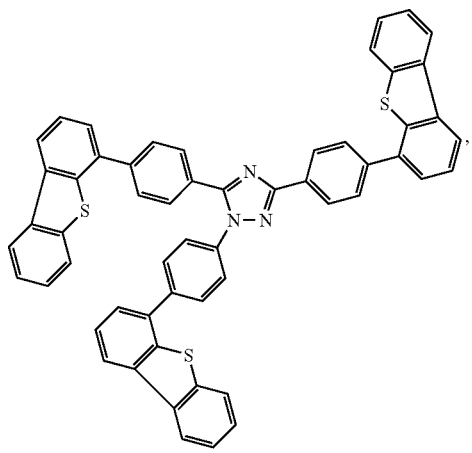
(C-4)
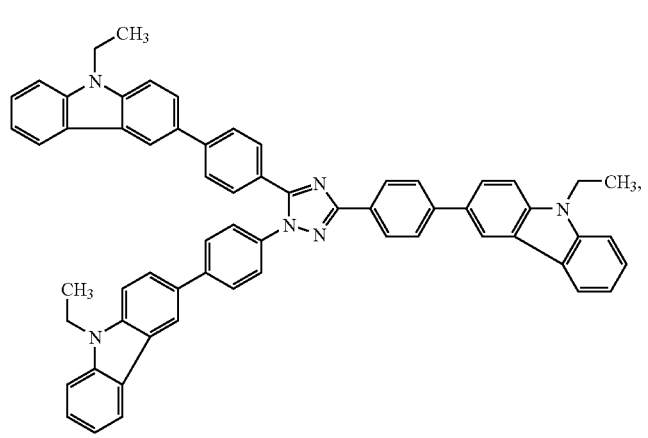
(C-5)
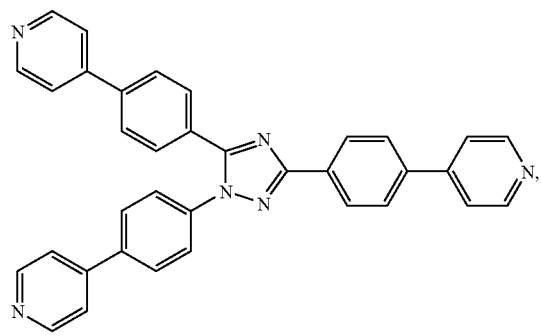
(C-6)
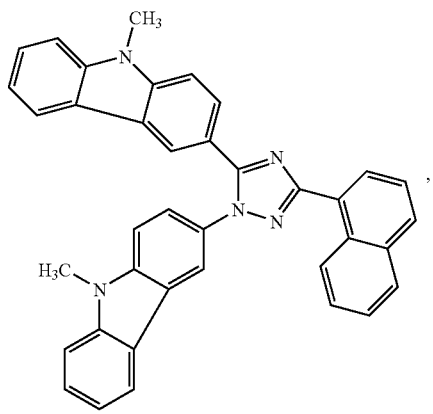

-continued
(C-7)
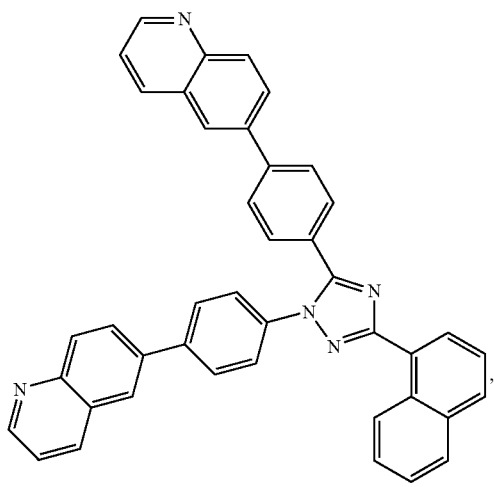
(C-8)
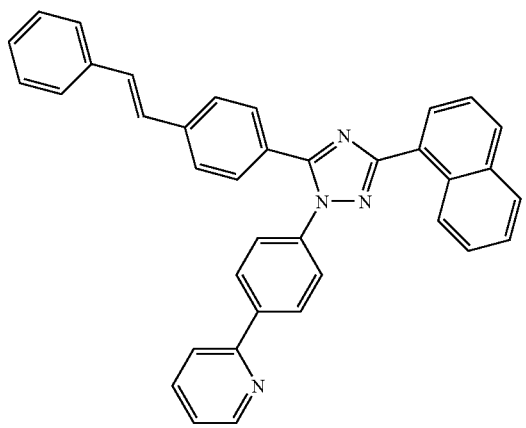
(C-9)
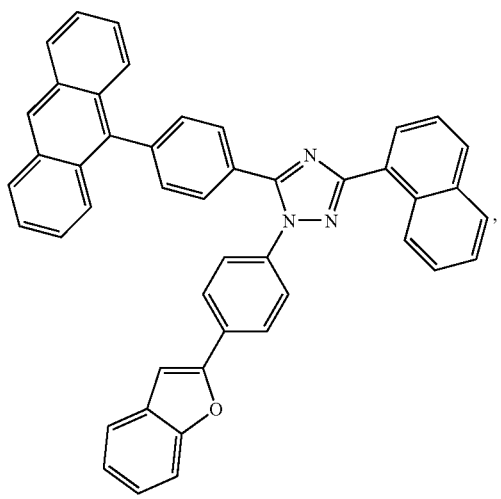
(C-10)
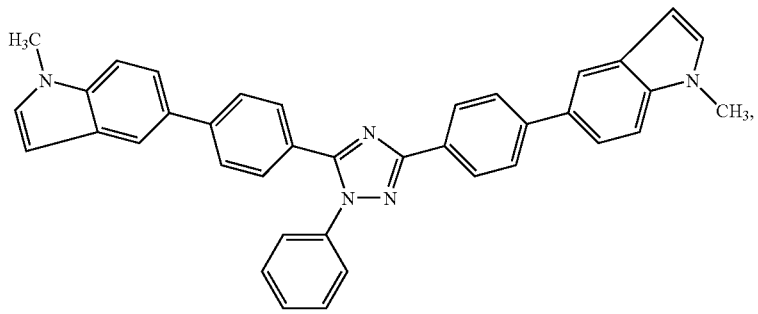
(C-11)
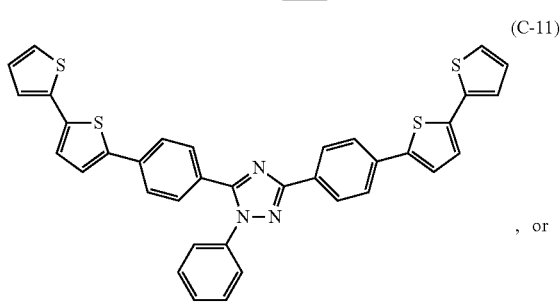
, or
(C-12)
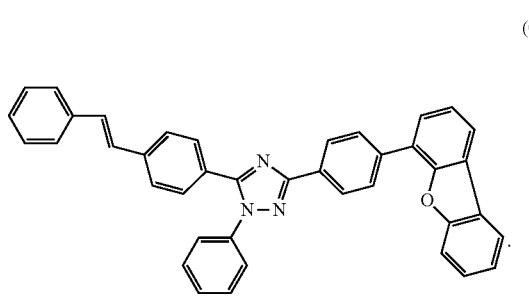

2. A compound of the formula

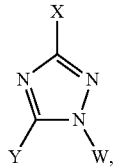
(I)

wherein

X, Y and W are a group of the formula —$W^1$-$(W^2)_b$-$W^3$, wherein b is 0, or, 1, $W^1$ and $W^2$ are independently of each other a group of formula

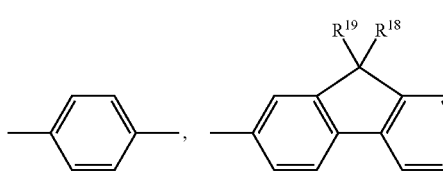

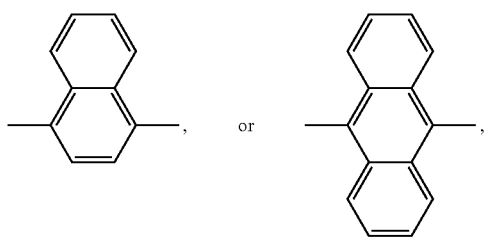

$R^{18}$ and $R^{19}$ are independently of each other $C_1$-$C_8$ alkyl or cyclohexyl, and $W^3$ is a group of formula

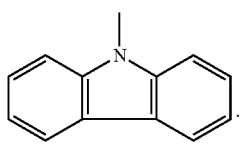

3. A compound of the formula:

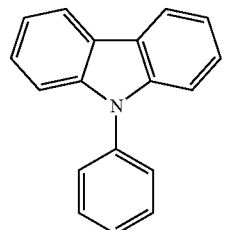
(B-1)

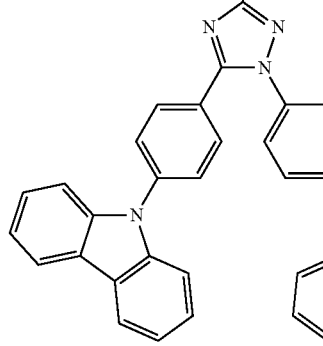

or

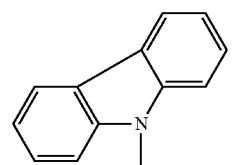
(B-4)

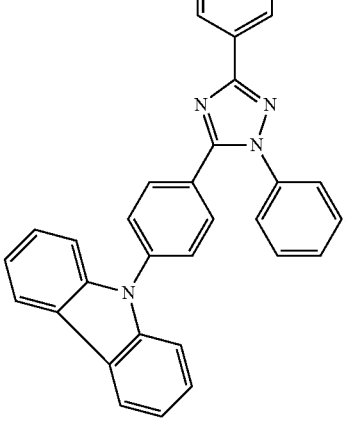

4. A composition, comprising a compound according to claim 2 and a phosphorescent compound.

5. An electroluminescent device, comprising a compound according to claim 2.

6. Electroluminescent device according to claim 5, wherein the electroluminescent device comprises in this order
   (a) an anode,
   (b) a hole injecting layer and/or a hole transporting layer,
   (c) a light-emitting layer,
   (d) optionally an electron transporting layer and
   (e) a cathode.

7. An electrophotographic photoreceptor, photoelectric converter, solar cell, image sensor or dye laser comprising a compound according to claim 2.

8. An electrophotographic photoreceptor, photoelectric converter, solar cell, image sensor or dye laser comprising a composition according to claim 4.

9. An electroluminescent device, comprising a composition according to claim 4.

10. Electroluminescent device according to claim 9, wherein the electroluminescent device comprises in this order
(a) an anode,
(b) a hole injecting layer and/or a hole transporting layer,
(c) a light-emitting layer,
(d) optionally an electron transporting layer and
(e) a cathode.

* * * * *